United States Patent
Grammann et al.

(10) Patent No.: US 9,944,959 B2
(45) Date of Patent: Apr. 17, 2018

(54) PRODUCTION OF FATTY ACIDS ESTERS

(71) Applicant: CARGILL, INCORPORATED, Wayzata, MN (US)

(72) Inventors: Katrin Grammann, Oer-Erkenschwick (DE); Jan Wolter, Duesseldorf (DE); Liv Reinecke, Essen (DE); Steffen Schaffer, Herten (DE); Eileen C. Spindler, Lafayette, CO (US); Wendy K. Ribble, Arvada, CO (US); Brittany L. Prather, Wheat Ridge, CO (US); Catherine B. Poor, Boulder, CO (US); Tanya Warnecke Lipscomb, Boulder, CO (US); Hans H. Liao, Superior, CO (US); Dave A. Hogsett, Longmount, CO (US); Ronald J. Evans, Louisville, CO (US)

(73) Assignee: CARGILL, INCORPORATED, Wayzata, MN (US)

( * ) Notice: Subject to any disclaimer, the term of this patent is extended or adjusted under 35 U.S.C. 154(b) by 243 days.

(21) Appl. No.: 14/843,525

(22) Filed: Sep. 2, 2015

(65) Prior Publication Data
US 2016/0060663 A1 Mar. 3, 2016

Related U.S. Application Data

(60) Provisional application No. 62/044,621, filed on Sep. 2, 2014.

(51) Int. Cl.
*C12P 7/64* (2006.01)
*C12N 9/10* (2006.01)
*C12N 1/00* (2006.01)
*C12Q 1/00* (2006.01)

(52) U.S. Cl.
CPC .......... *C12P 7/6436* (2013.01); *C12N 9/1029* (2013.01); *C12Y 203/01041* (2013.01); *C12Y 203/01075* (2013.01)

(58) Field of Classification Search
None
See application file for complete search history.

(56) References Cited

U.S. PATENT DOCUMENTS

| | | | |
|---|---|---|---|
| 7,118,896 B2 * | 10/2006 | Kalscheuer | C12N 9/1029 435/134 |
| 2011/0072714 A1 | 3/2011 | Gaertner | |
| 2011/0162259 A1 | 7/2011 | Gaertner | |
| 2013/0078684 A1 | 3/2013 | Holtzapple et al. | |
| 2013/0078686 A1 | 3/2013 | Holtzapple et al. | |
| 2014/0051136 A1 | 2/2014 | Liao et al. | |
| 2014/0215904 A1 | 8/2014 | Pandey et al. | |
| 2015/0299679 A1 | 10/2015 | Shumaker et al. | |

FOREIGN PATENT DOCUMENTS

| | | |
|---|---|---|
| WO | WO 2012/135760 A1 | 10/2012 |
| WO | WO 2014/026162 A1 | 2/2014 |
| WO | WO 2014/042693 A1 | 3/2014 |

OTHER PUBLICATIONS

Extended European Search Report dated Mar. 7, 2016 in Patent Application 15182914.0.
Gerhard Knothe, et al., "Biodiesel and Renewable Diesel: A Comparison" Progress in Energy and Combustion Science, vol. 36, No. 3, XP026919218, Jun. 1, 2010, pp. 364-373.
Partial European Search Report dated Jan. 8, 2016 in Patent Application No. 15182914.0.
Helge Jans Janβen et al., "Fatty Add Synthesis in *Escherichia coli* and its Applications Towards the Production of Fatty Acid Based Biofuels", Biotechnology for Biofuels, vol. 7, No. 1, XP-021173667, Jan. 9, 2014, 26 pages.

* cited by examiner

Primary Examiner — Suzanne M Noakes
Assistant Examiner — Jae W Lee

(57) ABSTRACT

A microbial cell is used for producing at least one fatty acid ester, wherein the cell is genetically modified to contain (i) at least one first genetic mutation that enables the cell to produce at least one fatty acid and/or acyl coenzyme A (CoA) thereof by increased enzymatic activity in the cell relative to the wild type cell of malonyl-CoA dependent and malonyl-ACP independent fatty acyl-CoA metabolic pathway, wherein the fatty acid contains at least 5 carbon atoms; and (ii) a second genetic mutation that increases the activity of at least one wax ester synthase in the cell relative to the wild type cell and the wax ester synthase has sequence identity of at least 50% to a polypeptide of SEQ ID NO: 1-8 and combinations thereof or to a functional fragment of any of the polypeptides for catalyzing the conversion of fatty acid and/or acyl coenzyme A thereof to the fatty acid ester.

14 Claims, 10 Drawing Sheets

SEQUENCE LISTING

<160> NUMBER OF SEQ ID NOS: 34

<210> SEQ ID NO 1
<211> LENGTH: 466
<212> TYPE: PRT
<213> ORGANISM: Singularimonas variicoloris (Svar)

<400> SEQUENCE: 1

```
Met Glu Ser Pro Arg Thr Pro Met His Val Gly Gly Leu Met Thr Phe
1               5                   10                  15

Arg Leu Pro Pro Asp Ala Pro Asp Phe Leu Arg Gln Leu Phe Ala
            20                  25                  30

Arg Leu Arg Ala Gln Met Pro Ser Thr Glu Pro Phe Asn Leu Arg Leu
        35                  40                  45

Ala Arg Thr Pro Trp Ser Ala Leu Ala Pro Ala Trp Glu Pro Ala Pro
50                  55                  60

Asp Ile Asp Ile Asp Tyr His Val Arg His Ser Ala Leu Pro Tyr Pro
65                  70                  75                  80

Gly Gly Glu Arg Glu Leu Gly Val Leu Val Ser Arg Leu His Ser His
                85                  90                  95

Pro Leu Asp Leu Arg Arg Pro Pro Trp Glu Ile Thr Leu Ile Glu Gly
            100                 105                 110

Leu Glu Asn Asp Arg Phe Ala Phe Phe Leu Lys Val His His Ser Ala
        115                 120                 125

Leu Asp Gly Met Gly Ala Leu Lys Leu Val Arg Arg Trp Leu Ser Ala
    130                 135                 140

Asp Ala Leu Gln Arg Asp Met Pro Ala Leu Trp Ala Leu Pro Ala Gln
145                 150                 155                 160

Pro Arg Glu Ala Arg Asp Ala Pro His Gly His Ala Val Glu Gln Gly
                165                 170                 175

Val Glu Ala Leu Arg Thr Gln Leu Arg Ala Ser Gly Glu Leu Leu Ser
            180                 185                 190

Thr Leu Arg Arg Met Ala Arg Arg Asp Asn Pro Glu Gly Gly Ile
        195                 200                 205

Leu Ser Ala Leu Ser Thr Pro Arg Thr Leu Leu Asn Val Pro Ile Thr
    210                 215                 220

Pro Gln Arg Arg Leu Ala Thr Gln Leu Phe Glu Leu Ser Arg Ile Lys
225                 230                 235                 240

Ala Val Ser Ala Ala Thr Gln Ser Thr Val Asn Asp Val Ala Leu Ala
                245                 250                 255

Leu Ile Ala Gly Ala Val Arg Arg Tyr Leu Leu Glu Leu Asp Ala Leu
            260                 265                 270

Pro His Glu Pro Leu Val Ala Ser Val Pro Val Gly Leu Pro Arg Ala
        275                 280                 285

Asp Gly Lys Pro Gly Asn Ala Val Ala Gly Phe Val Val Pro Leu Glu
    290                 295                 300

Thr Gln Ala Asp Asp Pro Leu Asp Cys Leu His Val Val Arg Ala Val
305                 310                 315                 320

Thr Gln Arg Thr Lys Asp Gln Leu Arg Gly Met Ser Pro Glu Ala Leu
                325                 330                 335

Ala Gln Phe Thr Met Leu Gly Leu Ser Pro Leu Ile Leu Gly Gln Met
            340                 345                 350

Ala Arg Val Leu Ser His Leu Pro Pro Ile Phe Asn Phe Val Val Ser
        355                 360                 365
```

-continued

Asn Val Val Ala Ser Lys Glu Leu Leu Tyr Leu Glu Gly Ala Glu Leu
    370             375                 380

Glu Ala Met Tyr Pro Ile Ser Val Leu Phe Asp Gly Tyr Ala Leu Asn
385                 390                 395                 400

Val Thr Leu Val Gly Tyr His Asp Arg Leu Ser Leu Gly Phe Thr Gly
            405                 410                 415

Cys Arg Asp Ala Leu Pro Ser Leu Gln Arg Leu Ala Val Tyr Ser Ala
            420                 425                 430

Glu Ala Leu Glu Glu Leu Glu Arg Ala Ala Gly Leu Val Pro His Ala
        435                 440                 445

Ala Gly Ala Ala Glu His Ala Pro Ala Arg Arg Thr Arg Arg Arg Gly
    450                 455                 460

Ala His
465

<210> SEQ ID NO 2
<211> LENGTH: 458
<212> TYPE: PRT
<213> ORGANISM: Hahella chejuensis (Hche)

<400> SEQUENCE: 2

Met Thr Pro Leu Ser Pro Val Asp Gln Ile Phe Leu Trp Leu Glu Lys
1               5                   10                  15

Arg Gln Gln Pro Met His Val Gly Gly Leu His Ile Phe Ser Phe Pro
            20                  25                  30

Asp Asp Ala Asp Ala Lys Tyr Met Thr Glu Leu Ala Gln Gln Leu Arg
        35                  40                  45

Ala Tyr Ala Thr Pro Gln Ala Pro Phe Asn Arg Arg Leu Arg Gln Arg
    50                  55                  60

Trp Gly Arg Tyr Tyr Trp Asp Thr Asp Ala Gln Phe Asp Leu Glu His
65                  70                  75                  80

His Phe Arg His Glu Ala Leu Pro Lys Pro Gly Arg Ile Arg Glu Leu
                85                  90                  95

Leu Ala His Val Ser Ala Glu His Ser Asn Leu Met Asp Arg Glu Arg
            100                 105                 110

Pro Met Trp Glu Cys His Leu Ile Glu Gly Ile Arg Gly Arg Arg Phe
        115                 120                 125

Ala Val Tyr Tyr Lys Ala His His Cys Met Leu Asp Gly Val Ala Ala
    130                 135                 140

Met Arg Met Cys Val Lys Ser Tyr Ser Phe Asp Pro Thr Ala Thr Glu
145                 150                 155                 160

Met Pro Pro Ile Trp Ala Ile Ser Lys Asp Val Thr Pro Ala Arg Glu
                165                 170                 175

Thr Gln Ala Pro Ala Ala Gly Asp Leu Val His Ser Leu Ser Gln Leu
            180                 185                 190

Val Glu Gly Ala Gly Arg Gln Leu Ala Thr Val Pro Thr Leu Ile Arg
        195                 200                 205

Glu Leu Gly Lys Asn Leu Leu Lys Ala Arg Asp Asp Ser Asp Ala Gly
    210                 215                 220

Leu Ile Phe Arg Ala Pro Pro Ser Ile Leu Asn Gln Arg Ile Thr Gly
225                 230                 235                 240

Ser Arg Arg Phe Ala Ala Gln Ser Tyr Ala Leu Glu Arg Phe Lys Ala
                245                 250                 255

Ile Gly Lys Ala Phe Gln Ala Thr Val Asn Asp Val Val Leu Ala Val
            260                 265                 270

```
Cys Gly Ser Ala Leu Arg Asn Tyr Leu Leu Ser Arg Gln Ala Leu Pro
        275                 280                 285

Asp Gln Pro Leu Ile Ala Met Ala Pro Met Ser Ile Arg Gln Asp Asp
    290                 295                 300

Ser Asp Ser Gly Asn Gln Ile Ala Met Ile Leu Ala Asn Leu Gly Thr
305                 310                 315                 320

His Ile Ala Asp Pro Val Arg Arg Leu Glu Leu Thr Gln Ala Ser Ala
                325                 330                 335

Arg Glu Ser Lys Glu Arg Phe Arg Gln Met Thr Pro Glu Glu Ala Val
            340                 345                 350

Asn Tyr Thr Ala Leu Thr Leu Ala Pro Ser Gly Leu Asn Leu Leu Thr
        355                 360                 365

Gly Leu Ala Pro Lys Trp Gln Ala Phe Asn Val Val Ile Ser Asn Val
    370                 375                 380

Pro Gly Pro Asn Lys Pro Leu Tyr Trp Asn Gly Ala Arg Leu Glu Gly
385                 390                 395                 400

Met Tyr Pro Val Ser Ile Pro Val Asp Tyr Ala Ala Leu Asn Ile Thr
                405                 410                 415

Leu Val Ser Tyr Arg Asp Gln Leu Glu Phe Gly Phe Thr Ala Cys Arg
            420                 425                 430

Arg Thr Leu Pro Ser Met Gln Arg Leu Leu Asp Tyr Ile Glu Gln Gly
        435                 440                 445

Ile Ala Glu Leu Glu Lys Ala Ala Gly Val
450                 455

<210> SEQ ID NO 3
<211> LENGTH: 461
<212> TYPE: PRT
<213> ORGANISM: Acinetobacter junii (Ajun)

<400> SEQUENCE: 3

Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Glu Ile Pro
            20                  25                  30

Glu Asn Ala Ser Pro Thr Phe Val His Asp Leu Val Gln Asp Ile Arg
        35                  40                  45

Gln Ser Lys Ser Ile Pro Val Pro Pro Phe Asn Asn Gln Leu Asn Gly
    50                  55                  60

Leu Phe Trp Gly Glu Asp Pro Glu Phe Asp Ile Asp His His Phe Arg
65                  70                  75                  80

His Ile Ala Leu Pro Asn Pro Gly Arg Ile Arg Glu Leu Leu Val Tyr
                85                  90                  95

Ile Ser Gln Gln His Ser Ser Leu Ile Asp Arg Ala Lys Pro Leu Trp
            100                 105                 110

Thr Cys Asp Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser Lys Asp Pro Asn Glu Lys His Val Val Pro
145                 150                 155                 160

Leu Trp Cys Val Glu Gly Lys Arg Thr Lys Arg Leu Lys Ala Pro Lys
                165                 170                 175

Pro Pro Ser Val Ser Lys Ile Lys Gly Ile Met Asp Gly Ile Lys Ser
```

```
            180                 185                 190
    Gln Leu Glu Val Thr Pro Lys Val Met Gln Glu Leu Ser Gln Thr Ile
                195                 200                 205
    Phe Lys Glu Ile Gly Lys Asn Pro Asp Tyr Val Ser Thr Phe Gln Ala
                210                 215                 220
    Pro Pro Ser Ile Leu Asn Gln Arg Val Ser Ser Arg Arg Phe Ala
    225                 230                 235                 240
    Ala Gln Ser Phe Glu Leu Asp Arg Phe Arg Asn Ile Ala Lys Ser Leu
                    245                 250                 255
    Gly Val Thr Ile Asn Asp Val Val Leu Ala Val Cys Ala Gly Ala Leu
                260                 265                 270
    Arg Glu Tyr Leu Ile Ser His Glu Ser Leu Pro Lys Lys Pro Leu Ile
                275                 280                 285
    Ala Met Val Pro Ala Ser Leu Arg Thr Asp Asp Ser Asp Val Ser Asn
                290                 295                 300
    Arg Ile Thr Met Ile Leu Ala Asn Leu Ala Thr His Ile Glu Asp Pro
    305                 310                 315                 320
    Ile Glu Arg Leu Gln Ile Ile Arg Arg Ser Val Gln Asn Ser Lys Gln
                    325                 330                 335
    Arg Phe Ser Arg Met Thr Ala Asn Glu Ile Leu Asn Tyr Ser Ala Leu
                340                 345                 350
    Val Tyr Gly Pro Ala Gly Leu Asn Ile Val Ser Gly Met Leu Pro Lys
                355                 360                 365
    Arg Gln Ala Phe Asn Leu Val Ile Ser Asn Val Pro Gly Pro Arg Glu
                370                 375                 380
    Pro Leu Tyr Trp Asn Gly Ala Lys Leu Asp Ala Leu Tyr Pro Ala Ser
    385                 390                 395                 400
    Ile Val Met Asp Gly Gln Ala Leu Asn Ile Thr Met Thr Ser Tyr Leu
                    405                 410                 415
    Asp Lys Leu Glu Val Gly Leu Ile Ala Cys Arg Asn Ala Leu Pro Lys
                420                 425                 430
    Met Gln Asn Leu Leu Thr His Leu Glu Asp Glu Ile Gln Arg Phe Glu
                435                 440                 445
    Ser Ala Ile Leu Ser Leu Pro Lys Gln Ala Ala Glu Gly
                450                 455                 460

<210> SEQ ID NO 4
<211> LENGTH: 458
<212> TYPE: PRT
<213> ORGANISM: Amycolatopsis azurea (Aazu)

<400> SEQUENCE: 4

Met Pro Phe Met Pro Val Thr Asp Ser Met Phe Leu Leu Val Glu Thr
    1               5                   10                  15
    Arg Glu His Pro Met His Val Gly Gly Leu Gln Leu Phe Lys Lys Pro
                20                  25                  30
    Glu Asp Ala Gly Pro Asp Tyr Leu Arg Asp Leu Arg Arg Lys Leu Leu
                35                  40                  45
    Asp Ser Asp Asn Met Arg Asp Val Phe Arg Arg Pro Ala Arg Pro
    50                  55                  60
    Val Asn Thr Ala Gly His Val Ala Trp Ala Thr Asp Asn Asp Leu Glu
    65                  70                  75                  80
    Leu Asp Tyr His Phe Arg His Ser Ala Leu Pro Gln Pro Gly Arg Ile
                    85                  90                  95
```

```
Arg Glu Leu Leu Glu Leu Thr Gly Arg Trp His Ser Thr Leu Leu Asp
                100                 105                 110

Arg His Arg Pro Leu Trp Glu Ile His Leu Val Glu Gly Leu Gln Asp
            115                 120                 125

Gly Arg Phe Ala Ile Tyr Ser Lys Ile His His Ala Leu Met Asp Gly
        130                 135                 140

Val Ser Ala Leu Arg His Leu Gln Gly Thr Leu Ser Asp Asp Pro Thr
145                 150                 155                 160

Asp Leu Asp Cys Pro Pro Pro Trp Gly Arg Arg Pro Lys Pro Asp Gly
                165                 170                 175

Gly Arg Asn Gly Lys Ala Ser Pro Ser Val Leu Ser Thr Phe Gly Lys
            180                 185                 190

Thr Val Asn Gln Leu Ala Gly Ile Ala Pro Ala Ala Met Lys Val Ala
        195                 200                 205

Arg Glu Ala Phe Gln Glu His Thr Leu Thr Leu Pro Ala Gln Ala Pro
210                 215                 220

Lys Thr Met Leu Asn Val Pro Ile Gly Gly Ala Arg Arg Phe Ala Ala
225                 230                 235                 240

Gln Ser Trp Ser Leu Asp Arg Val Arg Lys Val Ala Thr Ala Ala Gly
                245                 250                 255

Val Ser Arg Asn Asp Val Val Leu Ala Met Cys Ser Gly Ala Leu Arg
            260                 265                 270

Asp Tyr Leu Ile Glu Gln Asn Ser Leu Pro Asp Ala Pro Leu Thr Ala
        275                 280                 285

Met Val Pro Val Ser Leu Arg Arg Lys Asp Ser Gly Asp Ala Ala Gly
290                 295                 300

Asn Asn Ile Gly Ala Leu Leu Cys Asn Leu Ala Thr His Leu Thr Asp
305                 310                 315                 320

Pro Ala Ala Arg Leu Ala Thr Ile Asn Ala Ser Met Arg Asn Gly Lys
                325                 330                 335

Lys Leu Phe Ser Glu Leu Thr Pro Leu Gln Thr Leu Leu Ser Gly
            340                 345                 350

Ile Asn Val Ala Gln Leu Gly Val Ser Pro Ile Pro Gly Phe Val Asn
        355                 360                 365

Asn Thr Lys Pro Pro Phe Asn Leu Val Ile Ser Asn Val Pro Gly Pro
370                 375                 380

Arg Lys Gln Met Tyr Trp Asn Gly Ala Ser Leu Asp Gly Ile Tyr Pro
385                 390                 395                 400

Ala Ser Val Leu Leu Asp Gly Gln Ala Leu Asn Ile Thr Leu Thr Ser
                405                 410                 415

Asn Gly Asp Asn Leu Asp Phe Gly Val Thr Gly Cys Arg Arg Ser Val
            420                 425                 430

Pro His Leu Gln Arg Ile Leu Thr His Leu Asp Thr Ala Leu Ala Glu
        435                 440                 445

Leu Glu His Ala Val Ser Val Gly Arg Ser
450                 455

<210> SEQ ID NO 5
<211> LENGTH: 460
<212> TYPE: PRT
<213> ORGANISM: Acinetobacter sp (Acip)

<400> SEQUENCE: 5

Met Arg Pro Leu His Pro Ile Asp Phe Ile Phe Leu Ser Leu Glu Lys
1               5                   10                  15
```

```
Arg Gln Gln Pro Met His Val Gly Gly Leu Phe Leu Phe Glu Leu Pro
             20                  25                  30
Glu Asn Ala Ser Pro Thr Phe Val His Asp Leu Val Asn Glu Ile Arg
         35                  40                  45
Gln Ser Lys Ser Ile Pro Val Pro Pro Phe Asn Asn Gln Leu Asn Gly
 50                  55                  60
Leu Phe Trp Gly Glu Asp Ser Glu Phe Asp Leu Asp His His Phe Arg
 65                  70                  75                  80
His Ile Ala Leu Pro Asn Pro Gly Arg Ile Arg Glu Leu Leu Val Tyr
                 85                  90                  95
Ile Ser Gln Gln His Ser Ser Leu Ile Asp Arg Ala Lys Pro Leu Trp
            100                 105                 110
Thr Cys Asp Ile Ile Glu Gly Ile Glu Gly Asn Arg Phe Ala Met Tyr
            115                 120                 125
Phe Lys Ile His His Ala Met Val Asp Gly Val Ala Gly Met Arg Leu
130                 135                 140
Ile Glu Lys Ser Leu Ser Gln Asp Pro Asn Glu Lys His Val Val Pro
145                 150                 155                 160
Leu Trp Cys Val Glu Gly Lys Arg Thr Lys Arg Leu Lys Ala Pro Lys
                165                 170                 175
Pro Pro Thr Val Ser Lys Ile Lys Gly Val Met Glu Gly Ile Lys Ser
            180                 185                 190
Gln Leu Glu Val Ala Pro Lys Val Met Gln Glu Leu Ser Gln Thr Ile
        195                 200                 205
Phe Lys Glu Met Gly Lys Asn Pro Asp Tyr Val Ser Thr Phe Gln Ala
    210                 215                 220
Pro Pro Ser Ile Leu Asn Gln Arg Val Ser Ser Arg Arg Phe Ala
225                 230                 235                 240
Ala Gln Ser Phe Glu Leu Gly Arg Phe Arg Arg Ile Ala Lys Ser Leu
                245                 250                 255
Gly Val Thr Leu Asn Asp Val Ile Leu Ala Val Cys Ser Gly Ala Leu
            260                 265                 270
Arg Glu Tyr Leu Ile Ser His Asn Ser Leu Pro Lys Lys Pro Leu Ile
        275                 280                 285
Ala Met Val Pro Ala Ser Leu Arg Thr Asp Asp Ser Asp Val Ser Asn
    290                 295                 300
Arg Ile Thr Met Ile Leu Ala Asn Leu Ala Thr His Ile Glu Asp Pro
305                 310                 315                 320
Ile Glu Arg Leu Glu Val Ile Arg Arg Ser Val Gln Asn Ser Lys Gln
                325                 330                 335
Arg Phe Ser Arg Met Thr Ala Asn Glu Ile Leu Asn Tyr Ser Ala Val
            340                 345                 350
Val Tyr Gly Pro Ala Gly Leu Asn Ile Ala Ser Gly Met Leu Pro Lys
        355                 360                 365
Arg Gln Ala Phe Asn Leu Val Ile Ser Asn Val Pro Gly Pro Arg Glu
    370                 375                 380
Pro Leu Tyr Trp Asn Gly Ala Lys Leu Asp Ala Leu Tyr Pro Ala Ser
385                 390                 395                 400
Ile Val Met Asp Gly Gln Ala Leu Asn Ile Thr Met Thr Ser Tyr Leu
                405                 410                 415
Asp Lys Leu Glu Val Gly Leu Ile Ala Cys Arg Asn Ala Leu Pro Lys
            420                 425                 430
```

```
Met Gln Asn Leu Leu Thr His Leu Glu Glu Ile Gln Arg Phe Glu
            435                 440                 445

Gln Ala Ile Gln Asp Leu Pro Gln Lys Val Ala Asn
        450                 455                 460

<210> SEQ ID NO 6
<211> LENGTH: 473
<212> TYPE: PRT
<213> ORGANISM: Marinobacter hydrocarbonoclasticus (Mhyt)

<400> SEQUENCE: 6

Met Lys Arg Leu Gly Thr Leu Asp Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Trp Thr Val Arg Pro His Gln
                165                 170                 175

Arg Arg Gly Ala Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350
```

```
Lys Ser Ala Leu Thr Gln Tyr Thr Met Leu Met Ser Pro Tyr Ile
            355                 360                 365

Leu Gln Leu Met Ser Gly Leu Gly Gly Arg Met Arg Pro Val Phe Asn
370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
            405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
            435                 440                 445

Val Tyr Thr Gly Glu Ala Leu Asp Glu Leu Glu Ser Leu Ile Leu Pro
450                 455                 460

Pro Lys Lys Arg Ala Arg Thr Arg Lys
465                 470

<210> SEQ ID NO 7
<211> LENGTH: 475
<212> TYPE: PRT
<213> ORGANISM: Marinobacter aquaeolei (T373M, Q420R)

<400> SEQUENCE: 7

Met Gly Ser Ser His His His His His His Ser Ser Gly Leu Val Pro
1               5                   10                  15

Arg Gly Ser His Met Thr Pro Leu Asn Pro Thr Asp Gln Leu Phe Leu
            20                  25                  30

Trp Leu Glu Lys Arg Gln Gln Pro Met His Val Gly Gly Leu Gln Leu
        35                  40                  45

Phe Ser Phe Pro Glu Gly Ala Pro Asp Asp Tyr Val Ala Gln Leu Ala
    50                  55                  60

Asp Gln Leu Arg Gln Lys Thr Glu Val Thr Ala Pro Phe Asn Gln Arg
65                  70                  75                  80

Leu Ser Tyr Arg Leu Gly Gln Pro Val Trp Val Glu Asp Glu His Leu
                85                  90                  95

Asp Leu Glu His His Phe Arg Phe Glu Ala Leu Pro Thr Pro Gly Arg
            100                 105                 110

Ile Arg Glu Leu Leu Ser Phe Val Ser Ala Glu His Ser His Leu Met
        115                 120                 125

Asp Arg Glu Arg Pro Met Trp Glu Val His Leu Ile Glu Gly Leu Lys
130                 135                 140

Asp Arg Gln Phe Ala Leu Tyr Thr Lys Val His His Ser Leu Val Asp
145                 150                 155                 160

Gly Val Ser Ala Met Arg Met Ala Thr Arg Met Leu Ser Glu Asn Pro
                165                 170                 175

Asp Glu His Gly Met Pro Pro Ile Trp Asp Leu Pro Cys Leu Ser Arg
            180                 185                 190

Asp Arg Gly Glu Ser Asp Gly His Ser Leu Trp Arg Ser Val Thr His
        195                 200                 205

Leu Leu Gly Leu Ser Gly Arg Gln Leu Gly Thr Ile Pro Thr Val Ala
    210                 215                 220

Lys Glu Leu Leu Lys Thr Ile Asn Gln Ala Arg Lys Asp Pro Ala Tyr
225                 230                 235                 240

Asp Ser Ile Phe His Ala Pro Arg Cys Met Leu Asn Gln Lys Ile Thr
```

```
                    245                 250                 255
Gly Ser Arg Arg Phe Ala Ala Gln Ser Trp Cys Leu Lys Arg Ile Arg
            260                 265                 270

Ala Val Cys Glu Ala Tyr Gly Thr Thr Val Asn Asp Val Val Thr Ala
            275                 280                 285

Met Cys Ala Ala Ala Leu Arg Thr Tyr Leu Met Asn Gln Asp Ala Leu
            290                 295                 300

Pro Glu Lys Pro Leu Val Ala Phe Val Pro Val Ser Leu Arg Arg Asp
305                 310                 315                 320

Asp Ser Ser Gly Gly Asn Gln Val Gly Val Ile Leu Ala Ser Leu His
                325                 330                 335

Thr Asp Val Gln Glu Ala Gly Glu Arg Leu Leu Lys Ile His His Gly
            340                 345                 350

Met Glu Glu Ala Lys Gln Arg Tyr Arg His Met Ser Pro Glu Glu Ile
            355                 360                 365

Val Asn Tyr Thr Ala Leu Thr Leu Ala Pro Ala Ala Phe His Leu Leu
            370                 375                 380

Thr Gly Leu Ala Pro Lys Trp Gln Met Phe Asn Val Val Ile Ser Asn
385                 390                 395                 400

Val Pro Gly Pro Ser Arg Pro Leu Tyr Trp Asn Gly Ala Lys Leu Glu
                405                 410                 415

Gly Met Tyr Pro Val Ser Ile Asp Met Asp Arg Leu Ala Leu Asn Met
            420                 425                 430

Thr Leu Thr Ser Tyr Asn Asp Arg Val Glu Phe Gly Leu Ile Gly Cys
            435                 440                 445

Arg Arg Thr Leu Pro Ser Leu Gln Arg Met Leu Asp Tyr Leu Glu Gln
            450                 455                 460

Gly Leu Ala Glu Leu Glu Leu Asn Ala Gly Leu
465                 470                 475

<210> SEQ ID NO 8
<211> LENGTH: 474
<212> TYPE: PRT
<213> ORGANISM: Marinobacter aquaeolei (E72K)

<400> SEQUENCE: 8

Met Gly Ser Ser His His His His His Ser Ser Gly Leu Val Pro Arg
1               5                   10                  15

Gly Ser His Met Thr Pro Leu Asn Pro Thr Asp Gln Leu Phe Leu Trp
            20                  25                  30

Leu Glu Lys Arg Gln Gln Pro Met His Val Gly Gly Leu Gln Leu Phe
        35                  40                  45

Ser Phe Pro Glu Gly Ala Pro Asp Asp Tyr Val Ala Gln Leu Ala Asp
    50                  55                  60

Gln Leu Arg Gln Lys Thr Glu Val Thr Ala Pro Phe Asn Gln Arg Leu
65                  70                  75                  80

Ser Tyr Arg Leu Gly Gln Pro Val Trp Val Lys Asp Glu His Leu Asp
                85                  90                  95

Leu Glu His His Phe Arg Phe Glu Ala Leu Pro Thr Pro Gly Arg Ile
            100                 105                 110

Arg Glu Leu Leu Ser Phe Val Ser Ala Glu His Ser His Leu Met Asp
        115                 120                 125

Arg Glu Arg Pro Met Trp Glu Val His Leu Ile Glu Gly Leu Lys Asp
    130                 135                 140
```

```
Arg Gln Phe Ala Leu Tyr Thr Lys Val His His Ser Leu Val Asp Gly
145                 150                 155                 160

Val Ser Ala Met Arg Met Ala Thr Arg Met Leu Ser Glu Asn Pro Asp
            165                 170                 175

Glu His Gly Met Pro Pro Ile Trp Asp Leu Pro Cys Leu Ser Arg Asp
        180                 185                 190

Arg Gly Glu Ser Asp Gly His Ser Leu Trp Arg Ser Val Thr His Leu
    195                 200                 205

Leu Gly Leu Ser Gly Arg Gln Leu Gly Thr Ile Pro Thr Val Ala Lys
210                 215                 220

Glu Leu Leu Lys Thr Ile Asn Gln Ala Arg Lys Asp Pro Ala Tyr Asp
225                 230                 235                 240

Ser Ile Phe His Ala Pro Arg Cys Met Leu Asn Gln Lys Ile Thr Gly
            245                 250                 255

Ser Arg Arg Phe Ala Ala Gln Ser Trp Cys Leu Lys Arg Ile Arg Ala
        260                 265                 270

Val Cys Glu Ala Tyr Gly Thr Thr Val Asn Asp Val Val Thr Ala Met
    275                 280                 285

Cys Ala Ala Ala Leu Arg Thr Tyr Leu Met Asn Gln Asp Ala Leu Pro
290                 295                 300

Glu Lys Pro Leu Val Ala Phe Val Pro Val Ser Leu Arg Arg Asp Asp
305                 310                 315                 320

Ser Ser Gly Gly Asn Gln Val Gly Val Ile Leu Ala Ser Leu His Thr
            325                 330                 335

Asp Val Gln Glu Ala Gly Glu Arg Leu Leu Lys Ile His His Gly Met
        340                 345                 350

Glu Glu Ala Lys Gln Arg Tyr Arg His Met Ser Pro Glu Glu Ile Val
    355                 360                 365

Asn Tyr Thr Ala Leu Thr Leu Ala Pro Ala Ala Phe His Leu Leu Thr
370                 375                 380

Gly Leu Ala Pro Lys Trp Gln Thr Phe Asn Val Val Ile Ser Asn Val
385                 390                 395                 400

Pro Gly Pro Ser Arg Pro Leu Tyr Trp Asn Gly Ala Lys Leu Glu Gly
            405                 410                 415

Met Tyr Pro Val Ser Ile Asp Met Asp Arg Leu Ala Leu Asn Met Thr
        420                 425                 430

Leu Thr Ser Tyr Asn Asp Gln Val Glu Phe Gly Leu Ile Gly Cys Arg
    435                 440                 445

Arg Thr Leu Pro Ser Leu Gln Arg Met Leu Asp Tyr Leu Glu Gln Gly
450                 455                 460

Leu Ala Glu Leu Glu Leu Asn Ala Gly Leu
465                 470

<210> SEQ ID NO 9
<211> LENGTH: 455
<212> TYPE: PRT
<213> ORGANISM: Marinobacter aquaeolei

<400> SEQUENCE: 9

Met Thr Pro Leu Asn Pro Thr Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Gln Leu Arg
        35                  40                  45
```

```
Gln Lys Thr Glu Val Thr Ala Pro Phe Asn Gln Arg Leu Ser Tyr Arg
 50                  55                  60

Leu Gly Gln Pro Val Trp Val Glu Asp Glu His Leu Asp Leu Glu His
 65                  70                  75                  80

His Phe Arg Phe Glu Ala Leu Pro Thr Pro Gly Arg Ile Arg Glu Leu
                 85                  90                  95

Leu Ser Phe Val Ser Ala Glu His Ser His Leu Met Asp Arg Glu Arg
                100                 105                 110

Pro Met Trp Glu Val His Leu Ile Glu Gly Leu Lys Asp Arg Gln Phe
                115                 120                 125

Ala Leu Tyr Thr Lys Val His His Ser Leu Val Asp Gly Val Ser Ala
130                 135                 140

Met Arg Met Ala Thr Arg Met Leu Ser Glu Asn Pro Asp Glu His Gly
145                 150                 155                 160

Met Pro Pro Ile Trp Asp Leu Pro Cys Leu Ser Arg Asp Arg Gly Glu
                165                 170                 175

Ser Asp Gly His Ser Leu Trp Arg Ser Val Thr His Leu Leu Gly Leu
                180                 185                 190

Ser Gly Arg Gln Leu Gly Thr Ile Pro Thr Val Ala Lys Glu Leu Leu
                195                 200                 205

Lys Thr Ile Asn Gln Ala Arg Lys Asp Pro Ala Tyr Asp Ser Ile Phe
210                 215                 220

His Ala Pro Arg Cys Met Leu Asn Gln Lys Ile Thr Gly Ser Arg Arg
225                 230                 235                 240

Phe Ala Ala Gln Ser Trp Cys Leu Lys Arg Ile Arg Ala Val Cys Glu
                245                 250                 255

Ala Tyr Gly Thr Thr Val Asn Asp Val Val Thr Ala Met Cys Ala Ala
                260                 265                 270

Ala Leu Arg Thr Tyr Leu Met Asn Gln Asp Ala Leu Pro Glu Lys Pro
                275                 280                 285

Leu Val Ala Phe Val Pro Val Ser Leu Arg Arg Asp Asp Ser Ser Gly
290                 295                 300

Gly Asn Gln Val Gly Val Ile Leu Ala Ser Leu His Thr Asp Val Gln
305                 310                 315                 320

Glu Ala Gly Glu Arg Leu Leu Lys Ile His His Gly Met Glu Glu Ala
                325                 330                 335

Lys Gln Arg Tyr Arg His Met Ser Pro Glu Glu Ile Val Asn Tyr Thr
                340                 345                 350

Ala Leu Thr Leu Ala Pro Ala Ala Phe His Leu Leu Thr Gly Leu Ala
                355                 360                 365

Pro Lys Trp Gln Thr Phe Asn Val Val Ile Ser Asn Val Pro Gly Pro
370                 375                 380

Ser Arg Pro Leu Tyr Trp Asn Gly Ala Lys Leu Glu Gly Met Tyr Pro
385                 390                 395                 400

Val Ser Ile Asp Met Asp Arg Leu Ala Leu Asn Met Thr Leu Thr Ser
                405                 410                 415

Tyr Asn Asp Gln Val Glu Phe Gly Leu Ile Gly Cys Arg Arg Thr Leu
                420                 425                 430

Pro Ser Leu Gln Arg Met Leu Asp Tyr Leu Glu Gln Gly Leu Ala Glu
                435                 440                 445

Leu Glu Leu Asn Ala Gly Leu
450                 455
```

```
<210> SEQ ID NO 10
<211> LENGTH: 373
<212> TYPE: PRT
<213> ORGANISM: Marinobacter adhaerens

<400> SEQUENCE: 10

Met Ile Lys Ala Val Ile Ser Gly Thr Gly Leu Tyr Thr Pro Pro Ala
1               5                   10                  15

Thr Ile Ser Asn Asp Glu Leu Val Glu Ala Phe Asn Gln Tyr Val Glu
            20                  25                  30

Leu Phe Asn Ala Glu Asn Ala Asp Ala Ile Ala Ser Gly Asp Val Thr
        35                  40                  45

Pro Leu Gln Pro Ser Ser Ser Phe Ile Glu Lys Ala Ser Gly Ile
    50                  55                  60

Lys Arg Arg His Val Ile Asp Lys Asp Gly Ile Leu Asp Pro Asn Arg
65                  70                  75                  80

Met Lys Pro Tyr Ile Pro Asp Arg Ser Asn Glu Glu Pro Ser Val Gln
                85                  90                  95

Cys Asp Met Ala Val Thr Ala Cys Arg Glu Ala Leu Glu Gln Ala Gly
            100                 105                 110

Lys Ser Ala Glu Asp Val Asp Ala Val Ile Val Ala Cys Ser Asn Leu
        115                 120                 125

Gln Arg Ala Tyr Pro Ala Val Ser Ile Glu Val Gln Glu Ala Leu Gly
130                 135                 140

Ile Asp Gly Phe Ala Tyr Asp Met Asn Val Ala Cys Ser Ser Ala Thr
145                 150                 155                 160

Phe Gly Leu Gln Ala Ala Val Asn Ser Val Glu Asn Gly Ser Ala Arg
                165                 170                 175

Ala Val Leu Val Val Ser Pro Glu Ile Cys Ser Gly His Leu Asn Phe
            180                 185                 190

Arg Asp Arg Asp Ser His Phe Ile Phe Gly Asp Ala Cys Thr Ala Ile
        195                 200                 205

Leu Val Glu Arg Glu Glu Asp Thr Arg Glu Gly Gln Gly Phe Glu Ile
210                 215                 220

Leu Gly Thr Ser Leu Lys Thr Lys Phe Ser Asn Asn Ile Arg Asn Asn
225                 230                 235                 240

Phe Gly Phe Leu Asn Arg Ala Asp Glu Ser Gly Val Gly Lys Pro Asp
                245                 250                 255

Lys Leu Phe Val Gln Gln Gly Arg Lys Val Phe Lys Glu Val Ser Pro
            260                 265                 270

Leu Val Ala Glu Thr Ile Gln Lys Gln Leu Gln Ser Leu Ser Leu Ala
        275                 280                 285

Pro Asp Asp Leu Arg Arg Met Trp Leu His Gln Ala Asn Leu Asn Met
290                 295                 300

Asn Gln Leu Ile Ala Arg Lys Val Leu Gly Arg Asp Ala Thr Glu Glu
305                 310                 315                 320

Glu Ala Pro Val Ile Leu Asp Glu Tyr Ala Asn Thr Ser Ser Ala Gly
                325                 330                 335

Ser Ile Ile Ala Phe His Lys Asn Lys Asp Asp Leu Val Ser Gly Asp
            340                 345                 350

Leu Gly Val Ile Cys Ser Phe Gly Ala Gly Tyr Ser Ile Gly Ser Val
        355                 360                 365

Val Val Arg Arg Arg
    370
```

<210> SEQ ID NO 11
<211> LENGTH: 372
<212> TYPE: PRT
<213> ORGANISM: Alishewanella agri

<400> SEQUENCE: 11

```
Met Gln Gln Val Val Ile Ser Gly Ser Gly Leu Phe Thr Pro Gln His
1               5                   10                  15

Arg Ile Ser Asn Glu Glu Leu Val Gln Ser Tyr Asn Gln Tyr Val Asp
            20                  25                  30

Gln Phe Asn Glu Glu His Ala Ala Ile Ala Ala Gly Glu Ile Glu
        35                  40                  45

Ala Leu Glu Tyr Ser Ser Thr Glu Phe Ile Glu Lys Ala Ser Gly Ile
50                  55                  60

Lys Ala Arg His Val Leu Tyr Lys Asp Gly Ile Leu Asp Pro Lys Ile
65                  70                  75                  80

Met His Pro Val Phe Arg Lys Arg Gly Glu Asp Glu Leu Pro Glu Met
                85                  90                  95

Val Glu Met Ala Val Gln Ala Ala Thr Gln Ala Leu Ala Gln Ala Asn
            100                 105                 110

Lys Thr Ala Ala Asp Ile Asp Leu Ile Ile Cys Ala Ala Ser Asn Met
        115                 120                 125

Gln Arg Pro Tyr Pro Ala Leu Ser Val Glu Leu Gln Gln Ala Leu Gly
    130                 135                 140

Ala Gly Gly Tyr Ala Phe Asp Met Asn Val Ala Cys Ser Ser Ala Thr
145                 150                 155                 160

Phe Ala Ile Ser Asn Ala Val Asn Ala Ile Arg Gly Gly Thr Ala Lys
                165                 170                 175

Val Val Leu Val Val Asn Pro Glu Phe Ala Ser Pro Gln Val Asp Tyr
            180                 185                 190

Arg Ser Arg Asp Ser His Phe Ile Phe Gly Asp Val Cys Thr Ala Thr
        195                 200                 205

Ile Ile Glu Ala Glu Ser Ser Cys Ser Ser Gln Gln Ala Phe Arg Ile
    210                 215                 220

Leu Gly Met Arg Leu Lys Thr Thr Phe Ser Asn Asn Ile Arg Cys Asp
225                 230                 235                 240

Ile Gly Tyr Thr Glu His Cys Phe Thr Glu Gln Asp Pro Lys Ala Pro
                245                 250                 255

Phe Phe Lys Gln Gln Gly Arg Lys Val Phe Lys Glu Leu Leu Pro Ile
            260                 265                 270

Val Ala Asp Val Ile Gln Asp Glu Met Ala Ala Gln Asn Leu Ala Pro
        275                 280                 285

Asp Asp Leu Lys Arg Leu Trp Leu His Gln Ala Asn Ile Asn Met Asn
    290                 295                 300

Ile Phe Ala Ala Lys Lys Ile Leu Gly Arg Asp Pro Leu Pro Glu Glu
305                 310                 315                 320

Ala Pro Leu Val Leu Asp Thr Tyr Ala Asn Thr Ala Ser Ala Gly Ser
                325                 330                 335

Ile Ile Ala Phe His Lys Tyr Gln Gln Gly Leu Val Ser Gly Asp Lys
            340                 345                 350

Ala Ile Leu Cys Ser Phe Gly Ala Gly Tyr Ser Val Gly Cys Val Val
        355                 360                 365

Leu Glu Lys Cys
```

370

<210> SEQ ID NO 12
<211> LENGTH: 368
<212> TYPE: PRT
<213> ORGANISM: Acinetobacter sp.

<400> SEQUENCE: 12

```
Met Gly Ile Arg Ile Thr Gly Thr Gly Leu Phe His Pro Thr Glu Ser
1               5                   10                  15

Ile Ser Asn Glu Glu Leu Val Glu Ser Leu Asn Ala Tyr Val Glu Gln
            20                  25                  30

Phe Asn Gln Glu Asn Ala Glu Gln Ile Ala Ala Gly Glu Ile Glu Ala
        35                  40                  45

Leu Arg Gly Ser Ser Pro Glu Phe Ile Glu Lys Ala Ser Gly Ile Gln
    50                  55                  60

Arg Arg Tyr Val Val Glu Lys Ser Gly Ile Leu Asp Pro Lys Arg Leu
65                  70                  75                  80

Arg Pro Arg Leu Gln Glu Arg Ser Asn Asp Glu Leu Ser Leu Gln Ala
                85                  90                  95

Glu Trp Gly Val Ile Ala Ala Lys Gln Ala Met Glu Asn Ala Gly Val
            100                 105                 110

Thr Ala Glu Asp Ile Asp Val Val Ile Leu Ala Cys Ser Asn Met Gln
        115                 120                 125

Arg Ala Tyr Pro Ala Val Ala Ile Glu Ile Gln Ser Ala Leu Gly Ile
    130                 135                 140

Gln Gly Tyr Ala Tyr Asp Met Asn Val Ala Cys Ser Ala Ala Thr Phe
145                 150                 155                 160

Gly Leu Lys Gln Ala Tyr Asp Ala Val Lys Cys Gly Ala Arg Arg Val
                165                 170                 175

Leu Leu Leu Asn Val Glu Ile Thr Ser Gly His Leu Asp Tyr Arg Thr
            180                 185                 190

Arg Asp Ala His Phe Ile Phe Gly Asp Val Ala Thr Ala Ser Ile Ile
        195                 200                 205

Glu Glu Thr Glu Thr Lys Ser Gly Tyr Glu Ile Leu Asp Ile His Leu
    210                 215                 220

Phe Thr Gln Phe Ser Asn Asn Ile Arg Asn Asn Phe Gly Phe Leu Asn
225                 230                 235                 240

Arg Ser Glu Asp Ala Val Val Asp Asp Lys Leu Phe Arg Gln Asp Gly
                245                 250                 255

Arg Lys Val Phe Lys Glu Val Cys Pro Leu Val Ala Lys Ile Ile Thr
            260                 265                 270

Ala Gln Leu Glu Lys Leu Glu Leu Thr Pro Glu Gln Val Lys Arg Phe
        275                 280                 285

Trp Leu His Gln Ala Asn Ala Asn Met Asn Glu Leu Ile Leu Lys Leu
    290                 295                 300

Val Val Gly Lys Glu Ala Asp Leu Glu Arg Ala Pro Ile Ile Leu Asp
305                 310                 315                 320

Glu Phe Ala Asn Thr Ser Ser Ala Gly Val Ile Ile Ala Met His Arg
                325                 330                 335

Thr Gly Glu Gln Val Asn Asn Gly Glu Tyr Ala Val Ile Ser Ser Phe
            340                 345                 350

Gly Ala Gly Tyr Ser Val Gly Ser Ile Ile Val Gln Lys His Ile Ala
        355                 360                 365
```

<210> SEQ ID NO 13
<211> LENGTH: 373
<212> TYPE: PRT
<213> ORGANISM: Ralstonia solanacearum

<400> SEQUENCE: 13

```
Met His Asp Val Val Ile Ser Gly Thr Gly Leu Trp Val Ala Pro Glu
1               5                   10                  15

Val Ile Thr Asn Glu Glu Leu Val Ala Ser Phe Asn Ala Tyr Ala Arg
            20                  25                  30

His Tyr Asn Glu Ala Asn Ala Thr Ala Ile Ala Ala Gly Thr Leu Ala
        35                  40                  45

Ala Val Ala Glu Ser Ser Val Glu Phe Ile Glu Lys Ala Ser Gly Ile
    50                  55                  60

Arg Gln Arg Tyr Val Ile Asp Lys Ala Gly Val Leu Asp Pro Ala Arg
65                  70                  75                  80

Met Arg Pro Arg Leu Ala Pro Arg Gly Asp Asp Ala Leu Ser Leu Gln
                85                  90                  95

Ala Glu Ile Gly Val Ala Ala Ala Arg Glu Ala Leu Ala Ala Ala Gly
            100                 105                 110

Arg Asp Ala Gly Asp Ile Asp Met Leu Ile Cys Ser Ala Ala Asn Met
        115                 120                 125

Gln Arg Pro Tyr Pro Ala Met Gly Ile Glu Ile Gln Asn Ala Leu Gly
    130                 135                 140

Ala Asp Gly Tyr Ala Phe Asp Met Asn Val Ala Cys Ser Ser Ala Thr
145                 150                 155                 160

Phe Gly Leu Glu Gln Ala Ile Asn Ala Val Arg Thr Gly Ser Ala Arg
                165                 170                 175

Val Ala Leu Met Val Asn Pro Glu Ile Thr Ser Gly His Leu Ala Trp
            180                 185                 190

Lys Asp Arg Asp Cys His Phe Ile Phe Gly Asp Val Cys Thr Ala Val
        195                 200                 205

Val Val Glu Arg Ala Asp Asp Ala Arg Ala Pro Asp Gln Trp Gln Val
    210                 215                 220

Leu Gly Thr Arg Met Ala Thr Arg Phe Ser Asn Ser Ile Arg Asn Asn
225                 230                 235                 240

Ala Gly Phe Leu Ser Arg Ser Glu Asp Arg Asp Pro Asp Asp Arg Asp
                245                 250                 255

Gln Leu Phe Arg Gln Glu Gly Arg Lys Val Phe Lys Glu Val Cys Pro
            260                 265                 270

Met Ala Ala Glu His Ile Ala Gly His Leu Gln Ser Leu Gly His Ala
        275                 280                 285

Pro Ala Asp Val Arg Arg Phe Trp Leu His Gln Ala Asn Leu Gly Met
    290                 295                 300

Asn Gln Leu Ile Gly Lys Arg Leu Leu Gly Arg Asp Ala Ser Ala Asp
305                 310                 315                 320

Glu Ala Pro Val Ile Leu Asp Glu Phe Ala Asn Thr Ala Ser Ala Gly
                325                 330                 335

Ser Ile Ile Ala Phe His Arg His Arg Ala Asp Leu Gln Pro Gly Asp
            340                 345                 350

Leu Gly Leu Ile Cys Ser Phe Gly Ala Gly Tyr Ser Ile Gly Ser Val
        355                 360                 365

Ala Val Arg Lys Arg
    370
```

<210> SEQ ID NO 14
<211> LENGTH: 261
<212> TYPE: PRT
<213> ORGANISM: Clostridium acetobutylicum

<400> SEQUENCE: 14

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 15
<211> LENGTH: 282
<212> TYPE: PRT
<213> ORGANISM: Clostridium acetobutylicum

<400> SEQUENCE: 15

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
            85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
            115                 120                 125

Lys Arg Pro Asp Lys Val Ile Gly Met His Phe Phe Asn Pro Ala Pro
130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
                180                 185                 190

Pro Met Ile Asn Glu Ala Val Gly Ile Leu Ala Glu Gly Ile Ala Ser
            195                 200                 205

Val Glu Asp Ile Asp Lys Ala Met Lys Leu Gly Ala Asn His Pro Met
210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
            275                 280

<210> SEQ ID NO 16
<211> LENGTH: 4334
<212> TYPE: DNA
<213> ORGANISM: Escherichia coli

<400> SEQUENCE: 16
ctgatggaca ggctgcgcct gcccacgagc ttgaccacag ggattgccca ccggctaccc      60
agccttcgac cacatacccca ccggctccaa ctgcgcggcc tgcggccttg ccccatcaat    120
ttttttaatt ttctctgggg aaaagcctcc ggcctgcggc ctgcgcgctt cgcttgccgg    180
ttggacacca agtggaaggc gggtcaaggc tcgcgcagcg accgcgcagc ggcttggcct    240
tgacgcgcct ggaacgaccc aagcctatgc gagtgggggc agtcgaaggc gaagcccgcc    300
cgcctgcccc ccgagcctca cggcggcgag tgcgggggtt ccaagggggc agcgccacct    360
tgggcaaggc cgaaggccgc gcagtcgatc aacaagcccc ggaggggcca cttttttgccg    420 gagggggagc cgcgccgaag cgtgggggga accccgcagg ggtgcccttc tttgggcacc    480
aaagaactag atatagggcg aaatgcgaaa gacttaaaaa tcaacaactt aaaaaagggg    540
ggtacgcaac agctcattgc ggcacccccc gcaatagctc attgcgtagg ttaagaaaaa    600
tctgtaattg actgccactt ttacgcaacg cataattgtt gtcgcgctgc cgaaaagttg    660
cagctgattg cgcatggtgc cgcaaccgtg cggcaccctca ccgcatggag ataagcatgg    720
ccacgcagtc cagagaaatc ggcattcaag ccaagaacaa gcccgttcac tgggtgcaaa    780
cggaacgcaa agcgcatgag gcgtgggccg ggcttattgc gaggaaaccc acggcggcaa    840

```
tgctgctgca tcacctcgtg gcgcagatgg gccaccagaa cgccgtggtg gtcagccaga    900
agacactttc caagctcatc ggacgttctt tgcggacggt ccaatacgca gtcaaggact    960
tggtggccga gcgctggatc tccgtcgtga agctcaacgg ccccggcacc gtgtcggcct   1020
acgtggtcaa tgaccgcgtg gcgtggggcc agccccgcga ccagttgcgc ctgtcggtgt   1080
tcagtgccgc cgtggtggtt gatcacgacg accaggacga atcgctgttg gggcatggcg   1140
acctgcgccg catcccgacc ctgtatccgg gcgagcagca actaccgacc ggccccggcg   1200
aggagccgcc cagccagccc ggcattccgg gcatggaacc agacctgcca gccttgaccg   1260
aaacggagga tgggaacgg cgcgggcagc agcgcctgcc gatgcccgat gagccgtgtt   1320
ttctggacga tggcgagccg ttggagccgc cgacacgggt cacgctgccg cgccggtagt   1380
acgtacccgg aattgccagc tggggcgccc tctggtaagg ttgggaagcc ctgcaaagta   1440
aactggatgg ctttcttgcc gccaaggatc tgatggcgca ggggatcaag ctctgatcaa   1500
gagacaggat gaggatcgtt tcgatgaagc agcgtattac agtgacagtt gacagcgaca   1560
gctatcagtt gctcaaggca tatgatgtca atatctccgg tctggtaagc acaaccatgc   1620
agaatgaagc ccgtcgtctg cgtgccgaac gctggaaagc ggaaaatcag gaagggatgg   1680
ctgaggtcgc ccggtttatt gaaatgaacg gctcttttgc tgacgagaac agggactggt   1740
gaaatgcagt ttaaggttta cacctataaa agagagagcc gttatcgtct gtttgtggat   1800
gtacagagcg atattattga cacgcccggg cgacggatgg tgatccccct ggccagtgca   1860
cgtctgctgt cagataaagt ctcccgtgaa ctttacccgg tggtgcatat cggggatgaa   1920
agctggcgca tgatgaccac cgatatggcc agtgtgccgg tctccgttat cggggaagaa   1980
gtggctgatc tcagccaccg cgaaaatgac atcaaaaacg ccattaacct gatgttctgg   2040
ggaatataaa tcctagacga attctctagt agaggttcca actttcacca taatgaaata   2100
agatcactac cgggcgtatt ttttgagtta tcgagatttt caggagctaa ggaagctaaa   2160
atggagaaaa aaatcactgg atataccacc gttgatatat cccaatggca tcgtaaagaa   2220
cattttgagg catttcagtc agttgctcaa tgtacctata accagaccgt tcagctggat   2280
attacggcct ttttaaagac cgtaaagaaa aataagcaca gtttatcc ggcctttatt    2340 cacattcttg cccgcctgat gaatgctcat ccggaattcc gtatggcaat gaaagacggt   2400
gagctggtga tatgggatag tgttcaccct tgttacaccg ttttccatga gcaaactgaa   2460
acgttttcat cgctctggag tgaataccac gacgatttcc ggcagtttct acacatatat   2520
tcgcaagatg tggcgtgtta cggtgaaaac ctggcctatt tccctaaagg gtttattgag   2580
aatatgtttt tcgtctcagc caatccctgg gtgagtttca ccagttttga tttaaacgtg   2640
gccaatatgg acaacttctt cgcccccgtt ttcaccatgg gcaaatatta tacgcaaggc   2700
gacaaggtgc tgatgccgct ggcgattcag gttcatcatg ccgtttgtga tggcttccat   2760
gtcggcagaa tgcttaatga attacaacag tactgcgatg agtggcaggg cggggcgtaa   2820
agatctggat cccccctcaag tcaaaagcct ccggtcggag gcttttgact ttctgctatg   2880
gaggtcaggt atgatttaaa tggtcagtat tgagcgatat ctagagaatt cgtcaacgaa   2940
ttcaagcttg atatcattca ggacgagcct cagactccag cgtaactgga ctgaaaacaa   3000
actaaagcgc ccttgtggcg ctttagtttt gttccgctca tgataataat ggtttcttag   3060
acgtcaggtg gcacttttcg gggaaatgtg cgcgcccgcg ttcctgctgg cgctgggcct   3120
gtttctggcg ctggacttcc cgctgttccg tcagcagctt ttcgcccacg ccttgatgaa   3180
tcgcggcggc cttggcctgc atatcccgat tcaacggccc cagggcgtcc agaacgggct   3240
```

```
tcaggcgctc ccgaaggtct cgggccgtct cttgggcttg atcggccttc ttgcgcatct      3300
cacgcgctcc tgcggcggcc tgtagggcag gctcataccc ctgccgaacc gcttttgtca      3360
gccggtcggc cacggcttcc ggcgtctcaa cgcgctttga gattcccagc ttttcggcca      3420
atccctgcgg tgcataggcg cgtggctcga ccgcttgcgg gctgatggtg acgtggccca      3480
ctggtggccg ctccagggcc tcgtagaacg cctgaatgcg cgtgtgacgt gccttgctgc      3540
cctcgatgcc ccgttgcagc cctagatcgg ccacagcggc cgcaaacgtg gtctggtcgc      3600
gggtcatctg cgctttgttg ccgatgaact ccttggccga cagcctgccg tcctgcgtca      3660
gcggcaccac gaacgcggtc atgtgcgggc tggtttcgtc acggtggatg ctggccgtca      3720
cgatgcgatc cgccccgtac ttgtccgcca gccacttgtg cgccttctcg aagaacgccg      3780
cctgctgttc ttggctggcc gacttccacc attccgggct ggccgtcatg acgtactcga      3840
ccgccaacac agcgtccttg cgccgcttct ctggcagcaa ctcgcgcagt cggcccatcg      3900
cttcatcggt gctgctggcc gcccagtgct cgttctctgg cgtcctgctg gcgtcagcgt      3960
tgggcgtctc gcgctcgcgg taggcgtgct tgagactggc cgccacgttg cccattttcg      4020
ccagcttctt gcatcgcatg atcgcgtatg ccgccatgcc tgccctccc ttttggtgtc      4080 caaccggctc gacgggggca gcgcaaggcg gtgcctccgg cgggccactc aatgcttgag      4140
tatactcact agactttgct tcgcaaagtc gtgaccgcct acggcggctg cggcgcccta      4200
cgggcttgct ctccgggctt cgccctgcgc ggtcgctgcg ctcccttgcc agcccgtgga      4260
tatgtggacg atggccgcga gcggccaccg gctggctcgc ttcgctcggc ccgtggacaa      4320
ccctgctgga caag                                                       4334

<210> SEQ ID NO 17
<211> LENGTH: 5024
<212> TYPE: DNA
<213> ORGANISM: Escherichia coli

<400> SEQUENCE: 17
caaaaaaccc ctcaagaccc gtttagaggc cccaagggt tatgctagtt attgctcagc         60
ggtggcagca gcctaggtta attaagctgc gctagtagac gagtccatgt gctggcgttc        120
aaatttcgca gcagcggttt cttaccaga ctcgaaaatt caggagtcgt ggttgaccag         180
cggctgcagt tgcttggcca tccagtcggc gatgaacggc tgcgcgtcgc ggttcgggtg        240
gatgccgtcg tcctgcatcc actgcggctt caggtagact cctccatga agaacggcag         300 cagcggcacg tcgaattcct tggccagctt cgggtagatc gcggagaagg cctcgttgta        360
gcgacggccg tagttcgccg gcaggcggat ctgcatcagc agcggctcgg cgttcgcggc        420
cttcacgtcc tgcaggatct ggcgcagcgt ctgttcggtc tgctgcggct ggaagccgcg        480
caggccgtcg ttgccgccca gctcgaccag cacccagcgc ggctggtgct gcttcagcag        540
cgccggcagg cgggccaggc cctgctggct cgtgtcgccg ctgatcgagg cgttgaccac        600
cgaggtcttg gactgccact tgtcgttcag cagcgccggc cacgccgccg acgccgacat        660
gcggtagccc gccgacaggg agtcgcccag gatcagcagg gtgtccgccg ccatggtata        720
tctccttatt aaagttaaac aaaattattt ctacagggga attgttatcc gctcacaatt        780
cccctatagt gagtcgtatt aatttcctaa tgcaggagtc gatcattcag gacgagcctc        840
agactccagc gtaactggac tgaaaacaaa ctaaagcgcc cttgtggcgc tttagttttg        900
ttccgctcat gataataatg gtttcttaga cgtcaggtgg cacttttcgg ggaaatgtgc        960
```

-continued

```
gcgcccgcgt tcctgctggc gctgggcctg tttctggcgc tggacttccc gctgttccgt    1020
cagcagcttt tcgcccacgg ccttgatgat cgcggcggcc ttggcctgca tatcccgatt    1080
caacggcccc agggcgtcca gaacgggctt caggcgctcc cgaaggtctc gggccgtctc    1140
ttgggcttga tcggccttct tgcgcatctc acgcgctcct cgggcggcct gtagggcagg    1200
ctcatacccc tgccgaaccg cttttgtcag ccggtcggcc acggcttccg gcgtctcaac    1260
gcgctttgag attcccagct tttcggccaa tccctgcgt  gcataggcgc gtggctcgac    1320
cgcttgcggg ctgatggtga cgtggcccac tggtggccgc tccagggcct cgtagaacgc    1380
ctgaatgcgc gtgtgacgtg ccttgctgcc ctcgatgccc cgttgcagcc ctagatcggc    1440
cacagcggcc gcaaacgtgg tctggtcgcg ggtcatctgc gctttgttgc cgatgaactc    1500
cttggccgac agcctgccgt cctgcgtcag cggcaccacg aacgcggtca tgtgcgggct    1560
ggtttcgtca cggtggatgc tggccgtcac gatgcgatcc gccccgtact tgtccgccag    1620
ccacttgtgc gccttctcga gaacgccgc  ctgctgttct tggctggccg acttccacca    1680
ttccgggctg gccgtcatga cgtactcgac cgccaacaca gcgtccttgc gccgcttctc    1740
tggcagcaac tcgcgcagtc ggcccatcgc ttcatcggtg ctgctggccg cccagtgctc    1800
gttctctggc gtcctgctgg cgtcagcgtt gggcgtctcg cgctcgcggt aggcgtgctt    1860
gagactggcc gccacgttgc ccattttcgc cagcttcttg catcgcatga tcgcgtatgc    1920
cgccatgcct gccctccct  tttggtgtcc aaccggctcg acggggcag  cgcaaggcgg    1980
tgcctccggc gggccactca atgcttgagt atactcacta gactttgctt cgcaaagtcg    2040
tgaccgccta cggcggctgc ggcgccctac gggcttgctc tccgggcttc gccctgcgcg    2100
gtcgctgcgc tcccttgcca gcccgtggat atgtggacga tggccgcgag cggccaccgg    2160
ctggctcgct tcgctcggcc cgtggacaac cctgctggac aagctgatgg acaggctgcg    2220
cctgcccacg agcttgacca cagggattgc ccaccggcta cccagccttc gaccacatac    2280
ccaccggctc caactgcgcg gcctgcggcc ttgccccatc aattttttta attttctctg    2340
gggaaaagcc tccggcctgc ggcctgcgcg cttcgcttgc cggttggaca ccaagtggaa    2400
ggcgggtcaa ggctcgcgca cgaccgcgc  agcggcttgg ccttgacgcg cctggaacga    2460
cccaagccta tgcgagtggg ggcagtcgaa ggcgaagccc gcccgcctgc ccccgagcc    2520
tcacggcggc gagtgcgggg gttccaaggg ggcagcgcca ccttgggcaa ggccgaaggc    2580
cgcgcagtcg atcaacaagc cccggagggg ccacttttg  ccggaggggg agccgcgccg    2640
aaggcgtggg ggaaccccgc aggggtgccc ttctttgggc accaaagaac tagatatagg    2700
gcgaaatgcg aaagacttaa aaatcaacaa cttaaaaaag ggggtacgc  aacagctcat    2760
tgcggcaccc cccgcaatag ctcattgcgt aggttaaaga aaatctgtaa ttgactgcca    2820
cttttacgca acgcataatt gttgtcgcgc tgccgaaaag ttgcagctga ttgcgcatgg    2880
tgccgcaacc gtgcggcacc ctaccgcatg gagataagca tggccacgca gtccagagaa    2940
atcggcattc aagccaagaa caagcccggt cactgggtgc aaacggaacg caaagcgcat    3000
gaggcgtggg ccgggcttat tgcgaggaaa cccacggcgg caatgctgct gcatcacctc    3060
gtggcgcaga tgggccacca gaacgccgtg gtggtcagcc agaagacact tccaagctc    3120
atcggacgtt ctttgcggac ggtccaatac gcagtcaagg acttggtggc cgagcgctgg    3180
atctccgtcg tgaagctcaa cggccccggc accgtgtcgg cctacgtggt caatgaccgc    3240
gtggcgtggg gccagcccg  cgaccagttg cgcctgtcgg tgttcagtgc cgccgtggtg    3300
gttgatcacg acgaccagga cgaatcgctg ttggggcatg gcgacctgcg ccgcatcccg    3360
```

```
accctgtatc cgggcgagca gcaactaccg accggccccg gcgaggagcc gcccagccag    3420
cccggcattc cggcatgga accagacctg ccagccttga ccgaaacgga ggaatgggaa    3480
cggcgcgggc agcagcgcct gccgatgccc gatgagccgt gttttctgga cgatggcgag    3540
ccgttggagc cgccgacacg ggtcacgctg ccgcgccggt agtacgtacc cggaattgcc    3600
agctggggcg ccctctggta aggttgggaa gccctgcaaa gtaaactgga tggctttctt    3660
gccgccaagg atctgatggc gcaggggatc aagctctgat caagagacag gatgaggatc    3720
gtttcgatga agcagcgtat tacagtgaca gttgacagcg acagctatca gttgctcaag    3780
gcatatgatg tcaatatctc cggtctggta agcacaacca tgcagaatga agcccgtcgt    3840
ctgcgtgccg aacgctggaa agcggaaaat caggaaggga tggctgaggt cgcccggttt    3900
attgaaatga acggctcttt tgctgacgag aacaggggact ggtgaaatgc agtttaaggt    3960
ttacacctat aaaagagaga gccgttatcg tctgtttgtg gatgtacaga gcgatattat    4020
tgacacgccc gggcgacgga tggtgatccc cctggccagt gcacgtctgc tgtcagataa    4080
agtctcccgt gaactttacc cggtggtgca tatcggggat gaaagctggc gcatgatgac    4140
caccgatatg gccagtgtgc cggtctccgt tatcggggaa gaagtggctg atctcagcca    4200
ccgcgaaaat gacatcaaaa acgccattaa cctgatgttc tggggaatat aaatcctaga    4260
cgaattctct agtagaggtt ccaactttca ccataatgaa ataagatcac taccgggcgt    4320 atttttttgag ttatcgagat tttcaggagc taaggaagct aaaatggaga aaaaaatcac    4380
tggatatacc accgttgata tatcccaatg gcatcgtaaa gaacattttg aggcatttca    4440
gtcagttgct caatgtacct ataaccagac cgttcagctg gatattacgg cctttttaaa    4500
gaccgtaaag aaaaataagc acaagtttta tccggccttt attcacattc ttgcccgcct    4560
gatgaatgct catccggaat tccgtatggc aatgaaagac ggtgagctgg tgatatggga    4620
tagtgttcac ccttgttaca ccgttttcca tgagcaaaact gaaacgtttt catcgctctg    4680
gagtgaatac cacgacgatt tccggcagtt tctacacata tattcgcaag atgtggcgtg    4740
ttacggtgaa aacctggcct atttccctaa agggtttatt gagaatatgt ttttcgtctc    4800
agccaatccc tgggtgagtt tcaccagttt tgatttaaac gtggccaata tggacaactt    4860
cttcgccccc gttttcacca tgggcaaata ttatacgcaa ggcgacaagg tgctgatgcc    4920
gctggcgatt caggttcatc atgccgtttg tgatggcttc catgtcggca gaatgcttaa    4980
tgaattacaa cagtactgcg atgagtggca gggcggggcg taaa                    5024
```

<210> SEQ ID NO 18
<211> LENGTH: 8268
<212> TYPE: DNA
<213> ORGANISM: Escherichia coli

<400> SEQUENCE: 18

```
ccttgccagc ccgtggatat gtggacgatg gccgcgagcg gccaccggct ggctcgcttc      60
gctcggcccg tggacaaccc tgctggacaa gctgatggac aggctgcgcc tgcccacgag     120
cttgaccaca gggattgccc accggctacc cagccttcga ccacataccc accggctcca     180
actgcgcggc ctgcggcctt gccccatcaa tttttttaat tttctctggg gaaaagcctc     240
cggcctgcgg cctgcgcgct tcgcttgccg gttggacacc aagtggaagg cgggtcaagg     300
ctcgcgcagc gaccgcgcag cggccttggcc ttgacgcgcc tggaacgacc caagcctatg     360
cgagtggggg cagtcgaagg cgaagcccgc ccgcctgccc cccgagcctc acggcggcga     420
```

```
gtgcggggt  tccaagggg   cagcgccacc  ttgggcaagg  ccgaaggccg  cgcagtcgat   480
caacaagccc  cggagggcc   acttttgcc   ggagggggag  ccgcgccgaa  ggcgtggggg   540
aaccccgcag  gggtgcccctt  ctttgggcac  caaagaacta  gatatagggc  gaaatgcgaa   600
agacttaaaa  atcaacaact  taaaaaaggg  gggtacgcaa  cagctcattg  cggcaccccc   660
cgcaatagct  cattgcgtag  gttaaagaaa  atctgtaatt  gactgccact  tttacgcaac   720
gcataattgt  tgtcgcgctg  ccgaaaagtt  gcagctgatt  gcgcatggtg  ccgcaaccgt   780
gcggcaccct  accgcatgga  gataagcatg  gccacgcagt  ccagagaaat  cggcattcaa   840
gccaagaaca  agcccggtca  ctgggtgcaa  acggaacgca  aagcgcatga  ggcgtgggcc   900
gggcttattg  cgaggaaacc  cacggcggca  atgctgctgc  atcacctcgt  ggcgcagatg   960
ggccaccaga  acgccgtggt  ggtcagccag  aagacactt   ccaagctcat  cggacgttct  1020
ttgcggacgg  tccaatacgc  agtcaaggac  ttggtggccg  agcgctggat  ctccgtcgtg  1080
aagctcaacg  ccccggcac   cgtgtcggcc  tacgtggtca  atgaccgcgt  ggcgtggggc  1140
cagccccgcg  accagttgcg  cctgtcggtg  ttcagtgccg  ccgtggtggt  tgatcacgac  1200
gaccaggacg  aatcgctgtt  ggggcatggc  gacctgcgcc  gcatcccgac  cctgtatccg  1260
ggcgagcagc  aactaccgac  cggccccggc  gaggagccgc  ccagccagcc  cggcattccg  1320
ggcatggaac  cagacctgcc  agccttgacc  gaaacggagg  aatgggaacg  cgcgggcag   1380 cagcgcctgc  cgatgcccga  tgagccgtgt  tttctggacg  atggcgagcc  gttggagccg  1440
ccgacacggg  tcacgctgcc  gcgccggtag  tacgtacccg  gaattgccag  ctggggcgcc  1500
ctctggtaag  gttgggaagc  cctgcaaagt  aaactggatg  gctttcttgc  cgccaaggat  1560
ctgatggcgc  aggggatcaa  gctctgatca  agagacagga  tgaggatcgt  ttcgatgaag  1620
cagcgtatta  cagtgacagt  tgacagcgac  agctatcagt  tgctcaaggc  atatgatgtc  1680
aatatctccg  gtctggtaag  cacaaccatg  cagaatgaag  cccgtcgtct  gcgtgccgaa  1740
cgctggaaag  cggaaaatca  ggaagggatg  gctgaggtcg  cccggttat   tgaaatgaac  1800 ggctcttttg  ctgacgagaa  cagggactgg  tgaaatgcag  tttaaggttt  acacctataa  1860
aagagagagc  cgttatcgtc  tgtttgtgga  tgtacagagc  gatattattg  acacgcccgg  1920
gcgacggatg  gtgatccccc  tggccagtgc  acgtctgctg  tcagataaag  tctcccgtga  1980
actttacccg  gtggtgcata  tcggggatga  aagctggcgc  atgatgacca  ccgatatggc  2040
cagtgtgccg  gtctccgtta  tcggggaaga  agtggctgat  ctcagccacc  gcgaaaatga  2100
catcaaaaac  gccattaacc  tgatgttctg  gggaatataa  atcctagacg  aattctctag  2160
tagaggttcc  aactttcacc  ataatgaaat  aagatcacta  ccgggcgtat  tttttgagtt  2220
atcgagattt  tcaggagcta  aggaagctaa  aatggagaaa  aaaatcactg  gatataccac  2280
cgttgatata  tcccaatggc  atcgtaaaga  acatttgag   gcatttcagt  cagttgctca  2340
atgtacctat  aaccagaccg  ttcagctgga  tattacggcc  tttttaaaga  ccgtaaagaa  2400
aaataagcac  aagtttatc   cggcctttat  tcacattctt  gcccgcctga  tgaatgctca  2460
tccggaattc  cgtatggcaa  tgaaagacgg  tgagctggtg  atatgggata  gtgttcaccc  2520
ttgttacacc  gttttccatg  agcaaactga  aacgttttca  tcgctctgga  gtgaatacca  2580
cgacgatttc  cggcagtttc  tacacatata  ttcgcaagat  gtggcgtgtt  acggtgaaaa  2640
cctggcctat  ttccctaaag  ggtttattga  gaatatgttt  ttcgtctcag  ccaatccctg  2700
ggtgagtttc  accagttttg  atttaaacgt  ggccaatatg  gacaacttct  tcgccccccgt  2760 tttcaccatg  ggcaaatatt  atacgcaagg  cgacaaggtg  ctgatgccgc  tggcgattca  2820
```

-continued

```
ggttcatcat gccgtttgtg atggcttcca tgtcggcaga atgcttaatg aattacaaca    2880
gtactgcgat gagtggcagg gcggggcgta aaaatccct tatgcgactc ctgcattagg     2940
aaattaatac gactcactat agggaattg tgagcggata caattcccc tgtagaaata      3000 atttttgttta actttaataa ggagatatac catgacggat gtccgctttc gtatcattgg   3060
cacgggcgct tacgtcccgg aacgcattgt cagcaacgac gaagtcggcg caccggctgg    3120
tgtggatgac gattggatta cgcgtaaaac cggtatccgc cagcgtcgct gggcggccga    3180
cgatcaagca acgagcgatc tggctaccgc agctggtcgt gcagcactga aagcagctgg    3240
cattacgccg gaacagctga ccgtcatcgc agtggctacc tctacgccgg accgtccgca    3300
gccgccgacc gcggcctatg ttcaacatca cctgggtgca accggcacgg cagcttttga    3360
tgttaacgct gtgtgcagcg gtacggtttt cgcgctgagc tctgttgccg gcaccctggt    3420
ctatcgtggc ggttacgcac tggtcattgg tgctgatctg tactcacgta tcctgaatcc    3480
ggcggaccgc aaaaccgtgg ttctgttcgg cgatggtgcg ggcgcgatgg tgctgggccc    3540
gaccagcacc ggcaccggtc cgattgtgcg tcgcgttgca ctgcatacgt ttggcggtct    3600
gaccgatctg atccgtgttc cggccggcgg ttcccgccag ccgctggaca ccgatggtct    3660
ggacgcaggc ctgcaatatt ttgcgatgga tggccgcgaa gtccgtcgct tcgtgaccga    3720
acatctgccg cagctgatta aaggttttct gcacgaagcg ggcgtggatg cggcggatat    3780
tagccatttc gtgccgcacc aagccaacgg tgtgatgctg acgaagtttt ttggcgaact    3840
gcatctgccg cgtgcaacca tgcaccgtac ggtggaaacc tacggtaata cgggcgcagc    3900
tagtattccg atcacgatgg atgcggccgt tcgtgcaggt tccttccgtc cgggcgaact    3960
ggttctgctg gcgggctttg gcggcggtat ggcggcttcg tttgctctga ttgaatggtg    4020
acctaatgca ggctgcaggc ggatacgagg aggaataaac catgaaaaag gtatgtgtta    4080
taggtgcagg tactatgggt tcaggaattg ctcaggcatt tgcagctaaa ggatttgaag    4140
tagtattaag agatattaaa gatgaatttg ttgatagagg attagatttt atcaataaaa    4200
atctttctaa attagttaaa aaaggaaaga tagaagaagc tactaaagtt gaaatcttaa    4260
ctagaatttc cggaacagtt gaccttaata tggcagctga ttgcgattta gttatagaag    4320
cagctgttga agaatggat attaaaaagc agattttgc tgacttagac aatatatgca      4380
agccagaaac aattcttgca tcaaatacat catcactttc aataacagaa gtggcatcag    4440
caactaaaag acctgataag gttataggta tgcatttctt taatccagct cctgttatga    4500
agcttgtaga ggtaataaga ggaatagcta catcacaaga aacttttgat gcagttaaag    4560
agacatctat agcaatagga aaagatcctg tagaagtagc agaagcacca ggatttgttg    4620
taaatagaat attaatacca atgattaatg aagcagttgg tatattagca gaaggaatag    4680
cttcagtaga agacatagat aaagctatga acttggagc taatcaccca atgggaccat     4740
tagaattagg tgatttata ggtcttgata tatgtcttgc tataatggat gttttatact     4800
cagaaactgg agattctaag tatagaccac atacattact taagaagtat gtaagagcag    4860
gatggcttgg aagaaaatca ggaaaaggtt tctacgatta ttcaaaataa gtttacagga    4920
tctgcaggga ggaggaaatc atggagttga acaacgttat tctggagaaa gaaggcaagg    4980
tggcggttgt caccattaac cgtccaaagg ccctgaacgc tctgaactcg gatacctga    5040 aagagatgga ttcgttatt ggcgagattg agaatgacag cgaagtgctg gctgtgattc     5100
tgaccggtgc gggtgagaag agctttgtcg cgggtgcgga catcagcgag atgaaagaaa    5160
```

```
tgaacaccat cgaaggccgt aagttcggta ttctgggcaa caaggtgttt cgtcgtctgg   5220
aactgctgga gaaacctgtc attgctgccg tgaacggttt cgcgctgggc ggtggttgcg   5280
agatcgctat gagctgcgat attcgtatcg catcgtccaa cgcacgcttt ggtcaaccgg   5340
aggtcggtct gggtatcact ccgggtttcg gcggtacgca acgtctgagc cgcctggttg   5400
gcatgggcat ggcgaaacag ttgatttttca cggcacagaa cattaaggcg gatgaggcgc   5460
tgcgtattgg tctggtgaat aaggtcgttg agccaagcga actgatgaat accgcgaaag   5520
aaattgcgaa caagatcgtt agcaatgccc cggtggccgt taagctgtcg aaacaggcaa   5580
tcaaccgtgg catgcagtgt gacatcgaca ccgccctggc gtttgagagc gaggcgtttg   5640
gtgagtgctt ctccaccgag gaccaaaagg atgcgatgac cgcgttcatt gagaaacgca   5700
agatcgaggg tttcaagaat cgttaataga ggaggatagg aggttttcat atgattgtga   5760
aaccgatggt ccgtaataat atctgtctga atgctcaccc gcagggctgt aaaaaaggcg   5820
tggaagatca aattgaatat accaaaaaac gtattacggc agaagtgaaa gccggcgcaa   5880
aagctccgaa aaacgtgctg gttctgggtt gcagcaatgg ctatggtctg gcttctcgca   5940
ttaccgcggc cttttggctac ggtgcagcta cgatcggcgt tagtttcgaa aaagcaggtt   6000
ccgaaaccaa atatggcacg ccgggttggt acaacaatct ggcttttgat gaagcggcca   6060
aacgtgaagg cctgtatagt gtcaccattg atggtgacgc gttctccgat gaaattaaag   6120
cacaggtgat cgaagaagcg aagaaaaaag gcattaaatt tgacctgatc gtttacagcc   6180
tggcatctcc ggtccgtacc gatccggaca cgggtatcat gcataaatct gtgctgaaac   6240
cgtttggcaa aaccttcacg ggtaaaaccg ttgatccgtt cacgggcgaa ctgaaagaaa   6300
ttagcgcgga accggccaac gatgaagaag cagctgcgac cgtcaaagtg atgggcggtg   6360
aagactggga acgttggatc aaacagctga gtaaagaagg cctgctggaa gaaggttgca   6420
ttaccctggc gtattcctac atcggcccgg aagcaaccca agctctgtat cgcaaaggca   6480
cgattggtaa agcgaaagaa catctggaag cgaccgccca ccgtctgaac aaagaaaatc   6540
cgtcaatccg cgccttcgtt tcggtcaata aggtctggt tacccgtgca tcagctgtga   6600
ttccggttat cccgctgtac ctggcatcgc tgtttaaagt catgaaagaa aaaggcaacc   6660
atgaaggttg tattgaacag atcacccgcc tgtatgccga acgtctgtac cgcaaagatg   6720
gtacgattcc ggtggacgaa gaaaatcgta ttcgcatcga tgactgggaa ctggaagaag   6780
atgtccaaaa agccgtgagc gccctgatgg aaaaagttac cggcgaaaac gcggaatctc   6840
tgacggatct ggccggttat cgtcacgact ttctggcgag taatggtttt gatgttgaag   6900
gcattaacta cgaagctgaa gtggaacgct tgatcgcat ttgatctaga gaattcgtca   6960
acgaattcaa gcttgatatc attcaggacg agcctcagac tccagcgtaa ctggactgaa   7020
aacaaactaa agcgcccttg tggcgcttta gttttgttcc gctcatgata ataatggttt   7080
cttagacgtc aggtggcact tttcggggaa atgtgcgcgc ccgcgttcct gctggcgctg   7140
ggcctgtttc tggcgctgga cttcccgctg ttccgtcagc agcttttcgc ccacggcctt   7200
gatgatcgcg gcggccttgg cctgcatatc ccgattcaac ggccccaggg cgtccagaac   7260
gggcttcagg cgctcccgaa ggtctcgggc cgtctcttgg gcttgatcgg ccttcttgcg   7320
catctcacgc gctcctgcgg cggcctgtag ggcaggctca taccctgcc gaaccgcttt   7380 tgtcagccgg tcggcacgg cttccggcgt ctcaacgcgc tttgagattc ccagcttttc   7440
ggccaatccc tgcggtgcat aggcgcgtgg ctcgaccgct tgcgggctga tggtgacgtg   7500
gcccactggt ggccgctcca gggcctcgta gaacgcctga atgcgcgtgt gacgtgcctt   7560
```

-continued

```
gctgccctcg atgccccgtt gcagccctag atcggccaca gcggccgcaa acgtggtctg    7620
gtcgcgggtc atctgcgctt tgttgccgat gaactccttg gccgacagcc tgccgtcctg    7680
cgtcagcggc accacgaacg cggtcatgtg cgggctggtt tcgtcacggt ggatgctggc    7740
cgtcacgatg cgatccgccc cgtacttgtc cgccagccac ttgtgcgcct tctcgaagaa    7800
cgccgcctgc tgttcttggc tggccgactt ccaccattcc gggctggccg tcatgacgta    7860
ctcgaccgcc aacacagcgt ccttgcgccg cttctctggc agcaactcgc gcagtcggcc    7920
catcgcttca tcggtgctgc tggccgccca gtgctcgttc tctggcgtcc tgctggcgtc    7980
agcgttgggc gtctcgcgct cgcggtaggc gtgcttgaga ctggccgcca cgttgcccat    8040
tttcgccagc ttcttgcatc gcatgatcgc gtatgccgcc atgcctgccc ctccctttg    8100 gtgtccaacc ggctcgacgg gggcagcgca aggcggtgcc tccggcgggc cactcaatgc    8160
ttgagtatac tcactagact ttgcttcgca aagtcgtgac cgcctacggc ggctgcggcg    8220
ccctacgggc ttgctctccg ggcttcgccc tgcgcggtcg ctgcgctc               8268
```

<210> SEQ ID NO 19
<211> LENGTH: 8959
<212> TYPE: DNA
<213> ORGANISM: Escherichia coli

<400> SEQUENCE: 19

```
ccttgccagc ccgtggatat gtggacgatg gccgcgagcg gccaccggct ggctcgcttc     60
gctcggcccg tggacaaccc tgctggacaa gctgatggac aggctgcgcc tgcccacgag    120
cttgaccaca gggattgccc accggctacc cagccttcga ccacataccc accggctcca    180
actgcgcggc ctgcgccctt gccccatcaa ttttttttaat tttctctggg aaaagcctc    240 cggcctgcgg cctgcgcgct tcgcttgccg gttggacacc aagtggaagg cgggtcaagg    300
ctcgcgcagc gaccgcgcag cggcttggcc ttgacgcgcc tggaacgacc caagcctatg    360
cgagtggggg cagtcgaagg cgaagcccgc ccgcctgccc ccgagcctc acggcggcga    420 gtgcgggggt tccaagggg cagcgccacc ttgggcaagg ccgaaggccg cgcagtcgat    480
caacaagccc cggaggggcc acttttttgcc ggaggggag ccgcgccgaa ggcgtggggg    540
aaccccgcag gggtgccctt cttttgggcac caaagaacta gatataggc gaaatgcgaa    600 agacttaaaa atcaacaact taaaaaaggg gggtacgcaa cagctcattg cggcaccccc    660
cgcaatagct cattgcgtag gttaaagaaa atctgtaatt gactgccact tttacgcaac    720
gcataattgt tgtcgcgctg ccgaaaagtt gcagctgatt gcgcatggtg ccgcaaccgt    780
gcggcaccct accgcatgga gataagcatg ccacgcagt ccagagaaat cggcattcaa    840
gccaagaaca agcccggtca ctgggtgcaa acggaacgca aagcgcatga ggcgtgggcc    900
gggcttattg cgaggaaacc cacggcggca atgctgctgc atcacctcgt ggcgcagatg    960
ggccaccaga acgccgtggt ggtcagccag aagacacttt ccaagctcat cggacgttct   1020
ttgcggacgg tccaatacgc agtcaaggac ttggtggccg agcgctggat ctccgtcgtg   1080
aagctcaacg gccccggcac cgtgtcggcc tacgtggtca tgaccgcgt ggcgtggggc   1140 cagccccgcg accagttgcg cctgtcgtg ttcagtgccg ccgtggtggt tgatcacgac   1200
gaccaggacg aatcgctgtt ggggcatggc gacctgcgcc gcatcccgac cctgtatccg   1260
ggcgagcagc aactaccgac cggccccggc gaggagccgc ccagccagcc cggcattccg   1320
ggcatggaac cagacctgcc agccttgacc gaaacggagg aatgggaacg gcgcgggcag   1380
```

```
cagcgcctgc cgatgcccga tgagccgtgt tttctggacg atggcgagcc gttggagccg    1440
ccgacacggg tcacgctgcc gcgccggtag tacgtacccg gaattgccag ctggggcgcc    1500
ctctggtaag gttgggaagc cctgcaaagt aaactggatg gctttcttgc cgccaaggat    1560
ctgatggcgc agggggatcaa gctctgatca agagacagga tgaggatcgt ttcgatgaag    1620
cagcgtatta cagtgacagt tgacagcgac agctatcagt tgctcaaggc atatgatgtc    1680
aatatctccg gtctggtaag cacaaccatg cagaatgaag cccgtcgtct gcgtgccgaa    1740
cgctggaaag cggaaaatca ggaagggatg gctgaggtcg cccggtttat tgaaatgaac    1800
ggctcttttg ctgacgagaa cagggactgg tgaaatgcag tttaaggttt acacctataa    1860
aagagagagc cgttatcgtc tgtttgtgga tgtacagagc gatattattg acacgcccgg    1920
gcgacggatg gtgatccccc tggccagtgc acgtctgctg tcagataaag tctcccgtga    1980
actttacccg gtggtgcata tcggggatga agctggcgc atgatgacca ccgatatggc     2040
cagtgtgccg gtctccgtta tcggggaaga agtggctgat ctcagccacc gcgaaaatga    2100
catcaaaaac gccattaacc tgatgttctg gggaatataa atcctagacg aattctctag    2160
tagaggttcc aacttcacc ataatgaaat aagatcacta ccgggcgtat ttttgagtt      2220 atcgagattt tcaggagcta aggaagctaa atggagaaa aaaatcactg gatataccac     2280
cgttgatata tcccaatggc atcgtaaaga acattttgag gcatttcagt cagttgctca    2340
atgtacctat aaccagaccg ttcagctgga tattacggcc tttttaaaga ccgtaaagaa    2400
aaataagcac aagttttatc cggcctttat tcacattctt gcccgcctga tgaatgctca    2460
tccggaattc cgtatggcaa tgaaagacg tgagctggtg atatgggata gtgttcaccc     2520
ttgttacacc gttttccatg agcaaactga acgttttca tcgctctgga gtgaatacca     2580
cgacgatttc cggcagtttc tacacatata ttcgcaagat gtggcgtgtt acggtgaaaa    2640
cctggcctat ttccctaaag ggtttattga gaatatgttt ttcgtctcag ccaatccctg    2700
ggtgagtttc accagttttg atttaaacgt ggccaatatg gacaacttct tcgccccgt     2760 tttcaccatg ggcaaatatt atacgcaagg cgacaaggtg ctgatgccgc tggcgattca    2820
ggttcatcat gccgtttgtg atggcttcca tgtcggcaga atgcttaatg aattacaaca    2880
gtactgcgat gagtggcagg gcggggcgta agatcttct cgacgctctc ccttatgcga    2940
ctcctgcatt aggaaattaa tacgactcac tatagggaa ttgtgagcgg ataacaattc      3000
ccctgtagaa ataattttgt ttaactttaa taaggagata taccatggcg gcggacaccc    3060
tgctgatcct gggcgactcc ctgtcggcgg gctaccgcat gtcggcgtcg gcggcgtggc    3120
cggcgctgct gaacgacaag tggcagtcca agacctcggt ggtcaacgcc tcgatcagcg    3180
gcgacacgag ccagcagggc ctggcccgcc tgccggcgct gctgaagcag caccagccgc    3240
gctgggtgct ggtcgagctg ggcggcaacg acggcctgcg cggcttccag ccgcagcaga    3300
ccgaacagac gctgcgccag atcctgcagg acgtgaaggc cgcgaacgcc gagccgctgc    3360
tgatgcagat ccgcctgccg gcgaactacg gccgtcgcta caacgaggcc ttctccgcga    3420
tctacccgaa gctggccaag gaattcgacg tgccgctgct gccgttcttc atggaggaag    3480
tctacctgaa gccgcagtgg atgcaggacg acggcatcca cccgaaccgc gacgcgcagc    3540
cgttcatcgc cgactggatg gccaagcaac tgcagccgct ggtcaaccac gactcctgaa    3600
tttaaatccc ttatgcgact cctgcattag gaaattaata cgactcacta tagggaatt    3660 gtgagcggat aacaattccc ctgtagaaat aattttgttt aactttaata aggagatata    3720
ccatgacgga tgtccgcttt cgtatcattg gcacgggcgc ttacgtcccg gaacgcattg    3780
```

```
tcagcaacga cgaagtcggc gcaccggctg gtgtggatga cgattggatt acgcgtaaaa   3840
ccggtatccg ccagcgtcgc tgggcggccg acgatcaagc aacgagcgat ctggctaccg   3900
cagctggtcg tgcagcactg aaagcagctg gcattacgcc ggaacagctg accgtcatcg   3960
cagtggctac ctctacgccg gaccgtccgc agccgccgac cgcggcctat gttcaacatc   4020
acctgggtgc aaccggcacg gcagcttttg atgttaacgc tgtgtgcagc ggtacggttt   4080
tcgcgctgag ctctgttgcc ggcaccctgg tctatcgtgg cggttacgca ctggtcattg   4140
gtgctgatct gtactcacgt atcctgaatc cggcggaccg caaaaccgtg gttctgttcg   4200
gcgatggtgc gggcgcgatg gtgctgggcc cgaccagcac cggcaccggt ccgattgtgc   4260
gtcgcgttgc actgcatacg tttggcggtc tgaccgatct gatccgtgtt ccggccggcg   4320
gttcccgcca ccgctggac accgatggtc tggacgcagg cctgcaatat tttgcgatgg   4380
atggccgcga agtccgtcgc ttcgtgaccg aacatctgcc gcagctgatt aaaggttttc   4440
tgcacgaagc gggcgtggat gcggcggata ttagccattt cgtgccgcac caagccaacg   4500
gtgtgatgct ggacgaagtt tttggcgaac tgcatctgcc gcgtgcaacc atgcaccgta   4560
cggtggaaac ctacgtaat acgggcgcag ctagtattcc gatcacgatg gatgcggccg   4620 tcgtgcagg ttccttccgt ccgggcgaac tggttctgct ggcgggcttt ggcggcggta   4680
tggcggcttc gtttgctctg attgaatggt gacctaatgc aggctgcagg cggatacgag   4740
gaggaataaa ccatgaaaaa ggtatgtgtt ataggtgcag gtactatggg ttcaggaatt   4800
gctcaggcat ttgcagctaa aggatttgaa gtagtattaa gagatattaa agatgaattt   4860
gttgatagag gattagattt tatcaataaa aatctttcta aattagttaa aaaggaaag    4920 atagaagaag ctactaaagt tgaaatctta actagaattt ccggaacagt tgaccttaat   4980
atggcagctg attgcgattt agttatagaa gcagctgttg aaagaatgga tattaaaaag   5040 cagattttg ctgacttaga caatatatgc aagccagaaa caattcttgc atcaaataca    5100
tcatcacttt caataacaga agtggcatca gcaactaaaa gacctgataa ggttataggt   5160
atgcatttct ttaatccagc tcctgttatg aagcttgtag aggtaataag aggaatagct   5220
acatcacaag aaacttttga tgcagttaaa gagacatcta tagcaatagg aaaagatcct   5280
gtagaagtag cagaagcacc aggatttgtt gtaaatagaa tattaatacc aatgattaat   5340
gaagcagttg gtatattagc agaaggaata gcttcagtag aagacataga taaagctatg   5400
aaacttggag ctaatcaccc aatgggacca ttagaattag gtgattttat aggtcttgat   5460
atatgtcttg ctataatgga tgtttatac tcagaaactg gagattctaa gtatagacca   5520
catacattac ttaagaagta tgtaagagca ggatggcttg aagaaaatc aggaaaggt    5580 ttctacgatt attcaaaata gtttacagg atctgcaggg aggaggaaat catggagttg    5640
aacaacgtta ttctggagaa agaaggcaag gtggcggttg tcaccattaa ccgtccaaag   5700
gccctgaacg ctctgaactc ggatacccct aaagagatgg attacgttat tggcgagatt   5760
gagaatgaca gcgaagtgct ggctgtgatt ctgaccggtg cgggtgagaa gagctttgtc   5820
gcgggtgcgg acatcagcga gatgaaagaa atgaacacca tcgaaggccg taagttcggt   5880
attctgggca acaaggtgtt tcgtcgtctg gaactgctgg agaaacctgt cattgctgcc   5940
gtgaacggtt tcgcgctggg cggtggttgc gagatcgcta tgagctgcga tattcgtatc   6000
gcatcgtcca acgcacgctt tggtcaaccg gaggtcggtc tgggtatcac tccgggtttc   6060
ggcggtacgc aacgtctgag ccgcctggtt ggcatgggca tggcgaaaca gttgattttc   6120
```

```
acggcacaga acattaaggc ggatgaggcg ctgcgtattg gtctggtgaa taaggtcgtt      6180
gagccaagcg aactgatgaa taccgcgaaa gaaattgcga acaagatcgt tagcaatgcc      6240
ccggtggccg ttaagctgtc gaaacaggca atcaaccgtg gcatgcagtg tgacatcgac      6300
accgccctgg cgtttgagag cgaggcgttt ggtgagtgct tctccaccga ggaccaaaag      6360
gatgcgatga ccgcgttcat tgagaaacgc aagatcgagg gtttcaagaa tcgttaatag      6420
aggaggatag gaggttttca tatgattgtg aaaccgatgg tccgtaataa tatctgtctg      6480
aatgctcacc cgcagggctg taaaaaaggc gtggaagatc aaattgaata taccaaaaaa      6540
cgtattacgg cagaagtgaa agccggcgca aaagctccga aaaacgtgct ggttctgggt      6600
tgcagcaatg gctatggtct ggcttctcgc attaccgcgg cctttggcta cggtgcagct      6660
acgatcggcg ttagtttcga aaaagcaggt tccgaaacca aatatggcac gccgggttgg      6720
tacaacaatc tggcttttga tgaagcggcc aaacgtgaag gcctgtatag tgtcaccatt      6780
gatggtgacg cgttctccga tgaaattaaa gcacaggtga tcgaagaagc gaagaaaaaa      6840
ggcattaaat ttgacctgat cgtttacagc ctggcatctc cggtccgtac cgatccggac      6900
acgggtatca tgcataaatc tgtgctgaaa ccgtttggca aaaccttcac gggtaaaacc      6960
gttgatccgt tcacgggcga actgaaagaa attagcgcgg aaccggccaa cgatgaagaa      7020
gcagctgcga ccgtcaaagt gatgggcggt gaagactggg aacgttggat caaacagctg      7080
agtaaagaag gcctgctgga agaaggttgc attaccctgg cgtattccta catcggcccg      7140
gaagcaaccc aagctctgta tcgcaaaggc acgattggta aagcgaaaga acatctggaa      7200
gcgaccgccc accgtctgaa caaagaaaat ccgtcaatcc gcgccttcgt ttcggtcaat      7260
aaaggtctgg ttacccgtgc atcagctgtg attccggtta tcccgctgta cctggcatcg      7320
ctgtttaaag tcatgaaaga aaaaggcaac catgaaggtt gtattgaaca gatcacccgc      7380
ctgtatgccg aacgtctgta ccgcaaagat ggtacgattc cggtggacga agaaaatcgt      7440
attcgcatcg atgactggga actggaagaa gatgtccaaa aagccgtgag cgccctgatg      7500
gaaaaagtta ccggcgaaaa cgcggaatct ctgacggatc tggccggtta tcgtcacgac      7560
tttctggcga gtaatggttt tgatgttgaa ggcattaact acgaagctga agtggaacgc      7620
tttgatcgca tttgatctag agaattcgtc aacgaattca gcttgatat cattcaggac      7680
gagcctcaga ctccagcgta actggactga aaacaaacta aagcgccctt gtggcgcttt      7740
agttttgttc cgctcatgat aataatggtt tcttagacgt caggtggcac ttttcgggga      7800
aatgtgcgcg cccgcgttcc tgctggcgct gggcctgttt ctggcgctgg acttcccgct      7860
gttccgtcag cagcttttcg cccacggcct tgatgatcgc ggcggccttg gcctgcatat      7920
cccgattcaa cggccccagg gcgtccagaa cgggcttcag gcgctcccga aggtctcggg      7980
ccgtctcttg ggcttgatcg gccttcttgc gcatctcacg cgctcctgcg gcggcctgta      8040
gggcaggctc ataccctgc cgaaccgctt ttgtcagccg gtcggccacg gcttccggcg      8100
tctcaacgcg ctttgagatt cccagctttt cggccaatcc ctgcggtgca taggcgcgtg      8160
gctcgaccgc ttgcgggctg atggtgacgt ggcccactgg tggccgctcc agggcctcgt      8220
agaacgcctg aatgcgcgtg tgacgtgcct tgctgccctc gatgcccgt tgcagcccta      8280
gatcggccac agcggccgca acgtggtct ggtcgcgggt catctgcgct tgttgccga      8340
tgaactcctt ggccgacagc ctgccgtcct gcgtcagcgg caccgaac gcggtcatgt      8400
gcgggctggt ttcgtcacgg tggatgctgg ccgtcacgat gcgatccgcc ccgtacttgt      8460
ccgccagcca cttgtgcgcc ttctcgaaga acgccgcctg ctgttcttgg ctggccgact      8520
```

-continued

```
tccaccattc cgggctggcc gtcatgacgt actcgaccgc caacacacgcg tccttgcgcc    8580 gcttctctgg cagcaactcg cgcagtcggc ccatcgcttc atcggtgctg ctggccgcc     8640 agtgctcgtt ctctggcgtc ctgctggcgt cagcgttggg cgtctcgcgc tcgcggtagg    8700
cgtgcttgag actggccgcc acgttgccca ttttcgccag cttcttgcat cgcatgatcg    8760
cgtatgccgc catgcctgcc cctcccttt  ggtgtccaac cggctcgacg ggggcagcgc    8820
aaggcggtgc ctccggcggg ccactcaatg cttgagtata ctcactagac tttgcttcgc    8880
aaagtcgtga ccgcctacgg cggctgcggc gccctacggg cttgctctcc gggcttcgcc    8940
ctgcgcggtc gctgcgctc                                                 8959
```

<210> SEQ ID NO 20
<211> LENGTH: 5367
<212> TYPE: DNA
<213> ORGANISM: Artificial Sequence
<220> FEATURE:
<223> OTHER INFORMATION: pET-28b(empty vector)

<400> SEQUENCE: 20

```
ggcgaatggg acgcgccctg tagcggcgca ttaagcgcgg cgggtgtggt ggttacgcgc      60
agcgtgaccg ctacacttgc cagcgcccta gcgcccgctc ctttcgcttt cttcccttcc    120
tttctcgcca cgttcgccgg ctttccccgt caagctctaa atcggggggct ccctttaggg    180 ttccgattta gtgctttacg gcacctcgac cccaaaaaac ttgattaggg tgatggttca    240
cgtagtgggc catcgccctg atagacggtt tttcgccctt tgacgttgga gtccacgttc    300
tttaatagtg gactcttgtt ccaaactgga acaacactca accctatctc ggtctattct    360
tttgatttat aagggatttt gccgatttcg gcctattggt taaaaaatga gctgatttaa    420
caaaaattta acgcgaattt taacaaaata ttaacgttta catttcagg  tggcacttt     480 cggggaaatg tgcgcggaac ccctatttgt ttatttttct aaatacattc aaatatgtat    540
ccgctcatga attaattctt agaaaaactc atcgagcatc aaatgaaact gcaatttatt    600
catatcagga ttatcaatac catatttttg aaaaagccgt ttctgtaatg aaggagaaaa    660
ctcaccgagg cagttccata ggatggcaag atcctggtat cggtctgcga ttccgactcg    720
tccaacatca atacaaccta ttaatttccc ctcgtcaaaa ataaggttat caagtgagaa    780
atcaccatga gtgacgactg aatccggtga gaatggcaaa agtttatgca tttctttcca    840
gacttgttca acaggccagc cattacgctc gtcatcaaaa tcactcgcat caaccaaacc    900
gttattcatt cgtgattgcg cctgagcgag acgaaatacg cgatcgctgt taaaaggaca    960
attacaaaca ggaatcgaat gcaaccggcg caggaacact gccagcgcat caacaatatt   1020
ttcacctgaa tcaggatatt cttctaatac ctggaatgct gttttcccgg ggatcgcagt   1080
ggtgagtaac catgcatcat caggagtacg gataaaatgc ttgatggtcg gaagaggcat   1140
aaattccgtc agccagttta gtctgaccat ctcatctgta acatcattgg caacgctacc   1200
tttgccatgt ttcagaaaca actctggcgc atcgggcttc ccatacaatc gatagattgt   1260
cgcacctgat tgcccgacat tatcgcgagc ccatttatac ccatataaat cagcatccat   1320
gttggaattt aatcgcggcc tagagcaaga cgtttcccgt tgaatatggc tcataacacc   1380
ccttgtatta ctgtttatgt aagcagacag ttttattgtt catgaccaaa atcccttaac   1440
gtgagttttc gttccactga gcgtcagacc ccgtagaaaa gatcaaagga tcttcttgag   1500
atcctttttt tctgcgcgta atctgctgct tgcaaacaaa aaaaccaccg ctaccagcgg   1560
```

```
tggtttgttt gccggatcaa gagctaccaa ctcttttttcc gaaggtaact ggcttcagca    1620
gagcgcagat accaaatact gtccttctag tgtagccgta gttaggccac cacttcaaga    1680
actctgtagc accgcctaca tacctcgctc tgctaatcct gttaccagtg gctgctgcca    1740
gtggcgataa gtcgtgtctt accgggttgg actcaagacg atagttaccg gataaggcgc    1800
agcggtcggg ctgaacgggg ggttcgtgca cacagcccag cttggagcga acgacctaca    1860
ccgaactgag atacctacag cgtgagctat gagaaagcgc cacgcttccc gaagggagaa    1920
aggcggacag gtatccggta agcggcaggg tcggaacagg agagcgcacg agggagcttc    1980 caggggaaa cgcctggtat ctttatagtc ctgtcgggtt tcgccacctc tgacttgagc     2040
gtcgattttt gtgatgctcg tcaggggggc ggagcctatg gaaaaacgcc agcaacgcgg    2100 ccttttacg gttcctggcc ttttgctggc cttttgctca catgttcttt cctgcgttat      2160
cccctgattc tgtggataac cgtattaccg cctttgagtg agctgatacc gctcgccgca    2220
gccgaacgac cgagcgcagc gagtcagtga gcgaggaagc ggaagagcgc ctgatgcggt    2280
attttctcct tacgcatctg tgcggtattt cacaccgcat atatggtgca ctctcagtac     2340
aatctgctct gatgccgcat agttaagcca gtatacactc cgctatcgct acgtgactgg    2400
gtcatggctg cgccccgaca cccgccaaca cccgctgacg cgccctgacg ggcttgtctg    2460
ctcccggcat ccgcttacag acaagctgtg accgtctccg ggagctgcat gtgtcagagg    2520
ttttcaccgt catcaccgaa acgcgcgagg cagctgcgt aaagctcatc agcgtggtcg     2580
tgaagcgatt cacagatgtc tgcctgttca tccgcgtcca gctcgttgag tttctccaga    2640
agcgttaatg tctggcttct gataaagcgg gccatgttaa gggcggtttt ttcctgtttg    2700
gtcactgatg cctccgtgta aggggatttc tgttcatgg gggtaatgat accgatgaaa    2760
cgagagagga tgctcacgat acgggttact gatgatgaac atgcccggtt actggaacgt    2820
tgtgagggta acaactggc ggtatggatg cggcgggacc agagaaaaat cactcagggt     2880
caatgccagc gcttcgttaa tacagatgta ggtgttccac agggtagcca gcagcatcct    2940
gcgatgcaga tccggaacat aatggtgcag gcgctgact tccgcgtttc cagactttac     3000
gaaacacgga aaccgaagac cattcatgtt gttgctcagg tcgcagacgt tttgcagcag    3060
cagtcgcttc acgttcgctc gcgtatcggt gattcattct gctaaccagt aaggcaaccc    3120
cgccagccta gccgggtcct caacgacagg agcacgatca tgcgcacccg tggggccgcc    3180
atgccggcga taatggcctg cttctcgccg aaacgtttgg tggcgggacc agtgacgaag    3240
gcttgagcga gggcgtgcaa gattccgaat accgcaagcg acaggccgat catcgtcgcg    3300
ctccagcgaa agcggtcctc gccgaaaatg acccagagcg ctgccggcac ctgtcctacg    3360
agttgcatga taaagaagac agtcataagt gcggcgacga tagtcatgcc ccgcgcccac    3420
cggaaggagc tgactgggtt gaaggctctc aagggcatcg gtcgagatcc cggtgcctaa    3480
tgagtgagct aacttacatt aattgcgttg cgctcactgc ccgctttcca gtcgggaaac    3540
ctgtcgtgcc agctgcatta atgaatcggc caacgcgcgg ggagaggcgg tttgcgtatt    3600
gggcgccagg gtggtttttc ttttcaccag tgagacgggc aacagctgat tgcccttcac    3660
cgcctggccc tgagagagtt gcagcaagcg gtccacgctg gtttgcccca gcaggcgaaa    3720
atcctgtttg atggtggtta acggcgggat ataacatgag ctgtcttcgg tatcgtcgta    3780
tcccactacc gagatatccg caccaacgcg cagcccggac tcggtaatgg cgcgcattgc    3840
gcccagcgcc atctgatcgt tggcaaccag catcgcagtg gaacgatgc cctcattcag      3900 catttgcatg gtttgttgaa aaccggacat ggcactccag tcgccttccc gttccgctat    3960
```

```
cggctgaatt tgattgcgag tgagatattt atgccagcca gccagacgca gacgcgccga    4020
gacagaactt aatgggcccg ctaacagcgc gatttgctgg tgacccaatg cgaccagatg    4080
ctccacgccc agtcgcgtac cgtcttcatg ggagaaaata atactgttga tgggtgtctg    4140
gtcagagaca tcaagaaata acgccggaac attagtgcag gcagcttcca cagcaatggc    4200
atcctggtca tccagcggat agttaatgat cagcccactg acgcgttgcg cgagaagatt    4260
gtgcaccgcc gctttacagg cttcgacgcc gcttcgttct accatcgaca ccaccacgct    4320
ggcacccagt tgatcggcgc gagatttaat cgccgcgaca atttgcgacg gcgcgtgcag    4380
ggccagactg gaggtggcaa cgccaatcag caacgactgt ttgcccgcca gttgttgtgc    4440
cacgcggttg gaatgtaat tcagctccgc catcgccgct tccactttt cccgcgtttt     4500 cgcagaaacg tggctggcct ggttcaccac gcgggaaacg gtctgataag agacaccggc    4560
atactctgcg acatcgtata acgttactgg tttcacattc accaccctga attgactctc    4620
ttccgggcgc tatcatgcca taccgcgaaa ggttttgcgc cattcgatgg tgtccgggat    4680
ctcgacgctc tcccttatgc gactcctgca ttaggaagca gcccagtagt aggttgaggc    4740
cgttgagcac cgccgccgca aggaatggtg catgcaagga gatggcgccc aacagtcccc    4800
cggccacggg gcctgccacc atacccacgc cgaaacaagc gctcatgagc ccgaagtggc    4860
gagcccgatc ttccccatcg gtgatgtcgg cgatataggc gccagcaacc gcacctgtgg    4920
cgccggtgat gccggccacg atgcgtccgg cgtagaggat cgagatctcg atcccgcgaa    4980
attaatacga ctcactatag gggaattgtg agcggataac aattcccctc tagaaataat    5040
tttgtttaac tttaagaagg agatatacca tgggcagcag ccatcatcat catcatcaca    5100
gcagcggcct ggtgccgcgc ggcagccata tggctagcat gactggtgga cagcaaatgg    5160
gtcgggatcc gaattcgagc tccgtcgaca agcttgcggc cgcactcgag caccaccacc    5220
accaccactg agatccggct gctaacaaag cccgaaagga agctgagttg gctgctgcca    5280
ccgctgagca ataactagca taaccccttg gggcctctaa acgggtcttg aggggttttt    5340
tgctgaaagg aggaactata tccggat                                       5367
```

<210> SEQ ID NO 21
<211> LENGTH: 471
<212> TYPE: PRT
<213> ORGANISM: Hydrocarboniphaga effusa

<400> SEQUENCE: 21

```
Met Glu Lys Arg Met Ala Arg Gln Met Asn Pro Leu Asp Ala Ser Trp
1               5                   10                  15

Leu Phe Val Asp Ser Ala Arg Thr Pro Met Gln Val Gly Val Leu Ala
                20                  25                  30

Ile Phe Ser Leu Pro Asp Asp Ala Gly Ser Asp Phe Ile Lys Asn Leu
            35                  40                  45

Phe Ala His Leu Arg Lys Pro Ser Gly Phe Ala Ala Pro Phe Asn Leu
        50                  55                  60

Lys Leu Arg Gly Ser Arg Leu Leu Pro Gly Ala His Arg Leu Ile Pro
65                  70                  75                  80

Ala Trp Ile Glu Glu Thr Arg Ile Asp Leu Asp Tyr His Leu Arg His
                85                  90                  95

Ser Ala Leu Pro Gln Pro Gly Gly Glu Arg Glu Leu Gly Val Leu Ile
            100                 105                 110

Ser Arg Leu His Ser Tyr Pro Leu Asp Phe Ser Lys Pro Leu Trp Glu
```

```
            115                 120                 125
Cys His Ile Ile Glu Gly Leu Glu Asn Asp Arg Phe Ala Leu Tyr Met
    130                 135                 140

Lys Met His His Ser Leu Val Asp Gly Val Gly Met Arg Met Leu
145                 150                 155                 160

Ser Arg Leu Leu Ser Ala Asp Pro Asn Val Asp Leu Pro Pro Pro
                165                 170                 175

Trp Ala Ser Gly Ser Gly Glu Lys Ser His Ala Gly Lys Ser Ala Gly
                180                 185                 190

Ala Asn Trp Gln Gln Leu Ile Glu Gln Ala Arg Arg Gln Ala Gln Phe
            195                 200                 205

Val Pro Ser Leu Ala Lys Ala Ile Gly Glu Thr Trp Lys Glu Ser Leu
210                 215                 220

Gln His Arg His Pro Glu Leu Gly Ser Pro Phe Arg Ala Pro Leu Ser
225                 230                 235                 240

Leu Leu Asn Gly Lys Ile Gly Ala Gln Arg Arg Phe Ala Thr Gln His
                245                 250                 255

Tyr Asp Leu Ala Arg Ile Arg Ala Leu Ala Lys Arg Ala Lys Gly Thr
                260                 265                 270

Val Asn Asp Val Phe Leu Cys Leu Cys Ala Gly Ala Leu Arg Arg Tyr
            275                 280                 285

Leu Glu Glu Leu Gly Val Leu Pro Asp Glu Pro Leu Thr Ala Gly Leu
290                 295                 300

Pro Val Ser Val Arg Ala Asn Asp Val Gly Ser Gly Asn Ala Ile
305                 310                 315                 320

Ser Phe Ile Ile Ala Asn Leu His Thr His Ile Ala Asp Pro Leu Glu
                325                 330                 335

Arg Leu Ala Ala Ile Arg Lys Ser Thr Gln Leu Ala Lys Gln Arg Phe
                340                 345                 350

Gln Asn Leu Pro Arg Glu Ala Ile Asn Ser Tyr Thr Ser Leu Phe Met
            355                 360                 365

Ala Pro Phe Met Leu Gln Leu Leu Ser Gly Leu Gly Gly Ile Thr Arg
370                 375                 380

Pro Met Phe Asn Leu Thr Ile Ser Asn Val Pro Gly Pro Asp Ser Ile
385                 390                 395                 400

Arg Tyr Phe Asn Gly Ala Lys Met Glu Gln Met Tyr Pro Val Ser Leu
                405                 410                 415

Leu Ala His Gly Gln Ala Leu Asn Ile Thr Val Phe Ser Tyr Ala Gly
                420                 425                 430

Gln Phe Asn Val Gly Tyr Thr Gly Cys Arg Asp Thr Leu Pro His Val
            435                 440                 445

Gln Arg Leu Ser Val Tyr Thr Gly Glu Ala Leu Glu Glu Leu Glu Thr
        450                 455                 460

Leu Leu Gly Ala Ala Gly Ser
465                 470

<210> SEQ ID NO 22
<211> LENGTH: 489
<212> TYPE: PRT
<213> ORGANISM: Marinobacter sp.

<400> SEQUENCE: 22

Met Lys Arg Leu Ala Thr Leu Asp Ala Ser Trp Leu Ala Val Glu Ser
1               5                   10                  15
```

-continued

```
Asp Asp Thr Pro Met His Val Gly Asn Leu Gln Ile Phe Ser Leu Pro
             20                  25                  30

Asp Asn Ala Pro Ser Thr Phe Ala Gly Asp Leu Val Lys Ser Met Lys
         35                  40                  45

Gln Ala Gly Asn Val Glu Leu Pro Trp Gly Cys Lys Leu Val Trp Pro
     50                  55                  60

Gly Phe Leu Gly Arg Val Leu Ala Pro Thr Trp Lys His Asp Lys His
65                  70                  75                  80

Ile Asp Leu Asp Tyr His Val Arg His Ser Ala Leu Pro Lys Pro Gly
                 85                  90                  95

Gly Glu Arg Glu Leu Gly Glu Leu Val Ser Arg Leu His Ser Asn Pro
            100                 105                 110

Leu Asp Leu Ser Arg Pro Leu Trp Glu Cys His Met Ile Glu Gly Leu
        115                 120                 125

Glu His Asn Arg Phe Ala Leu Tyr Thr Lys Met His His Cys Met Ile
    130                 135                 140

Asp Gly Ile Ser Gly Val Arg Leu Met Gln Arg Val Leu Ser Lys Ser
145                 150                 155                 160

Pro Asp Glu Arg Asp Met Leu Pro Pro Trp Ser Val Arg Pro Glu Ser
                165                 170                 175

Thr Arg Gly Lys Lys Thr Asp Ser Glu Ala Ser Val Pro Gly Ala Ile
            180                 185                 190

Ser Gln Ala Met Glu Ala Leu Lys Leu Gln Leu Gly Leu Ala Pro Arg
        195                 200                 205

Leu Trp Gln Ala Ser Asn Arg Leu Ile His Ser Val Arg His Pro Glu
    210                 215                 220

Asp Gly Leu Thr Ala Pro Phe Thr Gly Pro Val Ser Lys Ile Asn His
225                 230                 235                 240

Arg Val Thr Gly Gln Arg Arg Phe Ala Thr Gln Gln Tyr Gln Leu Glu
                245                 250                 255

Asp Met Lys Ala Met Ala Arg Ala Ser Gly Ser Ser Met Asn Asp Ile
            260                 265                 270

Val Leu Tyr Leu Cys Gly Thr Ala Leu Arg Arg Phe Leu Leu Glu Gln
        275                 280                 285

Asp Asp Leu Pro Glu Ile Ser Leu Thr Ala Gly Ile Pro Val Asn Ile
290                 295                 300

Arg Pro Ala Asp Asp Glu Gly Thr Gly Thr Gln Ile Ser Phe Met Ile
305                 310                 315                 320

Ala Ala Leu Ala Thr Asn Gln Pro Asp Pro Leu Thr Arg Leu Lys Cys
                325                 330                 335

Ile Lys Glu Ser Ser Cys Lys Ala Lys Glu His Leu Gln Lys Leu Pro
            340                 345                 350

Lys Lys Ala Leu Thr Gln Tyr Thr Met Met Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Thr Glu Asp Leu Tyr Tyr Glu
385                 390                 395                 400

Gly Ala Lys Leu Glu Ala Met Tyr Pro Val Ser Leu Ile Thr His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
```

```
            435                 440                 445
Val Tyr Thr Gly Glu Ala Leu Glu Glu Leu Arg Thr Leu Leu Leu Pro
450                 455                 460

Pro Lys Lys Lys Pro Ser Pro Arg Lys Pro Thr Ala Ala Lys Lys
465                 470             475                 480

Lys Pro Ala Val Asn Ser Asn Ala Ser
                485

<210> SEQ ID NO 23
<211> LENGTH: 458
<212> TYPE: PRT
<213> ORGANISM: Smaragdicoccus niigatensis

<400> SEQUENCE: 23

Met Leu Phe Leu Thr Val Glu Ser Gln Glu Thr Met Leu His Val Ala
1               5                   10                  15

Gly Leu Leu Gln Phe Lys Pro Thr Asn Gly Ala Arg Ala Glu Glu Ile
                20                  25                  30

Thr Ala Gln Met Arg Asp Glu Leu Ala Ser Val Val Glu Pro Pro
            35                  40                  45

Trp Asn Leu Lys Leu Ala Tyr Pro Asn Phe Leu Leu His Pro Met Gln
50                  55                  60

Arg Trp Val Thr Asp Thr Glu Ile Asp Pro Thr Tyr His Val Arg Arg
65                  70                  75                  80

Ser Ala Leu Pro Ser Pro Gly Asp Glu Arg Glu Leu Gly Val Leu Ile
                85                  90                  95

Ser Arg Leu His Ser Arg Pro Leu Asp Leu Ser Arg Pro Pro Trp Glu
            100                 105                 110

Ala His Leu Ile Glu Gly Leu Glu Asn Gly Asn Leu Ala Leu Tyr Val
        115                 120                 125

Lys Val His His Ser Leu Val Asp Gly Tyr Thr Ala Ala Lys Leu Leu
130                 135                 140

Ser Arg Ala Leu Ser Lys Asp Pro Asp Asp Thr Gly Thr Pro Leu Phe
145                 150                 155                 160

Phe Ala Val Pro Pro Thr Arg Arg Glu Arg Ala Ser Leu Leu Asp Ser
                165                 170                 175

Ala Pro Ala Pro Ser Leu Gly Gly Val Val Asp Thr Val Arg Ser Gly
            180                 185                 190

Phe Thr Ser Leu Asn Asp Val Phe Lys Ala Leu Val Lys Val Asn Arg
        195                 200                 205

Ser Arg Arg Asp Glu Ala Asn Ala Leu Val Pro Ser Leu Gln Ala Pro
210                 215                 220

Arg Thr Ile Phe Asp Asn Arg Ile Ser Arg Asn Arg Phe Ala Thr
225                 230                 235                 240

Gln Gln Tyr Asp Leu Pro Arg Leu Lys Arg Ile Ala Ala Ala Thr Gly
                245                 250                 255

Gly Thr Leu Asn Asp Val Leu Leu Ala Ile Cys Ala Gly Gly Leu Arg
            260                 265                 270

Arg Tyr Leu Ser Glu Leu Gly Glu Leu Pro Asp Lys Pro Leu Ile Ala
        275                 280                 285

Phe Ile Pro Val Asn Val Arg Pro Lys Asp Pro Gly Gly Gly Asn
290                 295                 300

Ala Val Ala Gly Met Leu Ala Asn Leu Ser Thr His Ile Asp Asp Pro
305                 310                 315                 320
```

```
Lys Glu Arg Ile Glu Ser Ile Ile Ala Ser Thr Arg Ala Ala Lys Glu
            325                 330                 335

Gln Met Glu Gly Met Thr Arg Asn Ala Ile Leu Ala Tyr Thr Ala Ile
        340                 345                 350

Leu Ser Ala Pro Phe Val Val Gln Thr Ser Thr Ala Gln Ala Gly Leu
        355                 360                 365

Gly Gln Val Leu Pro Pro Thr Tyr Asn Val Met Ile Ser Asn Val Pro
370                 375                 380

Gly Pro Thr Glu Pro Leu Tyr Phe Arg Gly His Lys Leu Glu Ser Asp
385                 390                 395                 400

Tyr Pro Val Ser Ile Pro Met His Gly Thr Ala Leu Asn Ile Thr Cys
            405                 410                 415

Leu Ser Tyr Ala Gly Thr Leu Asn Val Gly Phe Ile Gly Cys Arg Asp
            420                 425                 430

Asn Ala Pro His Leu Gln His Leu Ala Val Tyr Ser Gly Asp Ala Val
            435                 440                 445

Val Glu Leu Glu Thr Ala Phe Gly Ile Lys
    450                 455

<210> SEQ ID NO 24
<211> LENGTH: 450
<212> TYPE: PRT
<213> ORGANISM: Nocardia cyriacigeorgica

<400> SEQUENCE: 24

Met Ile Asp Leu Ile Ser Pro Thr Asp Ala Ile Phe Leu Leu Asn Glu
1               5                   10                  15

Ser Arg Glu His Pro Met His Val Gly Ser Leu Gln Leu Phe Glu Pro
            20                  25                  30

Pro Glu Gly Ala Gly Pro Glu Phe Ala Arg Ser Val His Gln Gln Leu
        35                  40                  45

Leu Glu Ser Ala Val Thr Glu Pro Thr Phe Arg Lys Arg Pro Gly Arg
    50                  55                  60

Ile Leu Gly Gly Ile Ser Asn Leu Thr Trp Thr Tyr Asp Asp Glu Val
65                  70                  75                  80

Asp Leu Asp Tyr His Val Gln Arg Ala Ala Leu Ala Thr Pro Gly Arg
                85                  90                  95

Val Arg Glu Leu Leu Ala Met Thr Ser Arg Leu His Ser Gly Leu Leu
            100                 105                 110

Asp Arg His Arg Pro Leu Trp Glu Gln His Leu Ile Glu Gly Leu Asp
        115                 120                 125

Asp Gly Arg Phe Ala Val Tyr Thr Lys Val His His Ala Leu Ile Asp
130                 135                 140

Gly Val Ala Ala Gln Arg Leu Leu Arg Arg Thr Leu Thr Thr Asp Pro
145                 150                 155                 160

Phe Asp Thr Asp Leu Arg Ala Pro Trp Asn Leu Pro Lys Arg Thr Arg
                165                 170                 175

Ser Gly Ala Gly Gly Glu Arg Ser Arg Thr Ala Asp Phe Ala Arg Ser
            180                 185                 190

Leu Gly Lys Leu Ala Pro Ser Thr Val Ser Leu Ile Arg Ser Ala Leu
        195                 200                 205

Ala Glu Gln Gln Leu Thr Leu Pro Phe Ser Ala Pro Asp Thr Ile Phe
    210                 215                 220

Asn Val Arg Ile Gly Gly Ala Arg Arg Cys Ala Ala Gln Ser Trp Pro
225                 230                 235                 240
```

```
Leu Glu Arg Ile Arg Ala Val Lys Gly Ala Thr Gly Ala Thr Val Asn
                245                 250                 255

Asp Val Val Leu Ala Met Cys Ser Ala Leu Arg Ser Tyr Leu Leu
            260                 265                 270

Glu His Asn Ala Leu Pro Asp Thr Pro Leu Ile Ala Met Val Pro Val
            275                 280                 285

Ser Leu Arg Thr Glu Ser Glu Ala Asp Ser Gly Gly Asn Ile Val Gly
            290                 295                 300

Thr Ile Leu Cys Asn Leu Ala Thr His Val Ser Asp Ala Ala Glu Arg
305                 310                 315                 320

Leu Glu Ile Ile Ser Ala Ser Met Arg Glu Gly Lys Arg Leu Phe Ala
                325                 330                 335

Glu Met Pro Arg Ile Gln Ala Leu Ala Val Ser Ala Val Met Val Ser
            340                 345                 350

Pro Leu Gly Leu Ala Ser Leu Pro Gly Phe Val Ser Met Thr Arg Pro
            355                 360                 365

Pro Phe Asn Ile Val Ile Ser Asn Val Pro Gly Pro Gln Gln Pro Met
            370                 375                 380

Tyr Tyr Cys Gly Ala Arg Met Asp Gly Ser Tyr Pro Met Ser Ile Val
385                 390                 395                 400

Leu Asp Gly Gln Ala Leu Asn Ile Thr Leu Ser Ser Asn Ala Asp Asn
                405                 410                 415

Leu Asp Phe Gly Ile Val Gly Cys Arg Arg Ser Val Pro His Leu Gln
            420                 425                 430

Arg Leu Leu Ala His Leu Glu Ala Gly Leu Ala Glu Leu Glu His Val
            435                 440                 445

Thr Ser
    450

<210> SEQ ID NO 25
<211> LENGTH: 454
<212> TYPE: PRT
<213> ORGANISM: Mycobacterium smegmatis

<400> SEQUENCE: 25

Met Gln Leu Met Ser Pro Thr Asp Ser Met Phe Leu Ile Ala Glu Ser
1               5                   10                  15

Arg Glu His Pro Met His Val Gly Gly Leu Ala Leu Tyr Asp Pro Pro
                20                  25                  30

Asp Asp Ala Gly Pro Glu Phe Val Arg Glu Leu Tyr Glu Glu Met Val
            35                  40                  45

Arg His Thr Asp Phe Gln Pro Val Phe Arg Lys His Pro Ala Thr Leu
        50                  55                  60

Leu Gly Gly Ile Ala Asn Val Gly Trp Thr Leu Asp Asp Glu Val Asp
65              70                  75                  80

Leu Asp Tyr His Leu Arg Arg Ser Ala Leu Pro Ser Pro Gly Arg Pro
                85                  90                  95

Arg Glu Leu Leu Glu Leu Thr Ser Arg Val His Gly Thr Leu Leu Asp
            100                 105                 110

Arg His Arg Pro Leu Trp Glu Ala Tyr Leu Ile Glu Gly Met Ala Asp
            115                 120                 125

Gly Arg Phe Ala Val Tyr Thr Lys Val His His Ser Leu Ile Asp Gly
            130                 135                 140

Val Ser Ala Met Lys Leu Val Glu Arg Thr Leu Ser Glu Asp Pro Ser
```

```
            145                 150                 155                 160
Asp Thr Thr Val Arg Val Pro Trp Asn Leu Pro Arg Arg Glu Ser Ser
                165                 170                 175

Arg Arg Ala Gly Ser Ser Leu Ala Arg Thr Ala Thr Gly Ala Ala
            180                 185                 190

Thr Ser Leu Ala Ala Leu Ala Pro Ser Thr Ile Arg Leu Ala Arg Ala
                195                 200                 205

Ala Leu Leu Glu Gln Gln Leu Thr Leu Pro Phe Gly Ala Pro Arg Thr
            210                 215                 220

Met Phe Asn Val Lys Ile Gly Ala Arg Arg Val Ala Ala Gln Ser
225                 230                 235                 240

Trp Pro Leu Glu Arg Leu Arg Arg Ile Lys Ala Val Thr Gly Ala Thr
                245                 250                 255

Ile Asn Asp Ile Val Leu Ala Met Cys Ala Gly Ala Leu Arg Ala Tyr
                260                 265                 270

Leu Ala Glu Gln Asp Ala Leu Pro Asp Arg Pro Leu Ile Ala Met Val
            275                 280                 285

Pro Val Ser Met Arg Ser Glu His Glu Ala Asp Ala Gly Gly Asn Met
    290                 295                 300

Val Gly Ser Ile Leu Cys Ser Leu Gly Thr Asp Val Glu Asp Pro Ala
305                 310                 315                 320

Asp Arg Leu Ala Val Ile Arg Arg Ser Ile Thr Asp Asn Lys Arg Val
                325                 330                 335

Phe Ser Glu Leu Pro Arg Leu Gln Ala Leu Ala Leu Ser Ala Leu Leu
            340                 345                 350

Ile Ala Pro Leu Gly Leu Thr Thr Ala Phe Pro Gly Phe Val Asp Ala
                355                 360                 365

Thr Ala Pro Pro Phe Asn Leu Val Ile Ser Asn Val Pro Gly Pro Lys
    370                 375                 380

Lys Pro Leu Tyr Trp Arg Gly Ala Arg Leu Ala Gly Asn Tyr Pro Leu
385                 390                 395                 400

Ser Ile Ala Leu Asp Gly Gln Ala Leu Asn Met Thr Val Val Ser Asn
                405                 410                 415

Ala His Asn Leu Asp Phe Gly Leu Val Gly Cys Arg Arg Ser Val Pro
            420                 425                 430

His Leu Gln Arg Leu Leu Gly His Leu Glu Thr Ser Leu Lys Asp Leu
    435                 440                 445

Glu Thr Ala Thr Gly Ala
    450

<210> SEQ ID NO 26
<211> LENGTH: 458
<212> TYPE: PRT
<213> ORGANISM: Smaragdicoccus niigatensis

<400> SEQUENCE: 26

Met Leu Phe Leu Thr Val Glu Ser Gln Glu Thr Met Leu His Val Ala
1               5                   10                  15

Gly Leu Leu Gln Phe Lys Pro Thr Asn Gly Ala Arg Ala Glu Glu Ile
            20                  25                  30

Thr Ala Gln Met Arg Asp Glu Leu Ala Ser Val Val Val Glu Pro Pro
        35                  40                  45

Trp Asn Leu Lys Leu Ala Tyr Pro Asn Phe Leu Leu His Pro Met Gln
    50                  55                  60
```

Arg Trp Val Thr Asp Thr Glu Ile Asp Pro Thr Tyr His Val Arg Arg
 65                  70                  75                  80

Ser Ala Leu Pro Ser Pro Gly Asp Glu Arg Glu Leu Gly Val Leu Ile
                 85                  90                  95

Ser Arg Leu His Ser Arg Pro Leu Asp Leu Ser Arg Pro Pro Trp Glu
            100                 105                 110

Ala His Leu Ile Glu Gly Leu Glu Asn Gly Asn Leu Ala Leu Tyr Val
        115                 120                 125

Lys Val His His Ser Leu Val Asp Gly Tyr Thr Ala Lys Leu Leu
    130                 135                 140

Ser Arg Ala Leu Ser Lys Asp Pro Asp Thr Gly Thr Pro Leu Phe
145                 150                 155                 160

Phe Ala Val Pro Pro Thr Arg Arg Glu Arg Ala Ser Leu Leu Asp Ser
                165                 170                 175

Ala Pro Ala Pro Ser Leu Gly Gly Val Val Asp Thr Val Arg Ser Gly
            180                 185                 190

Phe Thr Ser Leu Asn Asp Val Phe Lys Ala Leu Val Lys Val Asn Arg
        195                 200                 205

Ser Arg Arg Asp Glu Ala Asn Ala Leu Val Pro Ser Leu Gln Ala Pro
210                 215                 220

Arg Thr Ile Phe Asp Asn Arg Ile Ser Arg Asn Arg Arg Phe Ala Thr
225                 230                 235                 240

Gln Gln Tyr Asp Leu Pro Arg Leu Lys Arg Ile Ala Ala Ala Thr Gly
                245                 250                 255

Gly Thr Leu Asn Asp Val Leu Leu Ala Ile Cys Ala Gly Gly Leu Arg
            260                 265                 270

Arg Tyr Leu Ser Glu Leu Gly Glu Leu Pro Asp Lys Pro Leu Ile Ala
        275                 280                 285

Phe Ile Pro Val Asn Val Arg Pro Lys Asp Pro Gly Gly Gly Asn
290                 295                 300

Ala Val Ala Gly Met Leu Ala Asn Leu Ser Thr His Ile Asp Asp Pro
305                 310                 315                 320

Lys Glu Arg Ile Glu Ser Ile Ile Ala Ser Thr Arg Ala Ala Lys Glu
                325                 330                 335

Gln Met Glu Gly Met Thr Arg Asn Ala Ile Leu Ala Tyr Thr Ala Ile
            340                 345                 350

Leu Ser Ala Pro Phe Val Val Gln Thr Ser Thr Ala Gln Ala Gly Leu
        355                 360                 365

Gly Gln Val Leu Pro Pro Thr Tyr Asn Val Met Ile Ser Asn Val Pro
370                 375                 380

Gly Pro Thr Glu Pro Leu Tyr Phe Arg Gly His Lys Leu Glu Ser Asp
385                 390                 395                 400

Tyr Pro Val Ser Ile Pro Met His Gly Thr Ala Leu Asn Ile Thr Cys
                405                 410                 415

Leu Ser Tyr Ala Gly Thr Leu Asn Val Gly Phe Ile Gly Cys Arg Asp
            420                 425                 430

Asn Ala Pro His Leu Gln His Leu Ala Val Tyr Ser Gly Asp Ala Val
        435                 440                 445

Val Glu Leu Glu Thr Ala Phe Gly Ile Lys
    450                 455

<210> SEQ ID NO 27
<211> LENGTH: 452
<212> TYPE: PRT

<213> ORGANISM: Mycobacterium sp.

<400> SEQUENCE: 27

```
Met Glu Ile Met Ser Pro Thr Asp Ala Met Phe Leu Leu Gly Glu Ser
1               5                   10                  15

Arg Glu His Pro Met His Val Gly Gly Leu Gln Leu Phe Ser Pro Pro
            20                  25                  30

Glu Gly Ala Gly Pro Glu Phe Ile His Glu Leu His Arg Asp Met Leu
        35                  40                  45

Ala His Thr Asn Phe Asn Pro Thr Tyr Arg Lys Arg Pro Ala Arg Phe
    50                  55                  60

Leu Gly Gly Ile Ala Ser Phe Ala Trp Ala Tyr Asp Asp Glu Leu Asp
65                  70                  75                  80

Ile Asp Tyr His Leu Arg Arg Ser Ala Leu Pro Arg Pro Gly Arg Ile
                85                  90                  95

Arg Glu Leu Leu Asp Leu Cys Gly Arg Leu His Thr Ser Leu Leu Asp
            100                 105                 110

Arg His Arg Pro Leu Trp Glu Thr Tyr Leu Val Glu Gly Leu Glu Asp
        115                 120                 125

Gly Arg Phe Ala Val Tyr Ser Lys Ala His His Ala Leu Leu Asp Gly
130                 135                 140

Val Ser Ala Leu Arg Met Ala Met Arg Thr Leu Ser Asp Asp Pro Ala
145                 150                 155                 160

Glu Gln Glu Val Arg Val Pro Trp Asp Leu Pro Ser Arg Lys Arg Ala
                165                 170                 175

Pro Lys Gln Ser Pro Ser Leu Ile Gly Ser Ala Val Gly Ala Val Gly
            180                 185                 190

Thr Ala Ala Gly Leu Ala Pro Ser Thr Phe Arg Val Ala Arg Ala Val
        195                 200                 205

Leu Leu Glu Gln Asn Leu Thr Arg Thr Phe Ser Ala Pro Lys Thr Met
210                 215                 220

Phe Asn Val Lys Ile Gly Gly Ala Arg Arg Val Ala Ala Gln Ser Trp
225                 230                 235                 240

Pro Ile Ala Arg Ile Lys Ala Val Lys Gln Ala Ala Gly Gly Val Thr
                245                 250                 255

Val Asn Asp Val Val Leu Ala Met Cys Ala Gly Ala Leu Arg Gly Tyr
            260                 265                 270

Leu Leu Glu Gln Asn Ala Leu Pro Asp Ala Pro Leu Ile Ala Met Val
        275                 280                 285

Pro Val Ser Leu Arg Ala Glu Ala Asp Ala Gly Gly Asn Gln
290                 295                 300

Val Gly Ala Ile Leu Cys Asn Leu Ala Thr Asp Val Lys Asp Pro Ala
305                 310                 315                 320

Thr Arg Leu Gln Thr Ile Ala Asp Ser Met Arg Gly Asn Lys Gln Val
                325                 330                 335

Phe Ser Gly Leu Ser Lys Thr Glu Ser Met Ala Leu Ser Ala Leu Leu
            340                 345                 350

Leu Ser Pro Ile Ala Leu Ser Ala Val Pro Gly Phe Val Asp Ala Thr
        355                 360                 365

Pro Pro Pro Phe Asn Ile Val Ile Ser Asn Val Pro Gly Pro Arg Val
    370                 375                 380

Pro Met Tyr Trp Lys Gly Ala Arg Leu Asp Gly Asn Tyr Pro Leu Ser
385                 390                 395                 400
```

```
Ile Ala Leu Asp Gly Gln Ala Leu Asn Ile Thr Leu Val Asn Asn Gly
                405                 410                 415

Asp Asn Leu Asp Phe Gly Leu Val Gly Cys Arg His Ser Val Pro His
            420                 425                 430

Leu Gln Arg Leu Leu Gly His Leu Glu Asp Ser Leu Thr Asp Leu Glu
        435                 440                 445

Ala Ala Val Arg
    450

<210> SEQ ID NO 28
<211> LENGTH: 461
<212> TYPE: PRT
<213> ORGANISM: Acinetobacter pittii

<400> SEQUENCE: 28

Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Glu Ile Pro
            20                  25                  30

Glu Asn Ala Pro Glu Thr Phe Val His Asp Leu Val Glu Asp Ile Arg
        35                  40                  45

Arg Ser Lys Ser Ile Pro Ile Pro Pro Phe Asn Asn Arg Leu Asn Gly
    50                  55                  60

Leu Phe Trp Asp Glu Asp Glu Phe Asp Ile Asp His His Phe Arg
65                  70                  75                  80

His Ile Ala Leu Pro His Pro Gly Arg Ile Arg Glu Leu Leu Val Tyr
                85                  90                  95

Ile Ser Gln Gln His Ser Ser Leu Ile Asp Arg Ala Lys Pro Leu Trp
            100                 105                 110

Thr Cys Asp Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser Lys Thr Pro Glu Glu Lys His Val Val Pro
145                 150                 155                 160

Leu Trp Cys Val Glu Ser Lys Arg Thr Lys Arg Leu Lys Val Pro Thr
                165                 170                 175

Pro Ser Thr Ser Lys Ile Lys Ser Ile Leu Gly Gly Ile Lys Ser Gln
            180                 185                 190

Leu Asp Ile Ala Pro Lys Val Met Gln Glu Leu Ser Gln Thr Ile Phe
        195                 200                 205

Lys Glu Met Gly Lys Asn Pro Asp Tyr Val Ser Thr Phe Gln Ala Pro
    210                 215                 220

Val Ser Ile Leu Asn Gln Arg Val Ser Ala Ser Arg Arg Phe Ala Ala
225                 230                 235                 240

Gln Ser Phe Glu Leu Ser Arg Leu Arg Lys Ile Ser Lys Ala Leu Gly
                245                 250                 255

Val Thr Ile Asn Asp Val Val Leu Ala Val Cys Ser Gly Ala Leu Arg
            260                 265                 270

Glu Tyr Leu Ile Ser Gln Asn Ser Leu Pro Lys Lys Pro Leu Ile Ala
        275                 280                 285

Met Val Pro Ala Ser Leu Arg Thr Asp Ser Asp Met Ser Asn Arg
    290                 295                 300

Ile Thr Met Ile Leu Ala Asn Leu Gly Thr His Lys Asp Gln Pro Leu
305                 310                 315                 320
```

-continued

```
Glu Arg Leu Glu Ile Ile Arg Arg Ser Met Gln Asn Ser Lys Gln Arg
            325                 330                 335

Phe Ser Arg Met Thr Ala Asn Glu Ile Leu Asn Tyr Ser Ala Val Val
            340                 345                 350

Tyr Gly Pro Ala Gly Leu Asn Ile Met Ser Gly Met Leu Pro Lys Arg
            355                 360                 365

Gln Ala Phe Asn Leu Val Ile Ser Asn Val Pro Gly Pro Arg Glu Pro
            370                 375                 380

Leu Tyr Trp Asn Gly Ala Lys Leu Asp Ala Leu Tyr Pro Ala Ser Ile
385                 390                 395                 400

Val Met Asp Gly Gln Ala Leu Asn Ile Thr Met Thr Ser Tyr Leu Asp
            405                 410                 415

Lys Leu Glu Val Gly Leu Thr Ala Cys Arg Asn Ala Leu Pro Lys Met
            420                 425                 430

Gln Asn Leu Leu Thr His Leu Glu Asp Glu Ile Gln Arg Phe Glu Glu
            435                 440                 445

Ile Ile Ala Glu Lys Gln Leu Lys His His Ser Ala Ser
            450                 455                 460

<210> SEQ ID NO 29
<211> LENGTH: 508
<212> TYPE: PRT
<213> ORGANISM: Limnobacter sp.

<400> SEQUENCE: 29

Met Ala Arg Asn Ile Pro Leu Leu Asp Ala Ser Trp Leu Tyr Val Glu
1               5                   10                  15

Ser Lys Glu Ala Pro Met His Val Gly Ser Met Ala Ile Phe Thr Val
            20                  25                  30

Pro Glu Gly Glu Thr Ser Gln Gln Ala Ile Ala Arg Ile Val Gln Met
            35                  40                  45

Leu Arg Asn Ser Leu Glu Phe Ala Pro Pro Phe Asn Tyr Arg Leu Ser
        50                  55                  60

Ser Pro Arg Leu Leu Thr Leu Met Pro Lys Trp Ile Glu Ala Asp Lys
65                  70                  75                  80

Ile Asp Leu Asp Tyr His Phe Arg His Ser Ala Leu Pro Ala Pro Gly
            85                  90                  95

Gly Glu Arg Glu Leu Gly Thr Leu Ile Ser Arg Leu His Ser His Pro
            100                 105                 110

Leu Asp Phe Arg Lys Pro Leu Trp Glu Met His Leu Ile Glu Gly Leu
        115                 120                 125

Tyr Gly Asn Arg Phe Ala Leu Tyr Thr Lys Met His His Ser Leu Met
    130                 135                 140

Asp Gly Val Gly Gly Met Arg Leu Met Glu Arg Ile Phe Gly Lys Ser
145                 150                 155                 160

Ala Lys Glu Ser Met Asn Leu Pro Ala Pro Trp Ser Val Gly Thr Ile
            165                 170                 175

Ser Arg Lys Lys Lys Asn Ser Glu Pro Gln His Phe Ala Asp Gln Ala
            180                 185                 190

Arg Glu Ala Trp Glu Ala Ala Lys Leu Ser Gly Gln Ser Leu Pro Ala
        195                 200                 205

Ala Gly Arg Ala Leu Met Asp Leu Met Arg Glu Ala Val Lys Pro Thr
    210                 215                 220

Asp Pro Ala Leu Ala Thr Pro Phe Ser Gly Pro Lys Ser Ile Val Asn
```

```
            225                 230                 235                 240
Lys Arg Val Gly Gly Ala Arg Arg Leu Ala Thr Gln Thr Tyr Pro Leu
                245                 250                 255

Glu Arg Val Arg Ala Val Ala Glu Ala Ala Lys Val Ser Val Asn Asp
                260                 265                 270

Ile Phe Leu Ala Ile Cys Ser Ser Ile Arg Arg Tyr Leu Leu Glu
                275                 280                 285

Arg Asp Ala Leu Pro Ser Glu Ser Leu Thr Ala Gly Leu Pro Val Ser
290                 295                 300

Val Arg Pro Ala Asp Asp Leu Asp Gly Gly Asn Ala Ile Ser Phe Ile
305                 310                 315                 320

Ile Ala Asn Leu Tyr Thr Thr Glu Ala Asp Pro Leu Thr Arg Leu Lys
                325                 330                 335

Glu Ile Arg Arg Ser Thr Gln Leu Ala Lys Ala Asn Leu Gln Ala Met
                340                 345                 350

Pro Lys Glu Ala Ile Asn Asn Tyr Thr Ile Met Leu Met Ala Pro Met
                355                 360                 365

Met Leu Gln Leu Val Ser Gly Leu Gly Gly Leu Thr Arg Pro Ile Phe
    370                 375                 380

Asn Thr Val Ile Ser Asn Val Pro Gly Pro Ser Arg Asp Leu Tyr Phe
385                 390                 395                 400

Ser Gly Cys Arg Leu Glu Gln Phe Tyr Pro Ile Ser Leu Ile Pro His
                405                 410                 415

Gly Gln Ala Leu Asn Ile Thr Val Val Ser Tyr Ser Gly Gln Phe Asn
                420                 425                 430

Val Ala Phe Thr Gly Asp His Asp Ala Leu Pro Ser Met Gln Arg Leu
                435                 440                 445

Ser Val Tyr Thr Gly Glu Ala Leu Glu Glu Leu Glu Ala Ala Leu Gly
                450                 455                 460

Val Lys Trp Ala Ser Lys Pro Val Val Lys Pro Val Thr Glu Lys Arg
465                 470                 475                 480

Pro Val Ala Ala Lys Lys Pro Ala Val Arg Lys Pro Ala Thr Ala Lys
                485                 490                 495

Val Gly Ala Gly Lys Pro Val Lys Ala Pro Glu Asp
                500                 505

<210> SEQ ID NO 30
<211> LENGTH: 479
<212> TYPE: PRT
<213> ORGANISM: Psychrobacter sp.

<400> SEQUENCE: 30

Met Arg Leu Leu Thr Ala Val Asp Gln Leu Phe Leu Leu Glu Ser
1               5                   10                  15

Arg Lys Gln Pro Met His Val Gly Gly Leu Phe Leu Phe Glu Leu Pro
                20                  25                  30

Glu Asp Ala Asp Ile Ser Phe Val His Gln Leu Val Lys Gln Met Gln
            35                  40                  45

Asp Ser Asp Val Pro Pro Thr Phe Pro Phe Asn Gln Val Leu Glu His
        50                  55                  60

Met Val Phe Trp Lys Lys Asp Lys Asn Phe Asp Val Glu His His Leu
65                  70                  75                  80

His His Val Ala Leu Pro Lys Pro Ala Arg Val Arg Glu Leu Leu Met
                85                  90                  95
```

```
Tyr Val Ser Arg Glu His Gly Arg Leu Leu Asp Arg Ala Met Pro Leu
            100                 105                 110

Trp Glu Cys His Val Ile Glu Gly Ile Gln Pro Glu Ser Glu Gly Ser
        115                 120                 125

Pro Glu Arg Phe Ala Leu Tyr Phe Lys Ile His His Ser Leu Val Asp
    130                 135                 140

Gly Ile Ala Ala Met Arg Leu Val Lys Lys Ser Leu Ser Gln Ser Pro
145                 150                 155                 160

Asn Glu Pro Val Thr Leu Pro Ile Trp Ser Leu Met Ala Arg His Arg
                165                 170                 175

Asn Gln Ile Asp Ala Ile Leu Pro Lys Glu Arg Ser Ala Leu Arg Ile
            180                 185                 190

Leu Lys Glu Gln Val Ser Thr Ile Lys Pro Val Phe Thr Glu Leu Leu
        195                 200                 205

Asp Asn Phe Lys Asn Tyr Asn Asp Asp Ser Tyr Val Ser Thr Phe Asp
    210                 215                 220

Ala Pro Arg Ser Ile Leu Asn Arg Arg Ile Ser Ala Ser Arg Arg Ile
225                 230                 235                 240

Ala Ala Gln Ser Tyr Asp Ile Lys Arg Phe Asn Asp Ile Ala Glu Arg
                245                 250                 255

Ile Asn Ile Ser Lys Asn Asp Val Val Leu Ala Val Cys Ala Gly Ala
            260                 265                 270

Ile Arg Arg Tyr Leu Ile Ser Met Asp Ala Leu Pro Ser Lys Pro Leu
        275                 280                 285

Ile Ala Phe Val Pro Met Ser Leu Arg Thr Asp Ser Val Ala Gly
    290                 295                 300

Asn Gln Leu Ser Phe Val Leu Ala Asn Leu Gly Thr His Leu Asp Asp
305                 310                 315                 320

Pro Leu Ser Arg Ile Lys Leu Ile His Arg Ser Met Asn Asn Gly Lys
                325                 330                 335

Arg Arg Phe Arg Arg Met Asn Gln Ala Gln Val Ile Asn Tyr Ser Val
            340                 345                 350

Val Ser Tyr Ala Trp Glu Gly Ile Asn Leu Ala Thr Gly Leu Phe Pro
        355                 360                 365

Lys Lys Gln Ala Phe Asn Leu Ile Ile Ser Asn Val Pro Gly Ser Glu
    370                 375                 380

Lys Ser Leu Tyr Trp Asn Gly Ala Arg Leu Gln Ser Leu Tyr Pro Ala
385                 390                 395                 400

Ser Ile Val Phe Asn Gly Gln Ala Met Asn Ile Thr Leu Ala Ser Tyr
                405                 410                 415

Leu Asp Lys Ile Glu Phe Gly Ile Thr Ala Cys Ser Lys Ala Leu Pro
            420                 425                 430

His Val Gln Asp Met Leu Met Leu Ile Glu Glu Leu Gln Leu Leu
        435                 440                 445

Glu Lys Val Ser Lys Glu Leu Glu Phe Asn Gly Ile Thr Val Glu Asp
    450                 455                 460

Lys Ser Gly Tyr Lys Asp Asn Gly Lys Thr Lys Leu Ala Pro
465                 470                 475

<210> SEQ ID NO 31
<211> LENGTH: 451
<212> TYPE: PRT
<213> ORGANISM: Alcanivorax sp.

<400> SEQUENCE: 31
```

```
Met Ala Arg Lys Leu Ser Ile Met Asp Ser Gly Trp Leu Met Met Glu
1               5                   10                  15

Thr Arg Glu Thr Pro Met His Val Gly Gly Leu Ala Leu Phe Ala Ile
            20                  25                  30

Pro Glu Asp Ala Pro Ala Asp Tyr Met Glu Gly Ile Tyr Arg Tyr Leu
            35                  40                  45

Val Glu Val Asn Gly Ile Cys Arg Pro Phe Asn Gln Lys Ile Gln Ser
        50                  55                  60

Arg Leu Pro Met Arg Met Asp Ala Ala Trp Val Glu Asp Lys Thr Phe
65                  70                  75                  80

Asp Ile Asp Tyr His Val Arg His Ser Ala Leu Pro Arg Pro Gly Arg
                85                  90                  95

Val Arg Glu Leu Leu Ala Leu Val Ser Arg Leu His Ala Gln Arg Leu
                100                 105                 110

Asp Pro Ser Arg Pro Leu Trp Glu Ser Tyr Leu Ile Glu Gly Leu Glu
            115                 120                 125

Gly Asn Arg Phe Ala Leu Tyr Thr Lys Met His His Ser Met Val Asp
        130                 135                 140

Gly Val Ala Gly Met Tyr Leu Met Gln Ser Arg Leu Ala Asn Ser Ala
145                 150                 155                 160

Glu Asp Arg Leu Pro Val Pro Trp Ser Gly Glu Trp Asp Ala Glu Lys
                165                 170                 175

Lys Pro Arg Lys Ser Ser Gly Ala Pro Ala Ala Thr Gly Met Lys
                180                 185                 190

Gly Thr Val Asn Asn Leu Arg Arg Gly Ser Gly Gln Leu Val Asp Leu
            195                 200                 205

Leu Arg Gln Pro Lys Asp Gly Asn Val Lys Thr Ile Tyr Arg Ala Pro
210                 215                 220

Lys Thr Gln Leu Asn Arg Arg Val Thr Gly Ala Arg Arg Phe Ala Ala
225                 230                 235                 240

Gln Ser Trp Ser Leu Pro Arg Ile Lys Ala Ala Lys Gln His Gly
                245                 250                 255

Gly Thr Val Asn Asp Met Phe Leu Ala Met Cys Gly Gly Ala Leu Arg
            260                 265                 270

Arg Tyr Leu Leu Ser Gln Asp Ala Leu Pro Asp Gln Pro Leu Val Ala
        275                 280                 285

Gln Val Pro Val Ser Leu Arg Ser Ala Asp Gln Ala Gly Asp Gly Gly
        290                 295                 300

Asn Ala Ile Thr Thr Val Gln Val Ser Leu Gly Thr His Ile Ala Glu
305                 310                 315                 320

Pro Leu Asn Arg Leu Ala Ala Ile Gln Asp Ser Met Lys Gly Val Lys
            325                 330                 335

Ser Arg Leu Gly Asp Met Gln Lys Ser Glu Ile Asp Val Tyr Thr Val
            340                 345                 350

Leu Thr Asn Val Pro Leu Ser Leu Gly Gln Val Thr Gly Leu Ser Gly
            355                 360                 365

Arg Val Ser Pro Met Phe Asn Leu Val Ile Ser Asn Val Pro Gly Pro
        370                 375                 380

Lys Asp Pro Leu Tyr Leu Asn Gly Ala Glu Met Leu Ala Ser Tyr Pro
385                 390                 395                 400

Val Ser Leu Val Leu His Gly Tyr Ala Leu Asn Ile Thr Val Val Ser
                405                 410                 415
```

-continued

```
Tyr Lys Asp Ser Leu Glu Phe Gly Val Ile Gly Cys Arg Asp Thr Leu
                420                 425                 430

Pro His Ile Gln Arg Phe Leu Asp Tyr Phe Glu Glu Ser Leu Ala Glu
        435                 440                 445

Leu Glu Ser
        450

<210> SEQ ID NO 32
<211> LENGTH: 462
<212> TYPE: PRT
<213> ORGANISM: Moraxella catarrhalis

<400> SEQUENCE: 32

Met Arg Ala Leu Ser Ile Val Asp Ser Leu Phe Leu Trp Leu Glu Asn
1               5                   10                  15

Thr Lys Gln Pro Met His Val Ala Gly Ile Cys Val Phe Glu Leu Pro
            20                  25                  30

Asn Asp Gln Asp Glu Ile Ser Phe Ile Asn Val Leu Ala Asn Gln Ile
        35                  40                  45

Asp Ser Asp Ala Ile Pro Asn Phe Pro Phe Asn Gln Val Leu Phe His
    50                  55                  60

Lys Phe Ala Trp Lys Thr Ile Arg Lys Phe His Ile Asp Arg His Cys
65                  70                  75                  80

Tyr Arg His Ser Leu Gln Thr Gly Lys Met Ser Glu Ala Ile Ala Gln
                85                  90                  95

Ile Ser Arg Leu His Glu Gln Gln Leu Asp Arg Thr Arg Pro Leu Trp
            100                 105                 110

Glu Leu His Leu Phe Asp Asn Leu Glu Pro Glu Thr Gln Asn Gly Thr
        115                 120                 125

Arg Arg Phe Leu Leu Tyr Leu Lys Ala His His Ala Met Ile Asp Gly
    130                 135                 140

Val Ala Ala Met Arg Leu Phe Gln Arg Ser Leu Ser His Ser Pro Asp
145                 150                 155                 160

Glu Lys Leu Ser Lys Pro Ile Trp Leu Arg Asn Ile Arg Arg Lys Glu
                165                 170                 175

Ser Ser Phe Val Met Asp Lys Lys Pro Ile Val Glu His Phe Lys Asp
            180                 185                 190

Gln Ile Ala Gly Leu Lys Pro Val Tyr Gln Glu Leu Lys Ser Asp Tyr
        195                 200                 205

Gln Leu Ser Gln Ser Thr Ala Ser Gln Thr Pro Lys Thr Gln Phe Ile
    210                 215                 220

Ser Ser Leu Gln Ala Pro Ser Ser Ile Leu Asn Gln Arg Ile Gly Thr
225                 230                 235                 240

Ser Arg His Ile Cys Val Leu Thr Leu Lys Lys Ala Arg Phe Val Gln
                245                 250                 255

Val Ala Lys Arg Leu Asn Val Ser Thr Asn Asp Ile Ile Leu Ala Val
            260                 265                 270

Cys Ser Thr Ala Ile Arg Asn Tyr Leu Leu Ser Gln Asn Ala Leu Pro
        275                 280                 285

Asp Met Pro Leu Ile Ala Phe Val Pro Ile Ser Leu Arg Lys Asn Asp
    290                 295                 300

Thr Ala Leu Gly Asn Gln Ile Ser Phe Ile Pro Thr Asn Leu Gly Thr
305                 310                 315                 320

Asn Asn Pro Asp Ala Ile Ala Arg Leu Arg Leu Ile His Asp Ser Val
                325                 330                 335
```

```
Gln Ala Gly Lys Met Arg Ala Gly Arg Met Thr Gln Ala Glu Phe Ile
            340                 345                 350

Asn Tyr Thr Ala Val His Tyr Ala Trp Ala Gly Ile Asn Leu Ala Met
            355                 360                 365

Arg Leu Tyr Pro Ala Lys Gln Ala Phe Asn Leu Ile Ile Ser Asn Ile
    370                 375                 380

Pro Gly Asp Ser Thr Pro Leu Tyr Leu Asn Gly Ala Lys Leu Thr Ala
385                 390                 395                 400

Met Tyr Pro Ala Ser Val Leu Phe Asp Gly Gln Ala Leu Asn Ile Ser
            405                 410                 415

Phe Thr Asn Tyr Gln Asp Cys Ile Asp Phe Gly Ile Thr Ala Cys Gln
            420                 425                 430

Thr Ala Leu Pro Asn Ile Gln Ser Leu Pro Ser Leu Leu Thr Gln Ala
            435                 440                 445

Leu Val Glu Tyr Glu Gly Asn Asp Tyr Ser Ser Asn Gln Val
    450                 455                 460

<210> SEQ ID NO 33
<211> LENGTH: 474
<212> TYPE: PRT
<213> ORGANISM: gamma proteobacterium HdN1

<400> SEQUENCE: 33

Met Lys Ala Leu Ser Pro Leu Asp Gln Ile Phe Leu Trp Leu Glu Arg
1               5                   10                  15

Arg Gln Gln Pro Met His Val Ala Gly Leu Gln Leu Phe Glu Phe Pro
            20                  25                  30

Glu Gly Ala Gly Glu His Tyr Val Ser Glu Leu Ala Gln Trp Leu Arg
        35                  40                  45

Gln Phe Lys Lys Pro Ala Ala Pro Phe Asn Gln Arg Leu Thr Arg Arg
    50                  55                  60

Phe Gly Gln Pro Phe Trp Thr Glu Asp Lys Gln Phe Asp Leu Glu His
65                  70                  75                  80

His Phe Arg His Glu Ala Leu Pro Ala Pro Gly Arg Ile Arg Glu Leu
                85                  90                  95

Leu Thr Leu Val Ser Ser Glu His Ser Asn Leu Met Asp Arg Glu Arg
            100                 105                 110

Pro Met Trp Glu Tyr His Leu Ile Glu Gly Phe Gln Asp Arg Arg Phe
        115                 120                 125

Ala Val Tyr Cys Lys Ile His His Ser Met Met Asp Gly Ile Ser Ala
    130                 135                 140

Met Arg Thr Gly Thr Arg Ala Leu Thr Thr Asn Pro Asp Glu Tyr Asp
145                 150                 155                 160

Leu Pro Pro Val Trp Ala Arg His His His Lys Thr Leu Ser Ser Ala
                165                 170                 175

Ser Leu Pro Leu Pro Asn Pro Leu Asp Ile Ala Ser Ser Val Ala Lys
            180                 185                 190

Leu Thr Ala Gly Leu Asn Lys Gln Leu Ser Thr Ile Pro Thr Val Ala
        195                 200                 205

Arg Glu Ile Tyr Lys Ala Gly Glu Arg Ala Lys Thr Asp Pro Asp Phe
    210                 215                 220

Ile Ser Val Phe Gln Ala Pro His Thr Ile Leu Asn Asp Ser Ile Thr
225                 230                 235                 240

Gly Ser Arg Arg Phe Ala Ala Gln Ser Phe Ser Val Ala Arg Ile Ala
```

```
                245                 250                 255
Arg Ile Ala Lys Ala Phe His Ala Thr Leu Asn Asp Val Val Leu Ala
            260                 265                 270

Ile Cys Gly Ser Ala Leu Arg Asn Tyr Leu Ile Met Leu Arg Lys Leu
            275                 280                 285

Pro Asp Lys Pro Leu Ile Ala Met Val Pro Val Ser Leu Arg Lys Asp
            290                 295                 300

Glu Ser Ala Glu Gly Asn Gln Val Ala Met Ile Leu Ala Asn Leu Gly
305                 310                 315                 320

Thr His Ile Ala Asp Pro Ser Asp Arg Leu Gln Met Val Lys Ala Ser
                325                 330                 335

Val Arg Asn Ala Lys Lys Arg Phe Ala Gly Met Thr Pro Glu Glu Ile
                340                 345                 350

Thr Asn Tyr Thr Ala Leu Thr Leu Ala Pro Thr Gly Leu Asn Leu Met
                355                 360                 365

Thr Gly Leu Arg Pro Asp Trp Leu Ala Phe Asn Val Val Ile Ser Asn
                370                 375                 380

Val Pro Gly Pro Arg Asp Thr Leu Tyr Trp Asn Gly Ala Arg Leu Leu
385                 390                 395                 400

Gly Met Tyr Pro Val Ser Ile Ala Leu Asn His Val Ala Leu Asn Ile
                405                 410                 415

Thr Leu Thr Ser Tyr Cys Asp Gln Leu Glu Phe Gly Leu Ile Ala Cys
                420                 425                 430

Arg Arg Thr Met Pro Ser Met Gln Arg Met Leu Thr Tyr Ile Glu Asn
                435                 440                 445

Gly Leu Asn Glu Leu Glu Ile Ala Ala Asp Leu His Ser Cys Thr Ala
            450                 455                 460

Glu Glu Ser Glu Glu Arg Leu Ile His Ile
465                 470

<210> SEQ ID NO 34
<211> LENGTH: 473
<212> TYPE: PRT
<213> ORGANISM: Mycobacterium sp.

<400> SEQUENCE: 34

Met Phe Thr Arg Val Thr Ser Lys Arg Leu Ser Pro Leu Asp Ser Met
1               5                   10                  15

Phe Leu Ala Ala Glu Ser Pro Glu Thr Met Met His Val Ala Gly Leu
            20                  25                  30

Met Gln Phe Arg Pro Thr Ser Gly Asp Ala Gly Asp Ile Leu Asp Gln
        35                  40                  45

Leu Arg Asp Glu Ile Tyr Gly Ser Asn Glu Ile Glu Pro Pro Trp Asn
    50                  55                  60

Met Lys Leu Gln Thr Pro Trp Phe Leu Leu Asn Pro Leu Gln Arg Trp
65                  70                  75                  80

Val Glu Asp Pro Lys Phe Asp Val Met Tyr His Val Arg Arg Ser Ala
                85                  90                  95

Leu Pro Arg Pro Gly Asp Gln Arg Glu Leu Gly Ile Leu Ile Ser Arg
            100                 105                 110

Leu His Ala Arg Gln Leu Asp Leu Thr Arg Pro Pro Trp Glu Leu His
        115                 120                 125

Ile Ile Glu Gly Leu Asp Asp Gly Asn Val Ala Leu Tyr Val Lys Met
    130                 135                 140
```

```
His His Ser Leu Val Asp Gly Tyr Thr Ala Met Lys Thr Leu Ile Arg
145                 150                 155                 160

Ser Met Ser Thr Asp Pro Ser Asp Thr Asp Thr Pro Leu Phe Phe Arg
                165                 170                 175

Asn Pro Val Pro Lys Arg Glu Arg Lys Lys Asp Glu Lys Asp Ser Ser
                180                 185                 190

Leu Ile Pro Asp Ile Gly Gly Leu Leu Arg Ser Ile Thr Ser Glu Leu
                195                 200                 205

Ser Thr Val Ile Asp Leu Pro Ala Ala Phe Ala Lys Leu Ala Met Thr
            210                 215                 220

Ala Val Ser Arg Ser Asn Pro Leu Val Gly Pro Gly Gln Ala Pro His
225                 230                 235                 240

Thr Ile Phe Asn Gly Arg Ile Gly Arg Ser Arg Arg Phe Ala Thr Gln
                245                 250                 255

Gln Tyr Asp Ile Ala Arg Leu Arg Ala Val Ala Asp Ala Ala Gly Ala
                260                 265                 270

Thr Leu Asn Asp Val Ala Leu Ala Ile Cys Gly Gly Gly Leu Arg Asp
                275                 280                 285

Tyr Leu Leu Gly Leu Asp Ala Leu Pro Asp Lys Ser Leu Ile Ala Met
                290                 295                 300

Leu Pro Val Asn Ile Arg Pro Lys Asp Asp Pro Gly Gly Gly Asn Ala
305                 310                 315                 320

Val Gly Ala Ile Leu Ala Thr Leu Gly Thr Asp Leu Ala Asp Ala Arg
                325                 330                 335

Glu Arg Ile Glu Ala Ile Ser Ala Ser Thr Lys Ala Ala Lys Asp Gln
                340                 345                 350

Leu Ser Gly Met Thr Ser Thr Ala Ile Leu Ala Tyr Thr Ala Ala Leu
                355                 360                 365

Met Ala Pro Phe Leu Val Gln Thr Gly Ala Ala Thr Val Gly Ala Pro
370                 375                 380

Lys Val Ala Pro Ala Ser Tyr Asn Val Ile Leu Ser Asn Val Pro Gly
385                 390                 395                 400

Pro Asp Tyr Pro Leu Tyr Phe Arg Gly Asn Glu Leu Val Ser Thr Tyr
                405                 410                 415

Pro Val Ser Ile Pro Val His Gly Val Gly Leu Asn Ile Thr Cys Gln
                420                 425                 430

Ser Tyr Ser Gly Thr Leu Asn Phe Gly Phe Thr Gly Cys Arg Asp Ser
                435                 440                 445

Met Pro His Met Gln Lys Leu Ala Ile Lys Thr Gly Ala Ala Leu Val
                450                 455                 460

Ala Leu Glu Gln Ala Tyr Gly Leu Leu
465                 470
```

PRODUCTION OF FATTY ACIDS ESTERS

BACKGROUND OF THE INVENTION

Field of the Invention

The present invention relates to a biotechnological method and cell for producing at least one fatty acid ester from a sugar.

Discussion of the Background

Fatty acid esters may be used for several purposes commercially. For example, biodiesel, an alternative fuel, is comprised of esters (e.g., fatty acid methyl ester, fatty acid ethyl esters, etc.). Some low molecular weight esters are volatile with a pleasant odour which makes them useful as fragrances or flavouring agents. Fatty acid esters may also be used as solvents for lacquers, paints, varnishes and the like. Esters are also used as softening agents in resins and plastics, plasticizers, flame retardants, and additives in gasoline and oil. Further, esters can be used in the manufacture of polymers, films, textiles, dyes, and pharmaceuticals. Accordingly, fatty acid esters are very useful in this day and age.

Fatty acid esters may be extracted from petroleum. However, this method is energy consuming and costly. Also, it is an inefficient process because frequently the long chain hydrocarbons in crude petroleum are cracked to produce smaller monomers. These monomers are then used as the raw material to manufacture the more complex specialty chemicals. This process of cracking gasoline or petroleum is bad for the environment. Also, since the costs for these starting materials will be linked to the price of petroleum, with the expected increase in petroleum prices in the future, cost of making these fatty acid esters may also increase relative to the increase in the petroleum prices.

Due to the inherent challenges posed by petroleum, there is a need for a renewable petroleum source which does not need to be explored, extracted, transported over long distances, or substantially refined like petroleum. There is also a need for a renewable petroleum source that can be produced economically and that does not cause the environmental damage as that produced by the petroleum industry and the burning of petroleum based fuels.

Fatty acid esters may be found in several biofuels. However, the yield of the fatty acid esters from these biofuels and/or plant based fuels is low. Thus, a need exists to develop an alternate biological source of fatty acid esters. One option is to recombinantly engineer a microbial species for efficient production of fatty acid esters.

Fatty acid esters are known to be the product of a condensation reaction between an acyl-CoA molecule and an alcohol of any chain length sometimes in the presence of wax ester synthases. For example, a fatty acid ester can be the condensation product of methanol, ethanol, propanol, butanol, isobutanol, 2-methylbutanol, 3-methylbutanol, or pentanol with an acyl-CoA molecule. In some instances, fatty acid esters such as fatty acid methyl esters ("FAME") or fatty acid ethyl esters ("FAEE") can be produced by supplying the alcohol used in the reaction (e.g., methanol or ethanol) to the culture media. Similarly, wax esters can be produced by supplying fatty alcohols.

Most fatty acid esters have useful functions as mentioned above. One of these esters, methyl laurate, $CH_3(CH_2)_{10}COOCH_3$ a water-insoluble, clear, colourless ester, has several uses in the commercial industry including the pharmaceutical and cosmetic industry.

However, the current methods used to make fatty acid esters are inefficient as they produce a large amount of by-products that result in a waste of resources. Also, the currently available methods do not allow for selecting specific fatty acid esters. There is thus a need for more energy efficient and specific production of fatty acid esters including methyl laurate.

SUMMARY OF THE INVENTION

The present invention attempts to solve the problems above by providing at least one method of producing fatty acid esters from genetically engineered microorganisms. In particular, the fatty acid esters are produced by culturing a microorganism that is genetically engineered to produce a fatty acid and express at least one wax ester synthase, in the presence of exogenous alcohol, such as exogenous ethanol, exogenous methanol or the like.

In one embodiment, the present invention relates to a microbial cell for producing at least one fatty acid ester, wherein the cell is genetically modified to comprise
(i) at least one first genetic mutation that enables the cell to produce at least one fatty acid and/or acyl coenzyme A (CoA) thereof by increased enzymatic activity in the cell relative to the wild type cell of malonyl-CoA dependent and malonyl-ACP independent fatty acyl-CoA metabolic pathway, wherein the fatty acid comprises at least 5 carbon atoms; and
(ii) a second genetic mutation that increases the activity of at least one wax ester synthase in the cell relative to the wild type cell and the wax ester synthase has sequence identity of at least 50% to a polypeptide of SEQ ID NO: 1-8 and combinations thereof or to a functional fragment of any of the polypeptides for catalyzing the conversion of fatty acid and/or acyl coenzyme A thereof to the fatty acid ester.

In another embodiment, the present invention relates to a method for producing methyl laurate, the method comprising:
contacting lauric acid and/or lauroyl coenzyme A with an isolated wax ester synthase that has sequence identity of at least 50% to a polypeptide of SEQ ID NOs: 1-8 and combinations thereof.

The present invention also related to the above method, which is carried out within a microbial cell which is genetically modified to comprise
(i) at least one first genetic mutation that enables the cell to produce at least one fatty acid and/or acyl coenzyme A (CoA) thereof by increased enzymatic activity in the cell relative to the wild type cell of malonyl-CoA dependent and malonyl-ACP independent fatty acyl-CoA metabolic pathway, wherein the fatty acid comprises at least 5 carbon atoms; and
(ii) a second genetic mutation that increases the activity of at least one wax ester synthase in the cell relative to the wild type cell and the wax ester synthase has sequence identity of at least 50% to a polypeptide of SEQ ID NO: 1-8 and combinations thereof or to a functional fragment of any of the polypeptides for catalyzing the conversion of fatty acid and/or acyl coenzyme A thereof to the fatty acid ester.

DETAILED DESCRIPTION OF THE INVENTION

Figure 1:
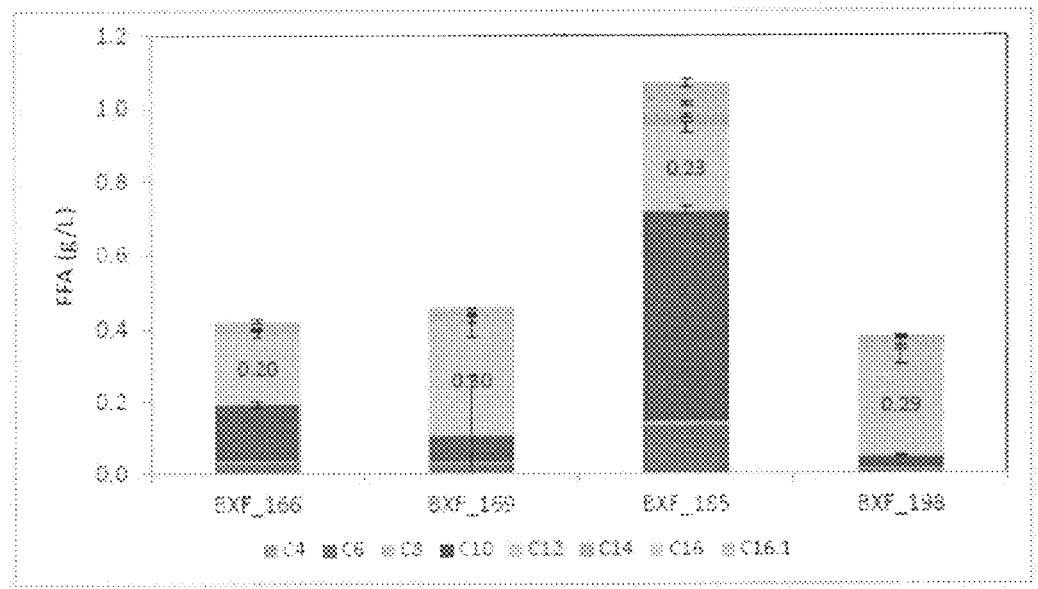
FIG. 1 is a graph showing free fatty acid (FFA) production in shake flask cultures after 68 hours for four FFA production strains.

The ranges described below include all values and sub-values between the lower and upper limit of the range.

According to one aspect, the present invention provides a microbial cell for producing at least one fatty acid ester, wherein the cell is genetically modified to comprise:
 at least one first genetic mutation that enables the cell to produce at least one fatty acid and/or acyl coenzyme A thereof, wherein the fatty acid comprises at least 5 carbon atoms; and
 at least one second genetic mutation that increases the activity of at least one wax ester synthase in the cell relative to the wild type cell and the wax ester synthase has sequence identity of at least 50% to a polypeptide of SEQ ID NOs: 1-8 and combinations thereof or to a functional fragment of any of the polypeptides for catalyzing the conversion of fatty acid and/or acyl coenzyme A thereof to the fatty acid ester.

In particular, the cell may be capable of producing the fatty acid and/or acyl coenzyme A thereof by means of increased enzymatic activity in the cell relative to the wild type cell of the malonyl-CoA dependent and malonyl-ACP independent fatty acyl-CoA metabolic pathway.

The microbial cells according to any aspect of the present invention may be prokaryotes or eukaryotes. These can be mammalian cells (such as, for example, cells from man), plant cells or microorganisms such as yeasts, fungi or bacteria, wherein microorganisms in particular bacteria and yeasts may be used.

Suitable bacteria, yeasts or fungi are in particular those bacteria, yeasts or fungi that are deposited in the Deutsche Sammlung von Mikroorganismen und Zellkulturen (German Collection of Microorganisms and Cell Cultures) GmbH (DSMZ), Brunswick, Germany, as bacterial, yeast or fungal strains.

Bacteria suitable according to the invention belong to the genera that are listed in the Deutsche Sammlung von Mikroorganismen und Zellkulturen (German Collection of Microorganisms and Cell Cultures) GmbH (DSMZ), Brunswick, Germany.

Yeasts suitable according to the invention belong to the genera that are listed in the Deutsche Sammlung von Mikroorganismen und Zellkulturen (German Collection of Microorganisms and Cell Cultures) GmbH (DSMZ), Brunswick, Germany.

Fungi suitable according to the invention belong to the genera that are listed in the Deutsche Sammlung von Mikroorganismen und Zellkulturen (German Collection of Microorganisms and Cell Cultures) GmbH (DSMZ), Brunswick, Germany.

In particular, the cells may be selected from the genera *Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium* and *Cupriavidus*. More in particular, the cells may be selected from the group consisting of *Aspergillus nidulans, Aspergillus niger, Alcaligenes latus, Bacillus megaterium, Bacillus subtilis, Brevibacterium flavum, Brevibacterium lactofermentum, Burkholderia andropogonis, B. brasilensis, B. caledonica, B. caribensis, B. caryophylli, B. fungorum, B. gladioli, B. glathei, B. glumae, B. graminis, B. hospita, B. kururiensis, B. phenazinium, B. phymatum, B. phytofirmans, B. plantarii,*

*B. sacchari, B. singaporensis, B. sordidicola, B. terricola, B. tropica, B. tuberum, B. ubonensis, B. unamae, B. xenovorans, B. anthina, B. pyrrocinia, B. thailandensis, Candida blankii, Candida rugosa, Corynebacterium glutamicum, Corynebacterium efficiens, Escherichia coli, Hansenula polymorpha, Kluveromyces lactis, Methylobacterium extorquens, Paracoccus versutus, Pseudomonas argentinensis, P. borbori, P. citronellolis, P. flavescens, P. mendocina, P. nitroreducens, P. oleovorans, P. pseudoalcaligenes, P. resinovorans, P. straminea, P. aurantiaca, P. aureofaciens, P. chlororaphis, P. fragi, P. lundensis, P. taetrolens, P. antarctica, P. azotoformans, 'P. blatchfordae', P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. proteolytica, P. rhodesiae, P. synxantha, P. thivervalensis, P. tolaasii, P. veronii, P. denitrificans, P. pertucinogena, P. cremoricolorata, P. fulva, P. monteilii, P. mosselii, P. parafulva, P. putida, P. balearica, P. stutzeri, P. amygdali, P. avellanae, P. caricapapayae, P. cichorii, P. coronafaciens, P. ficuserectae, 'P. helianthi', P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. psychrophila, P. psychrotolerans, P. rathonis, P. reptilivora, P. resiniphila, P. rhizosphaerae, P. rubescens, P. salomonii, P. segitis, P. septica, P. simiae, P. suis, P. thermotolerans, P. aeruginosa, P. tremae, P. trivialis, P. turbinellae, P. tuticorinensis, P. umsongensis, P. vancouverensis, P. vranovensis, P. xanthomarina, Ralstonia eutropha, Rhodospirillum rubrum, Rhodobacter sphaeroides, Saccharomyces cerevisiae, Yarrowia lipolytica* and *Zymomonas* mobile. More in particular, the cell may be a bacterial cell selected from the group consisting of *Pseudomonas, Corynebacterium, Bacillus* and *Escherichia*. Even more in particular, the cells may be selected from the group consisting of *Pseudomonas putida* and *Escherichia coli*.

The genetically modified cell may be genetically different from the wild type cell. The genetic difference between the genetically modified cell according to any aspect of the present invention and the wild type cell may be in the presence of a complete gene, amino acid, nucleotide etc. in the genetically modified cell that may be absent in the wild type cell. In one example, the genetically modified cell according to any aspect of the present invention may comprise enzymes that enable the cell to produce at least one fatty acid and/or acyl coenzyme A thereof; and convert the fatty acid and/or acyl coenzyme A thereof to the fatty acid ester. The wild type cell relative to the genetically modified cell of the present invention may have none or no detectable activity of the enzymes that enable the genetically modified cell to produce at least one fatty acid and/or acyl coenzyme A thereof; and the enzymes that enable genetically modified cell to convert the fatty acid and/or acyl coenzyme A thereof to the respective fatty acid ester.

The phrase "wild type" as used herein in conjunction with a cell may denote a cell with a genome make-up that is in a form as seen naturally in the wild. The term may be applicable for both the whole cell and for individual genes. The term "wild type" therefore does not include such cells or such genes where the gene sequences have been altered at least partially by man using recombinant methods.

A skilled person would be able to use any method known in the art to genetically modify a cell. According to any aspect of the present invention, the genetically modified cell may be genetically modified so that in a defined time interval, within 2 hours, in particular within 8 hours or 24 hours, it forms at least twice, especially at least 10 times, at least 100 times, at least 1000 times or at least 10000 times more fatty acid and/or acyl coenzyme A thereof and the respective fatty acid ester than the wild-type cell. The increase in product formation can be determined for example by cultivating the cell according to any aspect of the present invention and the wild-type cell each separately under the same conditions (same cell density, same nutrient medium, same culture conditions) for a specified time interval in a suitable nutrient medium and then determining the amount of target product (fatty acid, acyl coenzyme A thereof and the respective fatty acid ester) in the nutrient medium.

In particular, the cell comprises at least one first genetic mutation that enables the cell to produce at least one fatty acid and/or acyl coenzyme A thereof. In particular, the first genetic mutation may enable the cell to produce at least one fatty acid and/or acyl coenzyme A thereof by means of a malonyl-CoA dependent and malonyl-ACP independent fatty acyl-CoA metabolic pathway. More in particular, there is an increase in enzymatic activity in the malonyl-CoA dependent and malonyl-ACP independent fatty acyl-CoA metabolic pathway in the cell relative to the wild type cell.

The cell may be genetically modified for increased enzymatic activity in the microorganism's malonyl-CoA dependent, malonyl-ACP independent, fatty acyl-CoA metabolic pathway ("MDMIFAA") This pathway is also referred to herein as malonyl-CoA dependent, but malonyl-ACP independent, fatty acyl-CoA metabolic pathway. Such increase in the cell's malonyl-CoA dependent, malonyl-ACP independent fatty acyl-CoA metabolic pathway can be achieved by an increased activity or expression of a gene or a pathway comprising an acetoacetyl-CoA synthase, a ketoacyl-CoA synthase (or elongase), an enoyl-CoA reductase, a ketoacyl-CoA reductase and/or a 3-hydroxyacyl-CoA dehydratase in combination with a decrease in expression or activity of acetoacetyl-CoA thiolase. Alternatively, increased activity in the microorganism's malonyl-CoA dependent, malonyl-ACP independent fatty acyl-CoA metabolic pathway can be achieved by an increased expression of a gene or a pathway comprising an acetoacetyl-CoA synthase, a ketoacyl-CoA thiolase, a enoyl-CoA reductase, a ketoacyl-CoA reductase and/or a 3-hydroxyacyl-CoA dehydratase in combination with a decrease in expression or activity of acetoacetyl-CoA thiolase.

A list of non-limiting genetic modifications to enzymes or enzymatic activities that may lead a cell to produce a fatty acid and/or acyl coenzyme A thereof and that may be considered as the first genetic mutation according to any aspect of the present invention are provided below in Table 1 and explained in US20140051136.

Figure 11:
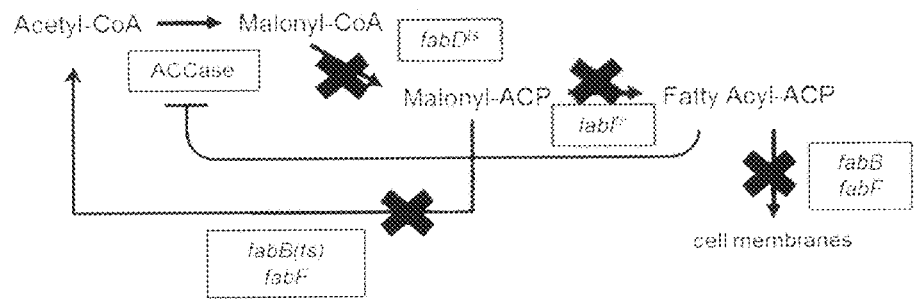
FIG. 11 is an illustration of the metabolic pathways of a cell related to genetic modifications for increasing flux through the intermediate malonyl-CoA

In particular, fatty acid biosynthetic pathways in the cells of the present invention use precursors acetyl-CoA and malonyl-CoA. The enzymes that may be involved are provided in FIG. 11.

In one example, nucleic acid sequences that encode temperature-sensitive forms of these polypeptides may be introduced in place of the native enzymes, and when such genetically modified microorganisms are cultured at elevated temperatures (at which these thermolabile polypeptides become inactivated, partially or completely, due to alterations in protein structure or complete denaturation), there is observed an increase in a chemical product. For example, in *E. coli*, these temperature-sensitive mutant genes could include Fablts(S241F), FabBts(A329V) or Fab-Dts(W257Q) amongst others. In most of these examples, the genetic modifications may increase malonyl-CoA utilization so that there is a reduced conversion of malonyl-CoA to fatty acids via the native pathway, overall biomass, and proportionally greater conversion of carbon source to a chemical product including a fatty acid or fatty acid derived product via a malonyl-CoA dependent and malonyl-ACP independent route. Also, additional genetic modifications, such as to increase malonyl-CoA production, may be made for some examples.

In another example, the enzyme, enoyl-acyl carrier protein reductase (EC No. 1.3.1.9, also referred to as enoyl-ACP reductase) is a key enzyme for fatty acid biosynthesis from malonyl-CoA. In *Escherichia coli* this enzyme, FabI, is encoded by the gene FabI (Richard J. Heath et al., 1995).

In one example, the expression levels of a pyruvate oxidase gene (Chang et al., 1983, Abdel-Ahmid et al., 2001) can be reduced or functionally deleted in the cell according to any aspect of the present invention. The pyruvate oxidase gene may encode an enzyme of, for example, EC 1.2.3.3. In particular, the pyruvate oxidase gene may be a PoxB gene.

In one example, the expression levels of a lactate dehydrogenase gene (Mat-Jan et al., Bunch et al., 1997) can be reduced or functionally deleted. In some examples, the lactate dehydrogenase gene encodes an enzyme of, for example, EC 1.1.1.27. The lactate dehydrogenase gene may be an NAD-linked fermentative D-lactate dehydrogenase gene. In particular, the lactate dehydrogenase gene is an ldhA gene.

In one example, the first genetic mutation may be in at least one feedback resistant enzyme of the cell that results in increased expression of the feedback resistant enzyme. In particular, the enzyme may be pantothenate kinase, pyruvate dehydrogenase or the like. In *E. coli*, these feedback resistant mutant genes could include CoaA(R106A) and/or lpd (E354K).

In a further example, the increase in the cell's malonyl-CoA dependent, but malonyl-ACP independent fatty acyl-CoA metabolic pathway may occur through reduction in the acetoacetyl-CoA thiolase activity and/or trigger factor activity and/or in the activity of a molecular chaperone involved in cell division. In one example, the cell may comprise a genetic mutation in Ttig gene.

In one example, the first genetic mutation in the cell may result in increased enzymatic activity in the NADPH-dependent transhydrogenase pathway relative to the wild type cell. This result may occur by introduction of a heterologous nucleic acid sequence coding for a polypeptide encoding nucleotide transhydrogenase activity.

In another example, the first genetic mutation in the cell may result in decreased expression of fatty acyl-CoA synthetase and/or ligase activity via any method known in the art.

In yet another example, the first genetic mutation in the cell may result in overexpression of an enzyme having acetyl-CoA carboxylase activity.

In one example, the cell may have increased intracellular bicarbonate levels brought about by introduction of a heterologous nucleic acid sequence coding for a polypeptide having cyanase and/or carbonic anhydrase activity.

More in particular, the first genetic mutation according to any aspect of the cell may result in increased and/or decreased levels of fatty acyl-CoA thioesterase activity. This result may increase chain length specificity of a desired fatty acid product by increasing levels of chain length specific fatty acyl-CoA thioesterase activity and decreasing the activity of fatty acyl-CoA thioesterase activity on undesired fatty acid chain lengths. In one example, the increased chain length specificity of fatty acid or fatty acid derived product may occur by increasing levels of chain length specific ketoacyl-CoA thiolase, enoyl-CoA reductase, ketoacyl-CoA reductase or 3-hydroxyacyl-CoA dehydratase activities either individually or in combination.

The first genetic mutation in the cell according to any aspect of the present invention may result in an increase or decrease in expression of only one enzyme selected from the list of enzymes mentioned above or an increase or decrease in expression of a combination of enzymes mentioned above.

In another example, the first genetic mutation in the cell may be in at least one enzyme selected from the group consisting of acetoacetyl-CoA synthase, ketoacyl-CoA synthase (or elongase), enoyl-CoA reductase, ketoacyl-CoA reductase, 3-hydroxyacyl-CoA dehydratase and acetoacetyl-CoA thiolase. More in particular, the first genetic mutation in the cell may result in an increase in expression of acetoacetyl-CoA synthase, ketoacyl-CoA synthase (or elongase), enoyl-CoA reductase, ketoacyl-CoA reductase and 3-hydroxyacyl-CoA dehydratase in combination optionally with a decrease in expression or activity of acetoacetyl-CoA thiolase. In particular, the enoyl-CoA reductase and/or ketoacyl-CoA reductase may either utilize the cofactor NADH and/or NADPH. In particular, the genetic modification in the cell according to any aspect of the present invention may comprise any of the enzymes listed in Table 1 in combination with the following enzymes acetoacetyl-CoA synthase, ketoacyl-CoA synthase (or elongase), enoyl-CoA reductase, ketoacyl-CoA reductase and/or 3-hydroxyacyl-CoA dehydratase and acetoacetyl-CoA thiolase wherein the expression or activity of enzymes acetoacetyl-CoA synthase, ketoacyl-CoA synthase (or elongase), enoyl-CoA reductase, ketoacyl-CoA reductase and 3-hydroxyacyl-CoA dehydratase is increased and the activity of acetoacetyl-CoA thiolase is decreased.

In yet another example, malonyl-CoA dependent, malonyl-ACP independent fatty acyl-CoA metabolic pathway in the cell according to any aspect of the present invention can be achieved by an increased expression of a gene or a pathway comprising acetoacetyl-CoA synthase, ketoacyl-CoA thiolase, enoyl-CoA reductase, ketoacyl-CoA reductase and/or 3-hydroxyacyl-CoA dehydratase in combination with a decrease in expression or activity of acetoacetyl-CoA thiolase.

In particular, the first genetic modification in the cell according to any aspect of the present invention may comprise any of the enzymes listed in Table 1 in combination with the following enzymes acetoacetyl-CoA synthase, ketoacyl-CoA thiolase, enoyl-CoA reductase, ketoacyl-CoA reductase and/or 3-hydroxyacyl-CoA dehydratase in combination with a decrease in expression or activity of acetoacetyl-CoA thiolase.

In one example, the cell according to any aspect of the present invention may comprise a first genetic modification in any of the enzymes listed in Table 1 in combination with the following enzymes acetyl-CoA carboxylase, malonyl-CoA:ACP transacylase (FabD), β-ketoacyl-ACP synthase III, β-ketoacyl-ACP synthase I (FabB), β-ketoacyl-ACP synthase II (FabF), 3-oxoacyl-ACP-synthase I and enoyl ACP reductase.

More in particular, the first genetic mutation may result in an increase in the expression of at least one enzyme selected from the group consisting of acetyl-CoA carboxylase, malonyl-CoA:ACP transacylase (FabD), β-ketoacyl-ACP synthase III, β-ketoacyl-ACP synthase I (FabB), β-ketoacyl-ACP synthase II (FabF), 3-oxoacyl-ACP-synthase I and enoyl ACP reductase relative to the wild type cell. In particular, the first genetic mutation may result in an increase in the expression of more than one enzyme in the cell according to any aspect of the present invention that enables the cell to produce a fatty acid and/or acyl coenzyme A thereof by means of increased enzymatic activity in the cell relative to the wild type cell of malonyl-CoA dependent and malonyl-ACP independent fatty acyl-CoA metabolic pathway.

In one example, there may be an increase in expression of β-ketoacyl-ACP synthase and 3-oxoacyl-ACP-synthase in the cell according to any aspect of the present invention. In another example, there may be an increase in expression of β-ketoacyl-ACP synthase and Malonyl-CoA-ACP transacylase in the cell according to any aspect of the present invention. In yet another example, there may be an increase in expression of β-ketoacyl-ACP synthase and enoyl ACP reductase in the cell according to any aspect of the present invention. In one example, there may be an increase in expression of β-ketoacyl-ACP synthase, Malonyl-CoA-ACP transacylase and enoyl ACP reductase in the cell according to any aspect of the present invention. In all examples, there may be an increase in the expression of enoyl ACP reductase and/or acyl-CoA thioesterase.

The phrase "increased activity of an enzyme", as used herein is to be understood as increased intracellular activity. Basically, an increase in enzymatic activity can be achieved by increasing the copy number of the gene sequence or gene sequences that code for the enzyme, using a strong promoter or employing a gene or allele that code for a corresponding enzyme with increased activity and optionally by combining these measures. Genetically modified cells used according to any aspect of the present invention are for example produced by transformation, transduction, conjugation or a combination of these methods with a vector that contains the desired gene, an allele of this gene or parts thereof and a vector that makes expression of the gene possible. Heterologous expression is in particular achieved by integration of the gene or of the alleles in the chromosome of the cell or an extra-chromosomally replicating vector.

Accordingly, the cells and methods of the present invention may comprise providing a genetically modified microorganism that comprises both a production pathway to a fatty acid or fatty acid derived product, and a modified polynucleotide that encodes an enzyme of the malonyl-ACP dependent fatty acid synthase system that exhibits reduced activity, so that utilization of malonyl-CoA shifts toward the production pathway compared with a comparable (control) microorganism lacking such modifications. The methods involve producing the chemical product using a population of such genetically modified microorganism in a vessel, provided with a nutrient media. Other genetic modifications described herein, to other enzymes, such as acetyl-CoA carboxylase and/or NADPH-dependent transhydrogenase, may be present in some such examples. Providing additional copies of polynucleotides that encode polypeptides exhibiting these enzymatic activities is shown to increase a fatty acid or fatty acid derived product production. Other ways to increase these respective enzymatic activities is known in the art and may be applied to various examples of the present invention.

TABLE 1

Examples of genetic modifications in cells of microorganisms for production of fatty acids and/or acyl coenzyme A thereof
Genetic Modifications

| ENZYME FUNCTION | E.C. CLASSIFICATION No. | GENE NAME IN E. COLI | COMMENTS |
| --- | --- | --- | --- |
| Glucose transporter | N/A | galP | Increase function |
| Pyruvate dehydrogenase E1p | 1.2.4.1 | aceE | Increase function |
| lipoate acetyltransferase/ dihydrolipoamide acetyltransferase | 2.3.1.12 | aceF | Increase function |
| Pyruvate dehydrogenase E3 (lipoamide dehydrogenase) | 1.8.1.4 | lpd | Increase function or alter such as by mutation to increase resistance to NADH inhibition. |
| Lactate dehydrogenase | 1.1.1.28 | ldhA | Decrease function, including by mutation |
| Pyruvate formate lyase (B "inactive") | 2.3.1.— | pflB | Decrease function, including by mutation |
| Pyruvate oxidase | 1.2.2.2 | poxB | Decrease function, including by mutation |
| Phosphate acetyltransferase | 2.3.1.8 | Pta | Decrease function, including by mutation |
| acetate kinase | 2.7.2.15 2.7.2.1 | ackA | Decrease function, including by mutation |
| methylglyoxal synthase | 4.2.3.3 | mgsA | Decrease function, including by mutation |
| Heat stable, histidyl phoshorylatable protein (of PTS) | N/A | ptsH (HPr) | Decrease function, including by mutation |
| Phosphoryl transfer protein (of PTS) | N/A | ptsI | Decrease function, including by mutation |
| Polypeptide chain (of PTS) | N/A | Crr | Decrease function, including by mutation |

TABLE 1-continued

Examples of genetic modifications in cells of microorganisms for
production of fatty acids and/or acyl coenzyme A thereof
Genetic Modifications

| ENZYME FUNCTION | E.C. CLASSIFICATION No. | GENE NAME IN E. COLI | COMMENTS |
|---|---|---|---|
| 3-oxoacyl-ACP synthase I | 2.3.1.179 | fabF | Decrease function, including by mutation |
| 3-oxoacyl-ACP synthase II monomer | 2.3.1.41 | | |
| β-ketoacyl-ACP sythnase I. | 2.3.1.41 | fabB | Decrease function, including by mutation |
| 3-oxoacyl-AC-synthase I | 2.3.1.— | | |
| Malonyl-CoA-ACP transacylase | 2.3.1.39 | fabD | Decrease function, including by mutation |
| enoyl acyl carrier protein reductase | 1.3.1.9. 1.3.1.10 | fabI | Decrease function, including by mutation |
| β-ketoacyl-acyl carrier protein synthase III | 2.3.1.180 | fabH | Decrease function, including by mutation |
| Carboxyl transferase subunit α subunit | 6.4.1.2 | accA | Increase function |
| Biotin carboxyl carrier protein | 6.4.1.2 | accB | Increase function |
| Biotin carboxylase subunit | 6.3.4.14 | accC | Increase function |
| Carboxyl transferase subunit β subunit | 6.4.1.2 | accD | Increase function |
| long chain fatty acyl thioesterase I | 3.1.2.2. 3.1.1.5 | tesA | Increase function as well as alter by mutation to express in cytoplasm or deletion |
| acyl-CoA synthase | 2.3.1.86 | fadD | Decrease via deletion or mutation |
| acetate CoA-transferase | 2.8.3.8 | atoD | Decrease via deletion or mutation |
| acetate CoA-transferase | 2.8.3.8 | atoA | Decrease via deletion or mutation |
| Transporter | N/A | atoE | Decrease via deletion or mutation |
| acetyl-CoA acetyltransferase | 2.3.1.9 | atoB | Decrease via deletion or mutation |
| pantothenate kinase | 2.7.1.33 | coaA | Increase via expression or feedback resisant mutation |
| lactose repressor | N/A | lacI | Decrease via deletion or mutation |
| γ-glutamyl-γ-aminobutyraldehye dehydrogenase | 1.2.1.— | puuC | Decrease via deletion or mutation |
| malate synthase A | 2.3.3.9 | aceB | Decrease via deletion or mutation |
| isocitrate lyase | 4.1.3.1 | aceA | Decrease via deletion or mutation |
| isocitrate dehydrogenase phosphatase/isocitrate dehydrogenase kinase | 3.1.3.— 2.7.11.5. | aceK | Decrease via deletion or mutation |
| pyruvate formate-lyase deactivate | 1.2.1.10 1.1.1.1 | adhE | Decrease via deletion or mutation |
| aldehyde dehydrogenase A. NAD-linked | 1.2.1.21 1.2.1.22 | aldA | Decrease via deletion or mutation |
| acetaldehyde dehydrogenase | 1.2.1.4 | aldB | Decrease via deletion or mutation |
| Lambda phage DE3 lysogen | N/A | λDE2 | Increase |
| T7 mRNA polymerase | N/A | T7pol | Increase |
| trigger factor | 5.2.1.8 | tig | Decrease via deletion or mutation |
| 3-ketoacyl-CoA thiolase | 2.3.1.16 | fadA | Increase |
| dodecenoyl-CoA δ-isomerase, enoyl-CoA hydratase, 3-hydroxybutyryl-CoA epimerase, 3-hydroxyacyl-CoA dehydrogenase | 5.3.3.8 1.1.1.35 5.1.2.3 4.2.1.17 | fadB | Increase |
| Sucrose permease | N/A | cscB | Increase |
| Invertase | 3.2.1.26 | cscA | Increase |
| fructokinase | 2.7.1.4 | cscK | Increase |
| carbonic anhydrase | 4.2.1.1 | cynT | Increase |

TABLE 1-continued

Examples of genetic modifications in cells of microorganisms for
production of fatty acids and/or acyl coenzyme A thereof
Genetic Modifications

| ENZYME FUNCTION | E.C. CLASSIFICATION No. | GENE NAME IN E. COLI | COMMENTS |
|---|---|---|---|
| carbonic anhydrase | 4.2.1.1 | can | Increase |
| pyridine nucleotide transhydrogenase | 1.6.1.2 | pntAB | Increase |
| pyridine nucleotide transhydrogenase | 1.6.1.1 | udhA | Increase |
| acyl-CoA thioesterase | 3.1.2.20 3.1.2.2 | yciA | Increase and or decrease |
| thioesterase II | 3.1.2.20 3.1.2.2 | tesB | Increase and or decrease |
| thioesterase III | 3.1.2.— | fadM | Increase and or decrease |
| hydroxyphenylacetyl-CoA thioesterase | N/A | paaI | Increase and or decrease |
| esterase/thioesterase | 3.1.2.28 | ybgC | Increase and or decrease |
| proofreading thioesterase in enterobactin biosynthesis | | entH | Increase and or decrease |
| acetoacetyl-CoA synthase | 2.3.1.194 | npth07 | Increase |
| 3-ketoacyl-CoA synthase/elongase | 2.3.1 | Elo1 | Increase |
| 3-ketoacyl-CoA synthase/elongase | 2.3.1 | Elo2 | Increase |
| 3-Hydroxybutyryl-CoA dehydrogenase | 1.1.1.157 | hbd | Increase |
| 3-oxoacyl-CoA reductase | 1.1.1.100 | fabG | Increase |
| enoyl-CoA hydratase | 4.2.1.17 | crt | Increase |
| enoyl-CoA hydratase | 4.2.1.17 | ech2 | Increase |
| Trans-2-enoyl-reductase | 1.3.1.9 | ter | Increase |
| thioesterase | 3.1.2.20 | paaI | Decrease |

E.C. No = "Enzyme Commission number"

Also, without being limiting, a first step in some multiphase methods of making a fatty acid may be exemplified by providing into a vessel, such as a culture or bioreactor vessel, a nutrient media, such as a minimal media as known to those skilled in the art, and an inoculum of a genetically modified microorganism so as to provide a population of such microorganism, such as a bacterium, and more particularly a member of the family Enterobacteriaceae, such as E. coli, where the genetically modified microorganism comprises a metabolic pathway that converts malonyl-CoA to a fatty acid. This inoculum is cultured in the vessel so that the cell density increases to a cell density suitable for reaching a production level of a fatty acid or fatty acid derived product that meets overall productivity metrics taking into consideration the next step of the method. In various alternative embodiments, a population of these genetically modified microorganisms may be cultured to a first cell density in a first, preparatory vessel, and then transferred to the noted vessel so as to provide the selected cell density. Numerous multi-vessel culturing strategies are known to those skilled in the art. Any such examples provide the selected cell density according to the first noted step of the method.

Also without being limiting, a subsequent step may be exemplified by two approaches, which also may be practiced in combination in various examples. A first approach provides a genetic modification to the genetically modified microorganism such that its enoyl-ACP reductase enzymatic activity may be controlled. As one example, a genetic modification may be made to substitute a temperature-sensitive mutant enoyl-ACP reductase (e.g., fabI$^{TS}$ in E. coli) for the native enoyl-ACP reductase. The former may exhibit reduced enzymatic activity at temperatures above 30° C. but normal enzymatic activity at 30° C., so that elevating the culture temperature to, for example to 34° C., 35° C., 36° C., 37° C. or even 42° C., reduces enzymatic activity of enoyl-ACP reductase. In such case, more malonyl-CoA is converted to a fatty acid than at 30° C., where conversion of malonyl-CoA to fatty acids is not impeded by a less effective enoyl-ACP reductase.

Other genetic modifications that may be useful in the production of fatty acids may be included in the cell. For example, the ability to utilize sucrose may be provided, and this would expand the range of feed stocks that can be utilized to produce a fatty acid or fatty acid derived product or other chemical products. Common laboratory and industrial strains of E. coli, such as the strains described herein, are not capable of utilizing sucrose as the sole carbon source. Since sucrose, and sucrose-containing feed stocks such as molasses, are abundant and often used as feed stocks for the production by microbial fermentation, adding appropriate genetic modifications to permit uptake and use of sucrose may be practiced in strains having other features as provided herein. Various sucrose uptake and metabolism systems are known in the art (for example, U.S. Pat. No. 6,960,455).

Also, genetic modifications may be provided to add functionality for breakdown of more complex carbon sources, such as cellulosic biomass or products thereof, for uptake, and/or for utilization of such carbon sources. For example, numerous cellulases and cellulase-based cellulose degradation systems have been studied and characterized (Beguin, P and Aubert, J-P, 1994; Ohima, K. et al., 1997.)

In some examples, genetic modifications increase the pool and availability of the cofactor NADPH, and/or, consequently, the NADPH/NADP$^+$ ratio may also be provided. For example, in E. coli, this may be done by increasing activity, such as by genetic modification, of one or more of the following genes: pgi (in a mutated form), pntAB, overexpressed, gapA:gapN substitution/replacement, and disrupting or modifying a soluble transhydrogenase such as sthA, and/or genetic modifications of one or more of zwf, gnd, and edd.

Any such genetic modifications may be provided to species not having such functionality, or having a less than desired level of such functionality. More generally, and depending on the particular metabolic pathways of a microorganism selected for genetic modification, any subgroup of genetic modifications may be made to decrease cellular production of fermentation product(s) selected from the group consisting of acetate, acetoin, acetone, acrylic, malate, fatty acid ethyl esters, isoprenoids, glycerol, ethylene glycol, ethylene, propylene, butylene, isobutylene, ethyl acetate, vinyl acetate, other acetates, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fusel alcohols, and 1,2-propanediol, 1,3-propanediol, formate, fumaric acid, propionic acid, succinic acid, valeric acid, and maleic acid. Gene deletions may be made as disclosed generally herein, and other approaches may also be used to achieve a desired decreased cellular production of selected fermentation products.

The first genetic mutation according to any aspect of the present invention may result in the formation of at least one fatty acid and/or acyl coenzyme A (CoA) thereof, wherein the fatty acid comprises at least 5 carbon atoms. In particular, the fatty acid may be of any chain length from 5 to greater than 18 carbons. The fatty acid may be selected from the group consisting of: pentanoic acid, hexanoic acid, octanoic acid, decanoic acid, dodecanoic acid, myristic acid, palmitic acid, palmitoleic acid, stearic acid, and oleic acid. In particular, these fatty acids may be produced from a fatty acyl-CoA intermediate via the activity of a fatty acyl-CoA thioesterase. Alternatively, these fatty acids may be produced from a fatty acyl-CoA intermediate via concerted activities of a fatty acyl-CoA phosphotransferase first producing a fatty acyl-phosphate and then the action of a fatty acid kinase operating to produce a fatty acid from the fatty acyl-phosphate.

According to any aspect of the present invention the cell according to any aspect of the present invention may be combined with a carbon source to be able to produce the fatty acid. In particular, the carbon source provided to the cell may have a ratio of carbon-14 to carbon-12 of about $1.0 \times 10^{-14}$ or greater. The carbon source may be selected from the group consisting of glucose, sucrose, fructose, dextrose, lactose, xylose, pentose, polyol, hexose, other cellulosic sugars or a combination thereof. In one example, the carbon source may be glycerol. In another example, the carbon source may be synthesis gas. Synthesis gas can for example be produced as a by-product of coal gasification. Accordingly, the microorganism according to any aspect of the present invention may be capable of converting a substance which is a waste product into a valuable resource.

In another example, synthesis gas may be a by-product of gasification of widely available, low-cost agricultural raw materials for use with the mixed culture of the present invention to produce substituted and unsubstituted organic compounds. There are numerous examples of raw materials that can be converted into synthesis gas, as almost all forms of vegetation can be used for this purpose. In particular, raw materials are selected from the group consisting of perennial grasses such as miscanthus, corn residues, processing waste such as sawdust and the like.

In general, synthesis gas may be obtained in a gasification apparatus of dried biomass, mainly through pyrolysis, partial oxidation and steam reforming, wherein the primary products of the synthesis gas are CO, $H_2$ and $CO_2$. Usually, a portion of the synthesis gas obtained from the gasification process is first processed in order to optimize product yields, and to avoid formation of tar. Cracking of the undesired tar and CO in the synthesis gas may be carried out using lime and/or dolomite. These processes are described in detail in for example, Reed, 1981.

In particular, the cell culture may comprise an inhibitor of fatty acid synthase the cell may be genetically modified for reduced enzymatic activity in the cell's fatty acid synthase pathway. This may allow better control for producing the specific desired fatty acid.

The cell according to any aspect of the present invention may comprise at least one second genetic mutation that may increase the activity of at least one wax ester synthase in the cell relative to the wild type cell. The wax ester synthase may comprise sequence identity of at least 50% to a polypeptide of SEQ ID NOs: 1-23 and combinations thereof or to a functional fragment of any of the polypeptides for catalyzing the conversion of fatty acid and/or acyl coenzyme A thereof to the respective fatty acid ester. In particular, the wax ester synthase may comprise sequence identity of at least 50% to a polypeptide of SEQ ID NOs: 1-8 and combinations thereof. More in particular, the wax ester synthase used according to any aspect of the present invention may comprise sequence identity of at least 60, 65, 70, 75, 80, 85, 90, 95, 98 or 100% to a polypeptide of any one of sequences of SEQ ID NOs: 1-8 and combinations thereof. These sequences are only reference amino acid sequences. In particular, the sequence of the wax ester synthase used according to any aspect of the present invention may comprise amino acids other than those essential for the function, for example the catalytic activity of a protein, or the fold or structure of a molecule are deleted, substituted or replaced by insertions or essential amino acids are replaced in a conservative manner to the effect that the biological activity of the reference sequence or a molecule derived therefrom is preserved. The state of the art comprises algorithms that may be used to align two given amino acid sequences and to calculate the degree of identity, see Arthur Lesk (2008), and Katoh et al., 2005. In particular, the wax ester synthase sequences used according to any aspect of the present invention may comprise the amino acids that provide the function to the protein. More in particular, the wax ester synthase sequences may comprise deletions, insertions or substitutions in amino acid sequences as well as fusions that still retain the function of the wax ester synthase capable of catalyzing the conversion of fatty acid and/or acyl coenzyme A thereof to the respective fatty acid ester. In one example, a mutant of any one of the sequences of SEQ ID NO:1-8 may be used in any aspect of the present invention. A 'mutant' used herein indicates a mutant derived from any one of the sequences of SEQ ID NO:1-8 that is capable of maintaining the function of a wax ester synthase of converting a fatty acid and/or acyl coenzyme A thereof to the respective fatty acid ester. Such a mutant has an amino acid sequence subjected to deletion, substitution, insertion, or addition of at least one amino acid. The mutant of the present invention can be adequately produced with the use of any methods known to persons skilled in the art.

TABLE 2

Sequence of wax ester synthases

| SEQ ID NO: | Accession No. (NCBI) | Organism | Sequence |
|---|---|---|---|
| 1 (Svar) | 522136843 | Singularimonas variicoloris | MESPRTPMHVGGLMTFRLPPD APPDFLRQLFARLRAQMPSTEP FNLRLARTPWSALAPAWEPAP DIDIDYHVRHSALPYPGGEREL GVLVSRLHSHPLDLRRPPWEIT LIEGLENDRFAFFLKVHHSALD GMGALKLVRRWLSADALQRD MPALWALPAQPREARDAPHGH AVEQGVEALRTQLRASGELLST LRRMARRRDNPEGGILSALSTP RTLLNVPITPQRRLATQLFELSR IKAVSAATQSTVNDVALALIAG AVRRYLLELDALPHEPLVASVP VGLPRADGKPGNAVAGFVVPL ETQADDPLDCLHVVRAVTQRT KDQLRGMSPEALAQFTMLGLS PLILGQMARVLSHLPPIFNFVVS NVVASKELLYLEGAELEAMYPI SVLFDGYALNVTLVGYHDRLS LGFTGCRDALPSLQRLAVYSAE ALEELERAAGLVPHAAGAAEH APARRTRRRGAH |
| 2 (Hche) | YP_436128.1 | Hahella chejuensis KCTC 2396 | MTPLSPVDQIFLWLEKRQQPM HVGGLHIFSFPDDADAKYMTEL AQQLRAYATPQAPFNRRLRQR WGRYYWDTDAQFDLEHHFRH EALPKPGRIRELLAHVSAEHSN LMDRERPMWECHLIEGIRGRRF AVYYKAHHCMLDGVAAMRM CVKSYSFDPTATEMPPIWAISK DVTPARETQAPAAGDLVHSLS QLVEGAGRQLATVPTLIRELGK NLLKARDDSDAGLIFRAPPSILN QRITGSRRFAAQSYALERFKAI GKAFQATVNDVVLAVCGSALR NYLLSRQALPDQPLIAMAPMSI RQDDSDSGNQIAMILANLGTHI ADPVRRLELTQASARESKERFR QMTPEEAVNYTALTLAPSGLNL LTGLAPKWQAFNVVISNVPGPN KPLYWNGARLEGMYPVSIPVD YAALNITLVSYRDQLEFGFTAC RRTLPSMQRLLDYIEQGIAELE KAAGV |
| 3 (Ajun) | 480024154 | Acinetobacter junii NIPH 182 | MRPLHPIDFIFLSLEKRQQPMH VGGLFLFEIPENASPTFVHDLVQ DIRQSKSIPVPPFNNQLNGLFW GEDPEFDIDHHFRHIALPNPGRI RELLVYISQQHSSLIDRAKPLW TCDIIEGIEGNRFAMYFKIHHA MVDGVAGMRLIEKSLSKDPNE KHVVPLWCVEGKRTKRLKAPK PPSVSKIKGIMDGIKSQLEVTPK VMQELSQTIFKEIGKNPDYVST FQAPPSILNQRVSSSRRFAAQSF ELDRFRNIAKSLGVTINDVVLA VCAGALREYLISHESLPKKPLIA MVPASLRTDDSDVSNRITMILA NLATHIEDPIERLQIIRRSVQNSK QRFSRMTANEILNYSALVYGPA GLNIVSGMLPKRQAFNLVISNV PGPREPLYWNGAKLDALYPASI VMDGQALNITMTSYLDKLEVG LIACRNALPKMQNLLTHLEDEI QRFESAILSLPKQAAEG |
| 4 (Aazu) | 449424446 | Amycolatopsis azurea DSM 43854 | MPFMPVTDSMFLLVETREHPM HVGGLQLFKKPEDAGPDYLRD LRRKLLDSDNMRDVFRRRPAR PVNTAGHVAWATDNDLELDY HFRHSALPQPGRIRELLELTGR WHSTLLDRHRPLWEIHLVEGL QDGRFAIYSKIHHALMDGVSAL |

TABLE 2-continued

Sequence of wax ester synthases

| SEQ ID NO: | Accession No. (NCBI) | Organism | Sequence |
|---|---|---|---|
| | | | RHLQGTLSDDPTDLDCPPPWGR RPKPDGGRNGKASPSVLSTFGK TVNQLAGIAPAAMKVAREAFQ EHTLTLPAQAPKTMLNVPIGGA RRFAAQSWSLDRVRKVATAAG VSRNDVVLAMCSGALRDYLIE QNSLPDAPLTAMVPVSLRRKDS GDAAGNNIGALLCNLATHLTD PAARLATINASMRNGKKLFSEL TPLQTLLLSGINVAQLGVSPIPG FVNNTKPPFNLVISNVPGPRKQ MYWNGASLDGIYPASVLLDGQ ALNITLTSNGDNLDFGVTGCRR SVPHLQRILTHLDTALAELEHA VSVGRS |
| 5 (Acip) | 479966651 | Acinetobacter sp. CIP 56.2 | MRPLHPIDFIFLSLEKRQQPMH VGGLFLFELPENASPTFVHDLV NEIRQSKSIPVPPFNNQLNGLFW GEDSEFDLDHHFRHIALPNPGRI RELLVYISQQHSSLIDRAKPLW TCDIIEGIEGNRFAMYFKIHHA MVDGVAGMRLIEKSLSQDPNE KHVVPLWCVEGKRTKRLKAPK PPTVSKIKGVMEGIKSQLEVAP KVMQELSQTIFKEMGKNPDYV STFQAPPSILNQRVSSSRRFAAQ SFELGRFRRIAKSLGVTLNDVIL AVCSGALREYLISHNSLPI(KPLI AMVPASLRTDDSDVSNRITMIL ANLATHIEDPIERLEVIRRSVQN SKQRFSRMTANEILNYSAVVYG PAGLNIASGMLPKRQAFNLVIS NVPGPREPLYWNGAKLDALYP ASIVMDGQALNITMTSYLDKLE VGLIACRNALPKMQNLLTHLEE EIQRFEQAIQDLPQKVAN |
| 6 | ABO21021 | Marinobacter hydrocarbono- clasticus ATCC 49840 | MKRLGTLDASWLAVESEDTPM HVGTLQIFSLPEGAPETFLRDM VTRMKEAGDVAPPWGYKLAW SGFLGRVIAPAWKVDKDIDLDY HVRHSALPRPGGERELGILVSR LHSNPLDFSRPLWECHVIEGLE NNRFALYTKMHHSMIDGISGV RLMQRVLTTDPERCNMPPPWT VRPHQRRGAKTDKEASVPAAV SQAMDALKLQADMAPRLWQA GNRLVHSVRHPEDGLTAPFTGP VSVLNHRVTAQRRFATQHYQL DRLKNLAHASGGSLNDIVLYLC GTALRRFLAEQNNLPDTPLTAG IPVNIRPADDEGTGTQISFMIAS LATDEADPLNRLQQIKTSTRRA KEHLQKLPKSALTQYTMLLMS PYILQLMSGLGGRMRPVFNVTI SNVPGPEGTLYYEGARLEAMY PVSLIAHGGALNITCLSYAGSLN FGFTGCRDTLPSMQKLAVYTG EALDELESLILPPKKRARTRK |
| 7 (Maqu T373M, Q420R) | YP_957462 | Marinobacter aquaeolei VT8 T373M, Q420R | MGSSHHHHHHSSGLVPRGSHM TPLNPTDQLFLWLEKRQQPMH VGLQLFSFPEGAPDDYVAQLA DQLRQKTEVTAPFNQRLSYRLG QPVWVEDEHLDLEHHFRFEAL PTPGRIRELLSFVSAEHSHLMDR ERPMWEVHLIEGLKDRQFALY TKVHHSLVDGVSAMRMATRM LSENPDEHGMPPIWDLPCLSRD RGESDGHSLWRSVTHLLGLSG RQLGTIPTVAKELLKTINQARK DPAYDSIFHAPRCMLNQKITGS RRFAAQSWCLKRIRAVCEAYG TTVNDVVTAMCAAALRTYLM |

TABLE 2-continued

Sequence of wax ester synthases

| SEQ ID NO: | Accession No. (NCBI) | Organism | Sequence |
|---|---|---|---|
| | | | NQDALPEKPLVAFVPVSLRRDD SSGGNQVGVILASLHTDVQEAG ERLLKIHHGMEEAKQRYRHMS PEEIVNYTALTLAPAAFHLLTG LAPKWQMFNVVISNVPGPSRPL YWNGAKLEGMYP VSIDMDRLALNMTLTSYNDRV EFGLIGCRRTLPSLQRMLDYLE QGLAELELNAGL |
| 8 (Maqu E72K) | YP_957462 | Marinobacter aquaeolei VT8 E72K (no final H in His-tag) | MGSSHHHHHSSGLVPRGSHMT PLNPTDQLFLWLEKRQQPMHV GGLQLFSFPEGAPDDYVAQLA DQLRQKTEVTAPFNQRLSYRLG QPVWVKDEHLDLEHHFRFEAL PTPGRIRELLSFVSAEHSHLMDR ERPMWEVHLIEGLKDRQFALY TKVHHSLVDGVSAMRMATRM RGESDGHSLWRSVTHLLGLSG RQLGTIPTVAKELLKTINQARK DPAYDSIFHAPRCMLNQKITGS RRFAAQSWCLKRIRAVCEAYG TTVNDVVTAMCAAALRTYLM NQDALPEKPLVAFVPVSLRRDD SSGGNQVGVILASLHTDVQEAG ERLLKIHHGMEEAKQRYRHMS PEEIVNYTALTLAPAAFHLLTG LAPKWQTFNVVISNVPGPSRPL YWNGAKLEGMYPVSIDMDRL ALNMTLTSYNDQVEFGLIGCRR TLPSLQRMLDYLEQGLAELELN AGL |
| 23 (Maqu) | YP_957462 | Marinobacter aquaeolei VT8 | MTPLNPTDQLFLWLEKRQQPM HVGGLQLFSFPEGAPDDYVAQ LADQLRQKTEVTAPFNQRLSYR LGQPVWVEDEHLDLEHHFRFE ALPTPGRIRELLSFVSAEHSHLM DRERPMWEVHLIEGLKDRQFA LYTKVHHSLVDGVSAMRMAT RMLSENPDEHGMPPIWDLPCLS RDRGESDGHSLWRSVTHLLGL SGRQLGTIPTVAKELLKTINQA RKDPAYDSIFHAPRCMLNQKIT GSRRFAAQSWCLKRIRAVCEA YGTTVNDVVTAMCAAALRTYL MNQDALPEKPLVAFVPVSLRR DDSSGGNQVGVILASLHTDVQE AGERLLKIHHGMEEAKQRYRH MSPEEIVNYTALTLAPAAFHLL TGLAPKWQTFNVVISNVPGPSR PLYWNGAKLEGMYPVSIDMDR LALNMTLTSYNDQVEFGLIGCR RTLPSLQRMLDYLEQGLAELEL NAGL |

Throughout this application, any data base code, unless specified to the contrary, refers to a sequence available from the NCBI data bases, more specifically the version online on 12 Jun. 2014, and comprises, if such sequence is a nucleotide sequence, the polypeptide sequence obtained by translating the former.

The cell according to any aspect of the present invention may comprise a third genetic mutation that reduces the fatty acid degradation capacity of the cell relative to the wild type cell.

Degradation of fatty acids is accomplished by a sequence of enzymatically catalyzed reactions. First of all, fatty acids are taken up and translocated across the cell membrane via a transport/acyl-activation mechanism involving at least one outer membrane protein and one inner membrane-associated protein which has fatty acid-CoA ligase activity, referred to in the case of E. coli as FadL and FadD/FadK, respectively. Inside the cell, the fatty acid to be degraded is subjected to enzymes catalyzing other reactions of the β-oxidation pathway. The first intracellular step involves the conversion of acyl-CoA to enoyl-CoA through acyl-CoA dehydrogenase, the latter referred to as FadE in the case of E. coli. The activity of an acyl-CoA dehydrogenase may be assayed as described in the state of art, for example by monitoring the concentration of NADH spectrophotometrically at 340 nm in 100 mM MOPS, pH 7.4, 0.2 mM Enoyl-CoA, 0.4 mM $NAD^+$. The resulting enoyl-CoA is converted to 3-ketoacyl-CoA via 3-hydroxylacyl-CoA through hydration and oxidation, catalyzed by enoyl-CoA hydratase/3-hydroxyacyl-CoA dehydrogenase, referred to as FadB and FadJ in *E. coli*. Enoyl-CoA hydratase/3-hydroxyacyl-CoA dehydrogenase activity, more specifically formation of the product NADH may be assayed spectrophotometrically as described in the state of the art, for example as outlined for FadE. Finally, 3-ketoacyl-CoA thiolase, FadA and FadI in *E. coli*, catalyzes the cleavage of 3-ketoacyl-CoA, to give acetyl-CoA and the input acyl-CoA shortened by two carbon atoms. The activity of ketoacyl-CoA thiolase may be assayed as described in the state of the art, for example in Antonenkov, V., D. et al. (1997) Substrate specificities of 3-oxoacyl-CoA thiolase and sterol carrier protein 2/3-oxoacyl-coa thiolase purified from normal rat liver peroxisomes. Sterol carrier protein 2/3-oxoacyl-CoA thiolase is involved in the metabolism of 2-methyl-branched fatty acids and bile acid intermediates. In one example, the term "a cell having a reduced fatty acid degradation capacity", as used herein, refers to a cell having a reduced capability of taking up and/or degrading fatty acids. The fatty acid degradation capacity of a cell may be reduced in various ways. In another example, the cell has, compared to its wild type, a reduced activity of an enzyme involved in the β-oxidation pathway. In a further example, the term "enzyme involved in the β-oxidation pathway", as used herein, refers to an enzyme that interacts directly with a fatty acid or a derivative thereof formed as part of the degradation of said fatty acid via the β-oxidation pathway the sequence of reactions effecting the conversion of a fatty acid to acetyl-CoA and the CoA ester of the shortened fatty acid, for example by recognizing the fatty acid or derivative thereof as a substrate, and converts it to a metabolite formed as a part of the β-oxidation pathway. More in particular, the reduced fatty acid degradation capacity in the cell according to any aspect of the present invention may be the third genetic mutation which results in a decrease in the expression of at least one enzyme selected from the group consisting of acyl-CoA dehydrogenase, 2,4-dienoyl-CoA reductase, enoyl-CoA hydratase and 3-ketoacyl-CoA thiolase relative to the wild type cell.

For example, the acyl-CoA dehydrogenase is an enzyme involved in the β-oxidation pathway as it interacts with fatty acid-CoA and converts fatty acid-CoA ester to enoyl-CoA, which is a metabolite formed as part of the β-oxidation. In a further example, the term "enzyme involved in the β-oxidation pathway", as used herein, comprises any polypeptide from the group comprising acyl-CoA dehydrogenase, enoyl-CoA hydratase, 3-hydroxyacyl-CoA dehydrogenase and 3-keto-acyl-CoA thiolase. Subsequently, the acyl-CoA synthetase may catalyze the conversion a fatty acid to the CoA ester of a fatty acid, i.e. a molecule, wherein the functional group —OH of the carboxy group is replaced with —S—CoA, for introducing said fatty acid into the β-oxidation pathway. For example, the polypeptides FadD and FadK in *E. coli* (access code: BAA15609.1) are acyl-CoA dehydrogenases. In an example, the term "acyl-CoA dehydrogenase", as used herein, is a polypeptide capable of catalyzing the conversion of an acyl-CoA to enoyl-CoA, as part of the β-oxidation pathway. For example, the polypeptide FadE in *E. coli* (access code: BAA77891.2) is an acyl-CoA dehydrogenase. In one example, the term "2,4-dienoyl-CoA reductase", as used herein, is a polypeptide capable of catalyzing the conversion of the 2,4-dienoyl CoA from an unsaturated fatty acid into enoyl-CoA, as part of the β-oxidation pathway. For example, the polypeptide FadH in *E. coli* is a 2,4-dienoyl-CoA reductase. In an example, the term "enoyl-CoA hydratase", as used herein, also referred to as 3-hydroxyacyl-CoA dehydrogenase, refers to a polypeptide capable of catalyzing the conversion of enoyl-CoA to 3-ketoacyl-CoA through hydration and oxidation, as part of the β-oxidation pathway. For example, the polypeptides FadB and FadJ in *E. coli* (access code: BAE77457.1) are enoyl-CoA hydratases. In one example, the term "ketoacyl-CoA thiolase", as used herein, refers to a polypeptide capable of catalyzing the conversion of cleaving 3-ketoacyl-CoA, resulting in an acyl-CoA shortened by two carbon atoms and acetyl-CoA, for example as the final step of the β-oxidation pathway. For example, the polypeptides FadA and FadI in *E. coli* (access code: AP009048.1) are ketoacyl-CoA thiolases.

In particular, the cell according to any aspect of the present invention may comprise genetic mutations that result in an increase in the expression of β-ketoacyl-ACP synthase III. This may be the first mutation in the cell according to any aspect of the present invention. Any β-ketoacyl-ACP synthase III (fabH) known in the art may be used in the method according to any aspect of the present invention. In particular, the fabH may be selected from Table 3a.

TABLE 3a

Possible sources of FabH that may be used to produce fatty acids such as lauric acid.

| FabH | Accession No. |
| --- | --- |
| *Shewanella* sp. MR-4 | gi\|113969844 |
| *Shewanella frigidimarina* NCIMB 400 | gi\|114563637 |
| *Shewanella* sp. ANA-3 | gi\|117920011 |
| *Shewanella amazonensis* SB2B | gi\|119774647 |
| *Shewanella* sp. W3-18-1 | gi\|120598458 |
| *Shewanella baltica* OS185 | gi\|153001200 |
| *Gordonia bronchialis* DSM 43247 | gi\|262201496 |
| *Gordonia neofelifaecis* NRRL B-59395 | gi\|326383808 |
| putative *Shewanella* sp. HN-41 | gi\|336312046 |
| *Rheinheimera* sp. A13L | gi\|336314652 |
| *Gordonia araii* NBRC 100433 | gi\|359421305 |
| *Gordonia polyisoprenivorans* NBRC 16320 | gi\|359767552 |
| *Gordonia effusa* NBRC 100432 | gi\|359774344 |
| *Alishewanella jeotgali* KCTC 22429 | gi\|375108677 |
| *Gordonia otitidis* NBRC 100426 | gi\|377561073 |
| *Gordonia sputi* NBRC 100414 | gi\|377565709 |
| *Gordonia terrae* NBRC 100016 | gi\|377571475 |
| *Gordonia polyisoprenivorans* VH2 | gi\|378716896 |
| *Alishewanella agri* BL06 | gi\|393761603 |
| *Gordonia* sp. KTR9 | gi\|404214055 |
| *Shewanella oneidensis* MR-1 | gi\|414562081 |
| *Gordonia hirsuta* DSM 44140 | gi\|441517717 |
| *Gordonia sihwensis* NBRC 108236 | gi\|441522685 |
| *Gordonia soli* NBRC 108243 | gi\|444431726 |
| *Gordonia malaquae* | gi\|495656093 |
| *Gordonia* sp. NB4-1Y | gi\|464805365 |
| *Thalassolituus oleivorans* MIL-1 | gi\|473830078 |
| *Colwellia psychrerythraea* 34H | gi\|71278947 |
| *Shewanella denitrificans* OS217 | gi\|91793871 |
| *Rheinheimera nanhaiensis* E407-8 | gi383934006 |
| *Acinetobacter* sp. CIP 53.82 | 480152603 |
| *Hahella chejuensis* KCTC 2396 | 83645428 |
| *Acinetobacter* sp. SH024 | 293608659 |
| *Acinetobacter* sp. NBRC 10098 | 359430113 |
| *Acinetobacter* sp. ADP1 | 50085221 |
| *Acinetobacter ursingii* DSM 16037 = CIP 107286 | 406040759 |
| *Acinetobacter bohemicus* ANC 3994 | 479867614 |
| *Candidatus Accumulibacter phosphatis* clade IIA str. UW-1 | 257092603 |
| blood disease bacterium R229 | 344167953 |

TABLE 3a-continued

Possible sources of FabH that may be used to produce fatty acids such as lauric acid.

| FabH | Accession No. |
|---|---|
| *Ralstonia solanacearum* CMR15 | 410684104 |
| *Marinobacter* sp. BSs20148 | 399545195 |
| *Marinobacter algicola* DG893 | 149375225 |
| *Ralstonia* sp. 5_7_47FAA | 309779507 |
| *Rubrivivax gelatinosus* IL144 | 383757692 |
| *Oceanobacter* sp. RED65 | 94501061 |
| gamma proteobacterium HTCC5015 | 254447852 |
| *Ilumatobacter coccineus* YM16-304 | 470180366 |
| marine gamma proteobacterium HTCC2148 | 254480565 |
| *Marinobacter aquaeolei* VT8 | 120554511 |
| *Alcanivorax* sp. DG881 | 254427265 |
| *Hydrocarboniphaga effusa* AP103 | 392950783 |
| *Curvibacter* putative symbiont of *Hydra magnipapillata* | 260220470 |
| gamma proteobacterium HdN1 | 304312991 |
| marine gamma proteobacterium HTCC2080 | 119503170 |
| gamma proteobacterium IMCC3088 | 329897271 |
| gamma proteobacterium NOR5-3 | 254514195 |
| *Acinetobacter radioresistens* SK82 | 255318218 |
| *Acinetobacter* sp. NIPH 899 | 479953276 |
| *Acinetobacter schindleri* CIP 107287 | 480002578 |
| *Acinetobacter towneri* DSM 14962 = CIP 107472 | 480029713 |
| *Acinetobacter junii* CIP 107470 | 480007780 |
| *Acinetobacter* sp. CIP 56.2 | 479964140 |
| *Acinetobacter baumannii* AYE *baumannii* MDR-ZJ06 | 169796586 |
| *Acinetobacter gerneri* DSM 14967 = CIP 107464 | 479991204 |
| *Acinetobacter bouvetii* DSM 14964 = CIP 107468 | 480043238 |
| *Acinetobacter* sp. ANC 3789 | 479932652 |
| *Acinetobacter lwoffii* SH145 | 262375396 |
| *Acinetobacter soli* NIPH 2899 | 480019083 |
| *Acinetobacter baumannii* WC-323 | 425744072 |
| *Acinetobacter calcoaceticus* NIPH 13 | 479856262 |
| *Acinetobacter johnsonii* SH046 | 262369694 |
| *Acinetobacter haemolyticus* CIP 64.3 | 480080132 |
| *Acinetobacter* sp. CIP 102529 | 479942708 |
| *Acinetobacter* sp. CIP-A165 | 479879420 |
| *Acinetobacter guillouiae* CIP 63.46 | 479909393 |
| *Ralstonia solanacearum* FQY_4 | 469776065 |
| Ralstonia *solanacearum* UW551 | 83747353 |

The β-ketoacyl-ACP synthase III (FabH) may comprise sequence identity of at least 50% to a polypeptide selected from the group consisting of SEQ ID NOs: 24-27 and combinations thereof or to a functional fragment of any of the polypeptides. In particular, the FabH may comprise sequence identity of at least 50% to a polypeptide of SEQ ID NOs: 24-27 and combinations thereof. More in particular, the FabH used according to any aspect of the present invention may comprise sequence identity of at least 60, 65, 70, 75, 80, 85, 90, 95, 98 or 100% to a polypeptide of any one of sequences of SEQ ID NOs: 24-27 and combinations thereof. More in particular, the cell according to any aspect of the present invention may have a first mutation that comprises a combination of sequences of FabH. For example, the cell according to any aspect of the present invention may be genetically modified to comprise a polypeptide with sequence identity of at least 50, 60, 65, 70, 75, 80, 85, 90, 95, 98 or 100% to a polypeptide of comprising SEQ ID NOs: 24 and 27, SEQ ID NOs: 25 and 27, SEQ ID NOs: 26 and 27 and the like.

These sequences are only reference amino acid sequences. In particular, the sequence of the FabH used according to any aspect of the present invention may comprise amino acids other than those essential for the function, for example the catalytic activity of a protein, or the fold or structure of a molecule are deleted, substituted or replaced by insertions or essential amino acids are replaced in a conservative manner to the effect that the biological activity of the reference sequence or a molecule derived therefrom is preserved.

TABLE 3b

Sequences of FabH, crt, Hbd that may be used in the cells according to any aspect of the present invention

| SEQ ID NO: | Accession No. (NCBI)/ | Organism | Sequence |
|---|---|---|---|
| 24 | WP_014577218.1 | *Marinobacter adhaerens* HP15 | MIKAVISGTGLYTPPATISNDE LVEAFNQYVELFNAENADAI ASGDVTPLQPSSSSFIEKASGI KRRHVIDKDGILDPNRMKPYI PDRSNEEPSVQCDMAVTACR EALEQAGKSAEDVDAVIVAC SNLQRAYPAVSIEVQEALGID GFAYDMNVACSSATFGLQAA VNSVENGSARAVLVVSPEICS GHLNFRDRDSHFIFGDACTAI LVEREEDTREGQGFEILGTSL KTKFSNNIRNNFGFLNRADES GVGKPDKLFVQQGRKVFKEV SPLVAETIQKQLQSLSLAPDD LRRMWLHQANLNMNQLIAR KVLGRDATEEEAPVILDEYAN TSSAGSIIAFHKNKDDLVSGD LGVICSFGAGYSIGSVVVRRR |
| 25 | ZP_10350240 | *Alishewanella agri* BL06 | MQQVVISGSGLFTPQHRISNE ELVQSYNQYVDQFNEEHAAA IAAGEIEALEYSSTEFIEKASGI KARHVLYKDGILDPKIMHPVF |

TABLE 3b-continued

Sequences of FabH, crt, Hbd that may be used in the cells according to any aspect of the present invention

| SEQ ID NO: | Accession No. (NCBI)/ | Organism | Sequence |
|---|---|---|---|
|  |  |  | RKRGEDELPEMVEMAVQAA TQALAQANKTAADIDLIICAA SNMQRPYPALSVELQQALGA GGYAFDMNVACSSATFAISN AVNAIRGGTAKVVLVVNPEF ASPQVDYRSRDSHFIFGDVCT ATIIEAESSCSSQQAFRILGMR LKTTFSNNIRCDIGYTEHCFTE QDPKAPFFKQQGRKVFKELLP IVADVIQDEMAAQNLAPDDL KRLWLHQANINMNIFAAKKI LGRDPLPEEAPLVLDTYANTA SAGSIIAFHKYQQGLVSGDKA ILCSFGAGYSVGCVVLEKC |
| 26 | ENU26638 | *Acinetobacter* sp. NIPH 236 | MGIRITGTGLFHPTESISNEEL VESLNAYVEQFNQENAEQIA AGEIEALRGSSPEFIEKASGIQ RRYVVEKSGILDPKRLRPRLQ ERSNDELSLQAEWGVIAAKQ AMENAGVTAEDIDVVILACS NMQRAYPAVAIEIQSALGIQG YAYDMNVACSAATFGLKQA YDAVKCGARRVLLLNVEITS GHLDYRTRDAHFIFGDVATA SIIEETETKSGYEILDIHLFTQF SNNIRNNFGFLNRSEDAVVDD KLFRQDGRKVFKEVCPLVAKI ITAQLEKLELTPEQVKRFWLH QANANMNELILKLVVGKEAD LERAPIILDEFANTSSAGVIIA MHRTGEQVNNGEYAVISSFG AGYSVGSIIVQKHIA |
| 27 | YP_006031367 | *Ralstonia solanacearum* Po82 | MHDVVISGTGLWVAPEVITN EELVASFNAYARHYNEANAT AIAAGTLAAVAESSVEFIEKA SGIRQRYVIDKAGVLDPARM RPRLAPRGDDALSLQAEIGVA AAREALAAAGRDAGDIDMLI CSAANMQRPYPAMGIEIQNA LGADGYAFDMNVACSSATFG LEQAINAVRTGSARVALMVN PEITSGHLAWKDRDCHFIFGD VCTAVVVERADDARAPDQW QVLGTRMATRFSNSIRNNAGF LSRSEDRDPDDRDQLFRQEGR KVFKEVCPMAAEHIAGHLQS LGHAPADVRRFWLHQANLG MNQLIGKRLLGRDASADEAP VILDEFANTASAGSIIAFHRHR ADLQPGDLGLICSFGAGYSIG SVAVRKR |
| 28 | AAA95967 | *Clostridium acetobutylicum* ATCC 824 | MELNNVILEKEGKVAVVTIN RPKALNALNSDTLKEMDYVI GEIENDSEVLAVILTGAGEKS FVAGADISEMKEMNTIEGRKF GILGNKVFRRLELLEKPVIAA VNGFALGGGCEIAMSCDIRIA SSNARFGQPEVGLGITPGFGG TQRLSRLVGMGMAKQLIFTA QNIKADEALRIGLVNKVVEPS ELMNTAKEIANKIVSNAPVAV KLSKQAINRGMQCDIDTALAF ESEAFGECFSTEDQKDAMTAF IEKRKIEGFKNR |
| 29 | NP_349314 | *Clostridium acetobutylicum* ATCC 824 | MKKVCVIGAGTMGSGIAQAF AAKGFEVVLRDIKDEFVDRG LDFINKNLSKLVKKGKIEEAT KVEILTRISGTVDLNMAADCD LVIEAAVERMDIKKQIFADLD NICKPETILASNTSSLSITEVAS |

TABLE 3b-continued

Sequences of FabH, crt, Hbd that may be used in the cells according to any aspect of the present invention

| SEQ ID NO: | Accession No. (NCBI)/ | Organism | Sequence |
|---|---|---|---|
| | | | ATKRPDKVIGMHFFNPAPVM KLVEVIRGIATSQETFDAVKE TSIAIGKDPVEVAEAPGFVVN RILIPMINEAVGILAEGIASVE DIDKAMKLGANHPMGPLELG DFIGLDICLAIMDVLYSETGDS KYRPHTLLKKYVRAGWLGR KSGKGFYDYSK |

As used herein, the term "fatty ester" means an ester. In particular, a fatty ester is any ester made from a fatty acid to produce a fatty acid ester. In one example, a fatty ester contains an A side (i.e., the carbon chain attached to the carboxylate oxygen) and a B side (i.e., the carbon chain comprising the parent carboxylate). In a particular, when the fatty ester is derived from the fatty acid biosynthetic pathway, the A side is contributed by an alcohol, and the B side is contributed by a fatty acid. Any alcohol can be used to form the A side of the fatty esters. For example, the alcohol can be derived from the fatty acid biosynthetic pathway. Alternatively, the alcohol can be produced through non-fatty acid biosynthetic pathways. In one example, the alcohol can be provided exogenously. For example, the alcohol can be supplied in the fermentation broth in instances where the fatty ester is produced by an organism that can also produce the fatty acid. Alternatively, a carboxylic acid, such as a fatty acid or acetic acid, can be supplied exogenously in instances where the fatty ester is produced by an organism that can also produce alcohol.

The carbon chains comprising the A side or B side can be of any length. In one example, the A side of the ester is at least about 1, 2, 3, 4, 5, 6, 7, 8, 10, 12, 14, 16, or 18 carbons in length. The B side of the ester is at least about 4, 6, 8, 10, 12, 14, 16, 18, 20, 22, 24, or 26 carbons in length. The A side and/or the B side can be straight or branched chain. The branched chains may have one or more points of branching. The branched chains may also include cyclic branches and/or the A side and/or B side can be saturated or unsaturated. If unsaturated, the A side and/or B side can have one or more points of unsaturation.

In one example, the fatty ester according to any aspect of the present invention may be produced biosynthetically. In particular, the fatty acid may be "activated" to produce at least one compound selected from the group consisting of acyl Coenzyme A (acyl-CoA), and acyl phosphate. More in particular, the fatty ester may be activated to Acyl-CoA, a direct product of fatty acid biosynthesis or degradation. Acyl-CoA may also be synthesized from a free fatty acid, a CoA, or an adenosine nucleotide triphosphate (ATP). An example of an enzyme which produces acyl-CoA is acyl-CoA synthase. Acyl-CoA may then be transferred to a recipient nucleophile such as alcohols, thiols, phosphates and the like.

The cell according to any aspect of the present invention may be further genetically modified to increase the expression of 3-hydroxyacyl coenzyme A dehydratase (3HCDh) and/or keto acyl-CoA reductase (KCR) relative to the wild type cell. This is increase in expression may improve the activity of fadB. In particular, the 3HCDh may crotonase/enoyl-CoA hydratase (Crt) and/or the KCR may be hydroxy-butyric dehydrogenase (Hbd). More in particular, the Crt may have sequence identity of at least 50, 60, 65, 70, 75, 80, 85, 90, 95, 98 or 100% identity to a polypeptide of SEQ ID NO:28 and/or the Hbd has sequence identity of at least 50, 60, 65, 70, 75, 80, 85, 90, 95, 98 or 100% identity to a polypeptide of SEQ ID NO:29.

In particular, the fatty acid ester may be produced in the presence of at least one exogenous alcohol selected from the group consisting of methanol, ethanol, propanol, butanol, pentanol, hexanol, heptanol, octanol, decanol, dodecanol, tetradecanol, hexadecanol and the like.

More in particular, the fatty acid may be 12 carbons in length. The fatty acid may be lauric acid, the acyl coenzyme A thereof may be lauroyl coenzyme A and the fatty acid ester may be methyl laurate. According to another aspect of the present invention there is provided a method for producing methyl laurate, the method comprising contacting lauric acid and/or lauroyl coenzyme A with an isolated wax ester synthase that has sequence identity of at least 50% to a polypeptide of SEQ ID NOs: 1-8 and combinations thereof. More in particular, the wax ester synthase used according to any aspect of the present invention may comprise sequence identity of at least 60, 65, 70, 75, 80, 85, 90, 95, 98 or 100% to a polypeptide of any one of sequences of SEQ ID NOs: 1-8 and combinations thereof. These sequences are only reference amino acid sequences. In particular, the sequence of the wax ester synthase used according to any aspect of the present invention may comprise amino acids other than those essential for the function, for example the catalytic activity of a protein, or the fold or structure of a molecule are deleted, substituted or replaced by insertions or essential amino acids are replaced in a conservative manner to the effect that the biological activity of the reference sequence or a molecule derived therefrom is preserved.

In particular, the method according to any aspect of the present invention is carried out within the cell according to any aspect of the present invention.

Having generally described this invention, a further understanding can be obtained by reference to certain specific examples which are provided herein for purposes of illustration only, and are not intended to be limiting unless otherwise specified.

The foregoing describes preferred embodiments, which, as will be understood by those skilled in the art, may be subject to variations or modifications in design, construction or operation without departing from the scope of the claims. These variations, for instance, are intended to be covered by the scope of the claims.

EXAMPLES

Example 1

Optimization of C12 Fatty Acyl-CoA Production in *E. coli* Production of Fatty Acids Via Malonyl-CoA and Acetyl-CoA in a Shake Flask Experiment TABLE 4a List of microorganism strains that were used to produce fatty acids in the subsequent examples. The method of production and the sequences of the strains are provided in Table 3.2 of WO2014026162A1 (OPX Biotechnologies Inc., USA).

| Strain designation | Host | Plasmid | SEQ ID NOs. |
|---|---|---|---|
| BXF_0012 | BX_864 | 1)pBMT-3_ccdAB | 30 |
| BXF_0013 | BX_864 | 1)pBMT-3_ccdAB_$P_{T7}$-'tesA | 31 |
| BXF_0014 | BX_864 | 1)pBMT-3_ccdAB_$P_{T7}$-nphT7-hbd-crt-ter | 32 |
| BXF_0015 | BX_864 | 1)pBMT-3_ccdAB_$P_{T7}$-'tesA_PT7-nph$_{T7}$-hbd-crt-ter | 33 |
| BXF_0018 | BX_864 | pBMT-3_ccdAB_PT7-nphT7-hbd-crt-ter | 32 |
| BXF_0020 | BX_860 | 1)pBMT-3_ccdAB_PT7-'tesA_PT7-nphT7-hbd-crt-ter | 33 |
| BXF_0021 | BX_876 | 1)pBMT-3_ccdAB_PT7-'tesA_PT7-nphT7-hbd-crt-ter | 33 |
| BXF_0022 | BX_874 | 1)pBMT-3_ccdAB | 30 |
| BXF_0023 | BX_874 | 1)pBMT-3_ccdAB_PT7-'tesA | 31 |
| BXF_0024 | BX_874 | 1)pBMT-3_ccdAB_PT7-'tesA_PT7-nphT7-hbd-crt-ter | 33 |
| BXF_0025 | BX_875 | 1)pBMT-3_ccdAB | 30 |
| BXF_0026 | BX_875 | 1)pBMT-3_ccdAB_PT7-'tesA | 31 |
| BXF_0027 | BX_875 | 1)pBMT-3_ccdAB_PT7-'tesA_PT7-nphT7-hbd-crt-ter | 33 |
| BXF_0028 | BX_878 | 1)pBMT-3ccdAB-T7-'tesA-PT7_nphT7_hbd_crt_ter | 33 |
| BXF_0028 | BX_878 | 1)pBMT-3_ccdAB_PT7-'tesA_PT7-nphT7-hbd-crt-ter | 33 |
| BXF_0029 | BX_879 | 1)pBMT-3_ccdAB_PT7-'tesA_PT7-nphT7-hbd-crt-ter | 33 |
| BXF_0030 | BX_881 | 1)pBMT-3_ccdAB_PT7-'tesA_PT7-nphT7-hbd-crt-ter | 33 |
| BXF_0031 | BX_864 | 1)pBMT-3_ccdAB_PT7-'tesA_PT7-nphT7-hbd-crt-ter 2)pET-28b(empty vector) | 33 |
| BXF_0033 | BX_878 | 1)pBMT-3_ccdAB_PT7-nphT7-hbd-crt-ter | 32 |
| BXF_0034 | BX_879 | 2)BMT-3_ccdAB_PT7-nphT7-hbd-crt-ter | 32 |

A base strain was constructed by chromosomal integration of Hbd and Crt into the BX_1018 parent strain. The following set of strains were transformed and evaluated in small scale for both FAME production and metabolite accumulation.

TABLE 4b list of strains used for testing hbd and crt presence in FAME production

| Strain | Parent(s) | Plasmid 1 | Plasmid 2 |
|---|---|---|---|
| BXE_062 | BX_1018 | pET-PpstsIH-Aagr | pACYC-PpstsIH-nphT7(SV)-ter-PpstsIH-fadB-Maqu |
| BXE_207 | BX_1018 | pET-PpstsIH-Aagr | pACYC-PpstsIH-nphT7(SV)-ter-PpstsIH-fadB-Ppho-Maqu |
| BXE_229 | BX_1018 ΔyibD:PyibD-hbd-crt | pET-PpstsIH-Aagr | pACYC-PpstsIH-nphT7(SV)-ter-PpstsIH-fadB-PphoE-Maqu |
| BXE_230 | BX_1018 ΔyibD:PyibD-hbd-crt | pET-PpstsIH-Aagr | pACYC-PpstsIH-nphT7(SV)-ter-PpstsIH-fadB-Maqu |

Figure 12:
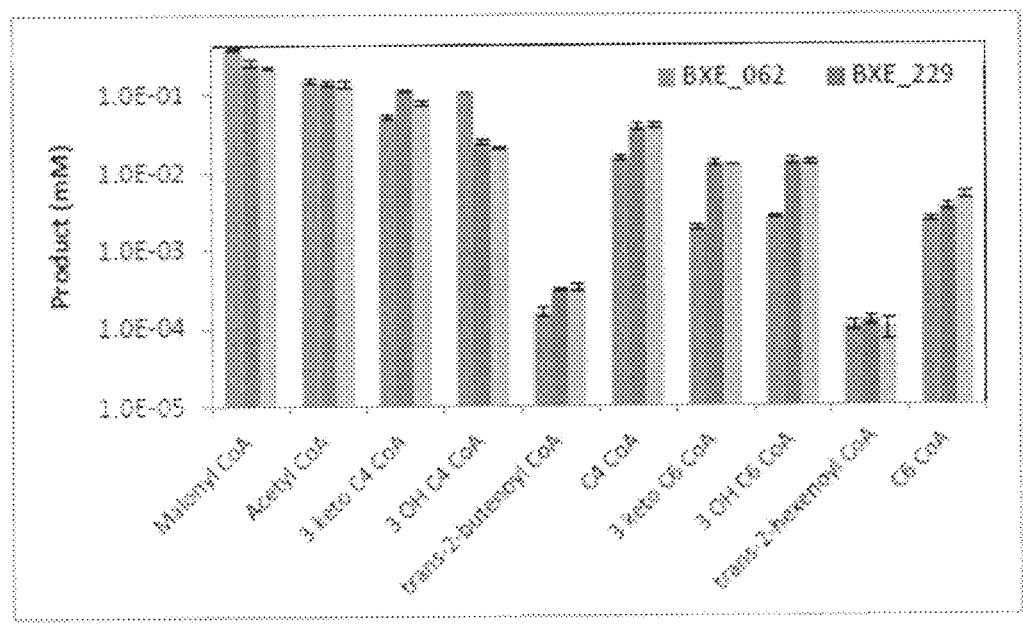
FIG. 12 is a graph showing the evaluation of intermediate product accumulation specific to the C4→C6 elongation steps of the lauroyl-CoA production pathway (data collected but not shown for the C6→C12 intermediates.)

To better understand the impact of Hbd/Crt expression, metabolite accumulation was monitored in cell lysate following incubation with malonyl-CoA and acetyl-CoA substrates. The results of this assay, as presented in FIG. 12, showed increased accumulation of C4-C6-CoA intermediates consistent with the expected activity on keto- and hydroxy-C4-CoAs.

Engineering β-Keto Acyl-CoA Synthases (FabH)

A screening approach was employed for β-keto acyl-CoA synthase homologs to identify candidates for lauric acid production based on demonstrated activity on C4- to C10 acyl-CoA substrates. Greater than 70 homologs have been synthesized, expressed, purified and evaluated for activity in vitro.

Synthase candidates identified to have significant activity on C4- to C10-CoA substrates were incorporated into production hosts and evaluated for FFA production in shake flask. FIG. 1 shows FFA production profiles at 68 hours for several of the engineered strains (Table 4c) exhibiting significant lauric acid production. As shown, both lauric acid and total FFA production profiles are modulated by the individual synthase candidate(s) incorporated. For example, strain BXF_198, which contains the Aagr fabH construct, shows the highest specificity for lauric acid, whereas co-expression of Rsol fabH corresponds to the highest titer in total FFA. All four synthase combinations shown in FIG. 1 have been selected for Example 3 focused on production of methyl laurate.

TABLE 4c

Bacterial strains with specific plasmids used in the screening phase

| Strain | Host | Plasmid 1 | Plasmid 2 |
|---|---|---|---|
| BXF_166 | BX_978 | 1009_pACYC-PpstsIH-nphT7(1147S, F217V)-ter-TT_PpstsIH-fadB | 1007_pET28b-ΔlacI-PpstsIH-Madh fabH-Aagr fabH |
| BXF_169 | BX_985 | 1009_pACYC-PpstsIH-nphT7(1147S, F217V)-ter-TT_PpstsIH-fadB | 1008_pET28b-ΔlacI-PpstsIH-Anip fabH-Aagr fabH |
| BXF_185 | BX_985 | 1009_pACYC-PpstsIH-nphT7(1147S, F217V)-ter-TT_PpstsIH-fadB | 1045_pET28b-ΔlacI-PpstsIH-Rsol fabH-Aagr fabH |
| BXF_198 | BX_985 | 1009_pACYC-PpstsIH-nphT7(1147S, F217V)-ter-TT_PpstsIH-fadB | 1123_pET28b-ΔlacI-PpstsIH-Aagr fabH |

Baseline FFA Analysis

Figure 2:
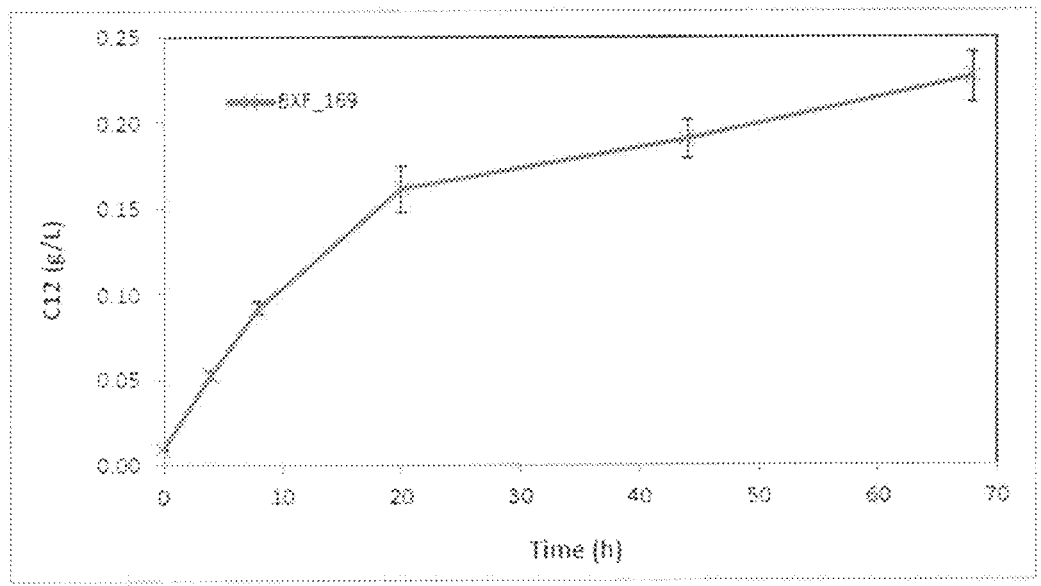
FIG. 2 is a graph showing the lauric acid production profile for BXF_169 evaluated in 50 ml shake flask, $OD_{600}=2$.

A more comprehensive baseline analysis was completed with a subset of FFA production strains with various synthase combinations as described above. Data for strain BXF_169 is presented; similar trends were observed among all strains that were evaluated in the more comprehensive tests. The data presented in FIG. 2 shows a time course of lauric acid production for strain BXF_169. In the shake flask test conditions, the strain exhibited a stable initial production rate for 10-20 hours. After the 20 hours, the rate decreased significantly and product titer levels off.

Figure 3:
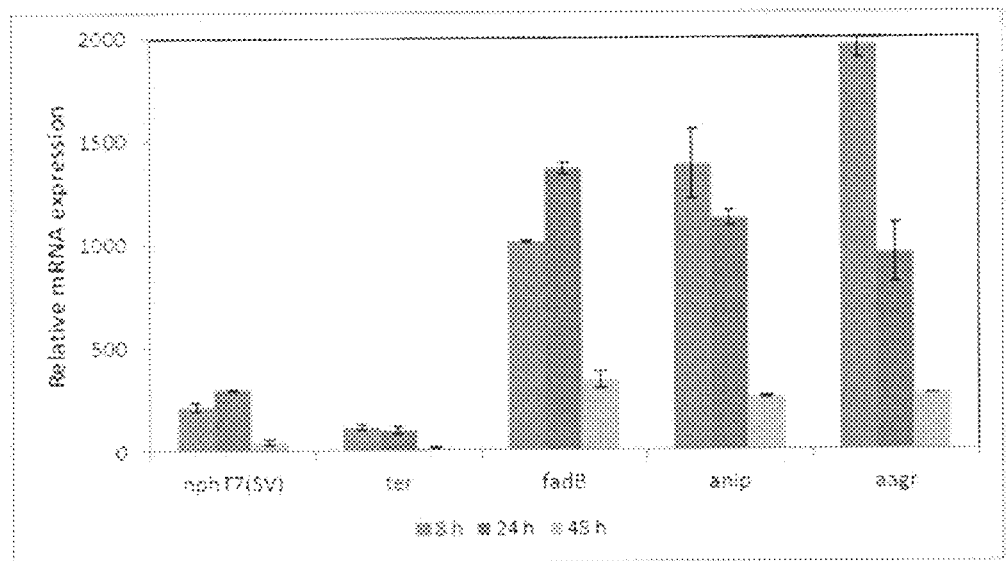
FIG. 3 is a graph showing the mRNA expression relative to cysG for various pathway genes in BXF_169 measured at 8, 24 and 48 hrs.
Figure 4:
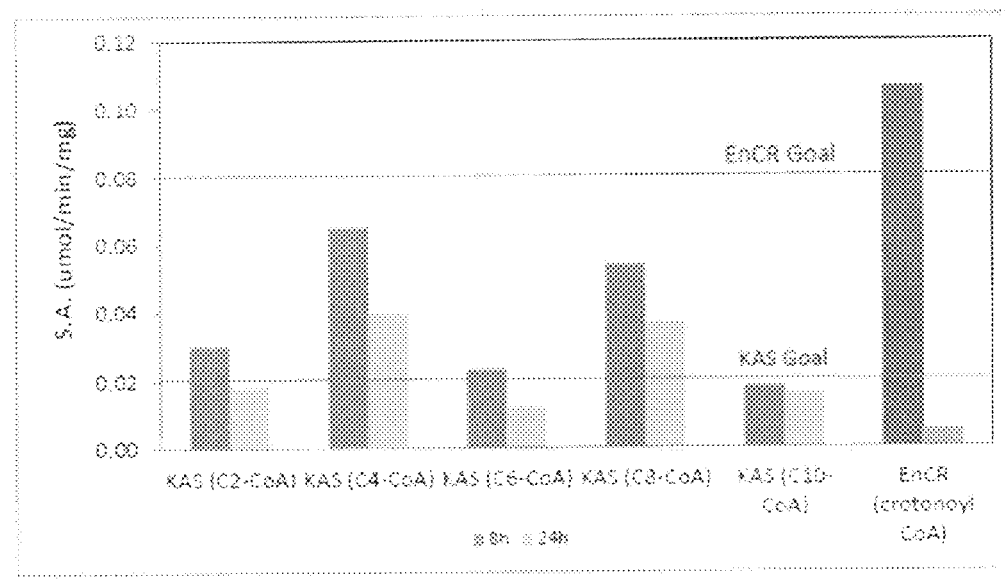
FIG. 4 is a graph showing the enzyme activity for various elongation steps measured in lysate for BXF_169 at 8 and 24 hours. EnCR activity is encoded by the Ter gene. KAS activities are encoded by the NphT7 and FabH genes.

For all strains analyzed, samples were taken at each time point and analyzed for transcript, expression, and activity for key enzymes in the fatty acid production pathway. FIGS. 3 and 4 show the relative mRNA expression of the pathway genes and the corresponding enzyme activity over time for BXF_169. Transcription levels were good, but also differed between the five genes despite being driven from the same promoter. Both transcript and enzyme activity showed a decreasing trend over time, with enzyme activities dropping for several reactions at the 24 hour time point. Similar trends were observed for all other FFA production strains evaluated.

In addition to reduced mRNA and enzyme activity, the 24-hour time point was also characterized by increased insoluble protein accumulation and decreased glucose consumption for all strains (data not shown). As fatty acids including lauric acid are known to accumulate inside the cells in the absence of specific transporters, it was hypothesized that the reduction in productivity at 24 hours is due to intracellular FFA toxicity.

In Vitro Analysis of the Fatty Acid Synthesis Pathway

An assay was developed by reconstructing the fatty acyl-CoA pathway in vitro with purified enzymes. The in vitro reconstruction simplified identification of rate-limiting steps, which were characterized by metabolite accumulation under reaction conditions. There were several benefits of in vitro pathway reconstitution including isolation of pathway flux from competitive enzymes (e.g. thioesterases), substrate limitations (e.g. NADH pools), and balanced expression of multiple pathway enzymes. The equilibrium of the pathway was evaluated by quantifying all 20 pathway intermediates from malonyl-CoA to lauroyl-CoA in the presence of varying amounts of enzymes or substrates (acyl-CoA intermediates).

Figure 5:
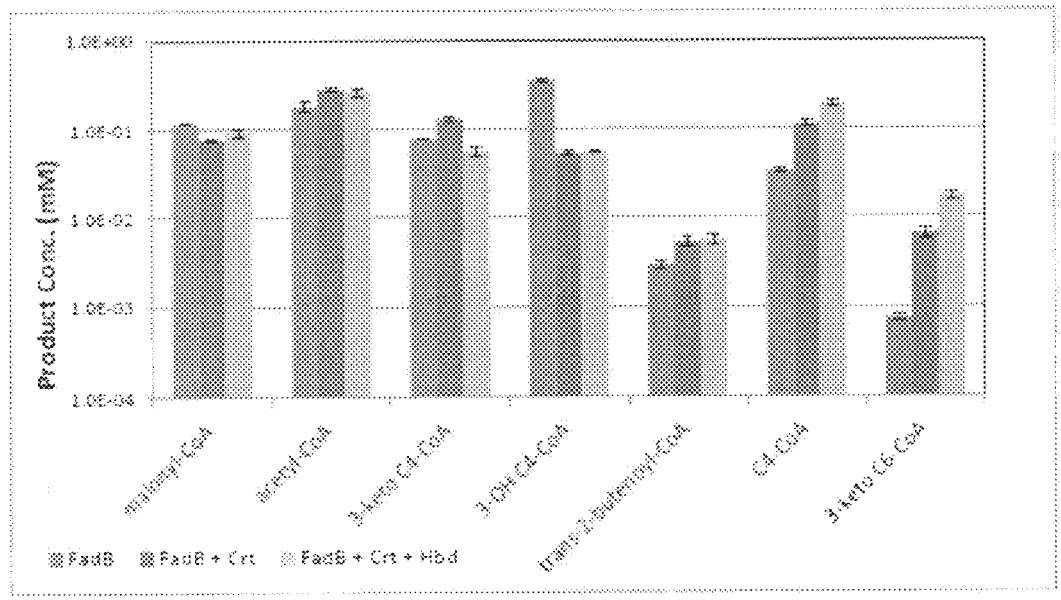
FIG. 5 is a graph showing intermediate product formation and utilization specific to the C4→C6 elongation steps of the lauroyl-CoA production pathway (data collected but not shown for the C6→C12 intermediates) from in vitro pathway reconstitution with FadB, FadB+Crt and FadB+Crt+Hbd.

FIG. 5 shows the accumulation of pathway intermediates for the C4 to C6 elongation cycle observed while varying the enzymes for the keto acyl-CoA reductase (KCR) and 3-hydroxyacyl-CoA dehydratase (3HCDh) reactions. As shown, when the pathway was reconstructed with FadB, there was significant accumulation of 3-hydroxybutyryl-CoA, suggesting insufficient 3HCDh activity to drive the reaction forward. The observed accumulation may be due to the preference for this enzyme to catalyze the reverse reaction, which may also be reducing overall forward pathway flux in vivo. However, when FadB is supplemented with Hbd and/or Crt (alternative KCR and 3HCDh enzymes that have significant activity in the forward direction with C4 intermediates), a reduction in 3-hydroxybutyryl-CoA accumulation was observed. These data suggested that the supplemental activity was sufficient to drive the pathway forward to butyryl-CoA and that integration of Hbd and Crt into production hosts may enhance production of longer chain fatty acids.

Synthase Mutant Evaluations

Figure 13:
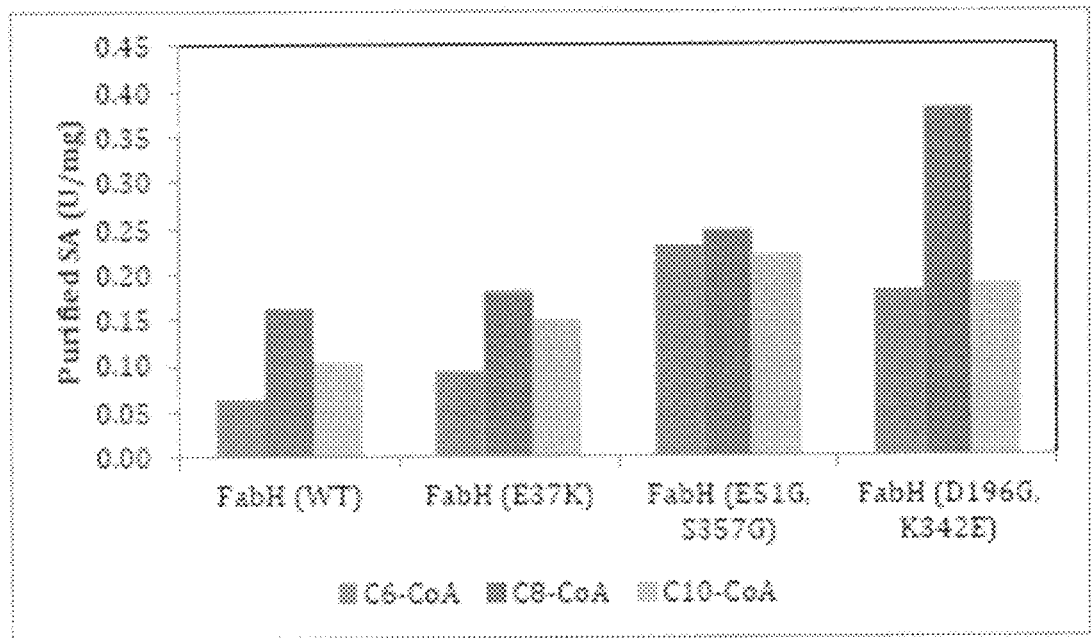
FIG. 13 is a graph showing specific enzyme activities for three FabH mutant enzymes with C6-C10-CoA substrates compared to wild-type FabH.

FabH variants were isolated from a 96-well plate-based screen developed to detect beneficial mutations with improved activity on C10-CoA. Following the initial screen of >1000 mutants, positive variants were sequenced and activity on C6-C10-CoA was evaluated. As shown in FIG. 13, three of the purified variants identified were confirmed to have increased activity on C6-C10-CoA substrates.

Following positive confirmation, FabH mutants were evaluated in vivo. The following strains were constructed by incorporating the FabH mutations into BXE_198 and BXE_233.

Figure 14:
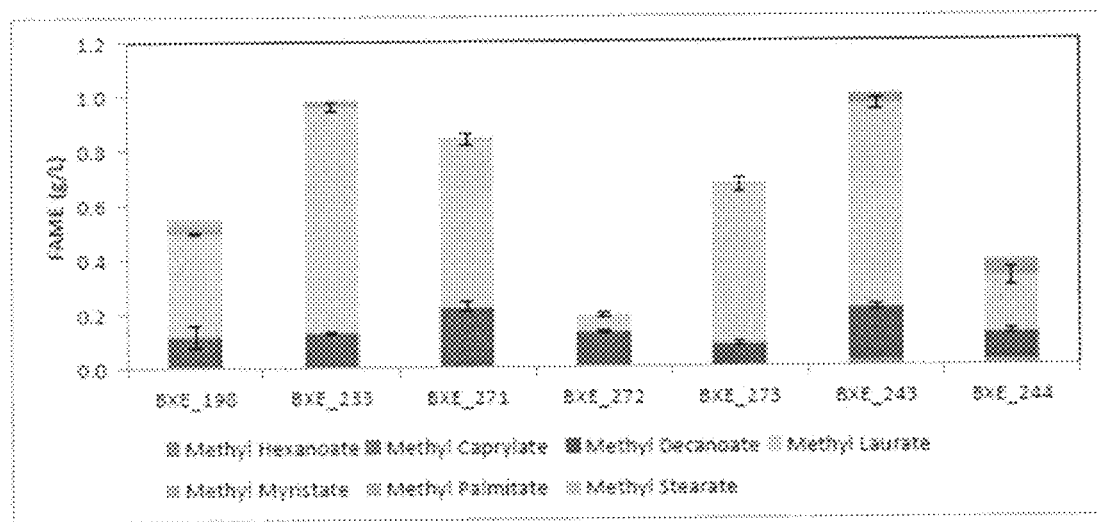
FIG. 14 is a graph showing FAME production in standard 1 mL method after 20 hours of production. (Note: BXE_198 is the control comparison for BXE_271-273 and BXE_233 is the control for BXE_243-244).

Strains were evaluated in the standard 1 mL screening protocol for FAME production in 20 hours (FIG. 14). As shown below, increased methyl laurate observed with the E37K (strain BXE_271) and D196G/K342E (strains BXE_273 and BXE_243) variants compared with the control strains (strains BXE_198 and BXE_233). However, as with the hbd/crt module, it is expected that these mutations may have a greater impact in production strains with improved WES activity.

It has been consistently demonstrated with current production strains that the required expression of Aagr FabH to achieve target activities in lysate requires a significant fraction of the total protein pool. Furthermore, even with a high level of expression, the FabH activity on C10-CoA is often times at or slightly below the target activity.

TABLE 4d

The following strains were constructed by incorporating the FabH mutations into BXE_198 and BXE_233.

| Strain | Parent(s) | Plasmid 1 | Plasmid 2 |
|---|---|---|---|
| BXE_198 | BX_1018 | pET-PpstsIH-Aagr-T5 Maqu | pACYC_PpstsIH nphT7 (SV)-ter-PpstsIH-fadB |
| BXE_233 | BX_1018 | pET_PpstsIH-Aagr-PtpiA-accDA_PrpiA-accB-accC | pACYC-PpstsIH-nphT7 (SV)-ter-PpstsIH-fadB-PphoE-Mhyd |
| BXE_271 | BX_1018 | pET_PpstsIH-Aagr(E37K)-PT5-Maqu | pACYC_PpstsIH nphT7 (SV)-ter-PpstsIH-fadB |
| BXE_272 | BX_1018 | pET_PpstsIH-Aagr(E51G, S357G)-PT5-Maqu | pACYC_PpstsIH nphT7 (SV)-ter-PpstsIH-fadB |
| BXE_273 | BX_1018 | pET_PpstsIH-Aagr(D196G, K342E)-PT5-Maqu | pACYC_PpstsIH nphT7 (SV)-ter-PpstsIH-fadB |
| BXE_243 | BX_1018 | pET_PpstsIH-Aagr(D196G, K342E)-PtpiA-accDA_PrpiA-accB-accC | pACYC-PpstsIH-nphT7 (SV)-ter-PpstsIH-fadB-PphoE-Mhyd |
| BXE_244 | BX_1018 | pET_PpstsIH-Aagr(D196G, Q219R)-PtpiA-accDA_PrpiA-accB-accC | pACYC-PpstsIH-nphT7 (SV)-ter-PpstsIH-fadB-PphoE-Mhyd |

Example 2

Optimization of Wax Ester Synthase (WES) Activity for Methyl Laurate Production

Figure 6:
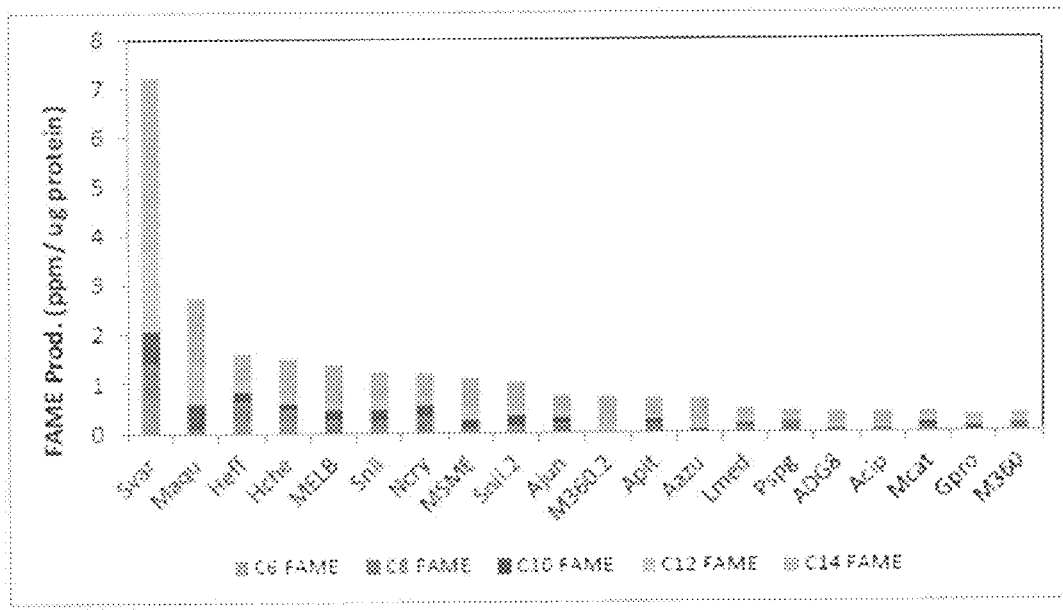
FIG. 6 is a graph showing product formation measured for 20 soluble WES candidates. Purified candidate enzymes were incubated individually with methanol and C6- to C14-CoA substrates to assess product formation.

WES candidates were expressed, purified, and evaluated for solubility and FAME production in vitro. Based on the results of the initial screen, 21 WES candidates were chosen for further evaluation including substrate specificity and in vivo FAME production. In vitro assays were completed by measuring product formation following the addition of individual CoA substrates. As summarized in FIG. 6, a range of activities was observed on the various substrates and a number of candidates were identified based on high overall activity (Svar, Maqu) or specificity for substrates ≥C12-CoA (M360.2, Acip). The sequences of the WES used are provided in Table 1 above.

As an orthogonal method for testing in vivo activity, nine of the WES candidates (Table 4f) shown to be active on lauroyl-CoA in the presence of methanol were expressed in a fatty acid production host.

TABLE 4f

Nine WES candidates shown to be active on lauroyl-CoA in the presence of methanol were expressed in a fatty acid production host

| Strain | Host | Plasmid 1 | Plasmid 2 |
|---|---|---|---|
| BXE_003 | BX_926 | 583_pET28b-ΔlacI-PpstsIH-fadBA | 1005_pACYC-PpstsIH-nphT7-ter-TT_PpstsIH-Abor |
| BXE_013 | BX_926 | 583_pET28b-ΔlacI-PpstsIH-fadBA | 1071_pACYC-PpstsIH-npht7-ter-PpstsIH-Gpro |
| BXE_016 | BX_926 | 583_pET28b-ΔlacI-PpstsIH-fadBA | 1076_pACYC-PpstsIH-npht7-ter-PpstsIH-Requ |
| BXE_017 | BX_926 | 583_pET28b-ΔlacI-PpstsIH-fadBA | 1077_pACYC-PpstsIH-npht7-ter-PpstsIH-LMED |
| BXE_018 | BX_926 | 583_pET28b-ΔlacI-PpstsIH-fadBA | 1078_pACYC-PpstsIH-npht7-ter-PpstsIH-Aazu |
| BXE_019 | BX_926 | 583_pET28b-ΔlacI-PpstsIH-fadBA | 1079_pACYC-PpstsIH-npht7-ter-PpstsIH-Msme |
| BXE_020 | BX_926 | 583_pET28b-ΔlacI-PpstsIH-fadBA | 1080_pACYC-PpstsIH-npht7-ter-PpstsIH-Ajun |
| BXE_021 | BX_926 | 583_pET28b-ΔlacI-PpstsIH-fadBA | 1081_pACYC-PpstsIH-npht7-ter-PpstsIH-M360.2 |
| BXE_022 | BX_926 | 583_pET28b-ΔlacI-PpstsIH-fadBA | 1082_pACYC-PpstsIH-npht7-ter-PpstsIH-ACIP |

Figure 7:
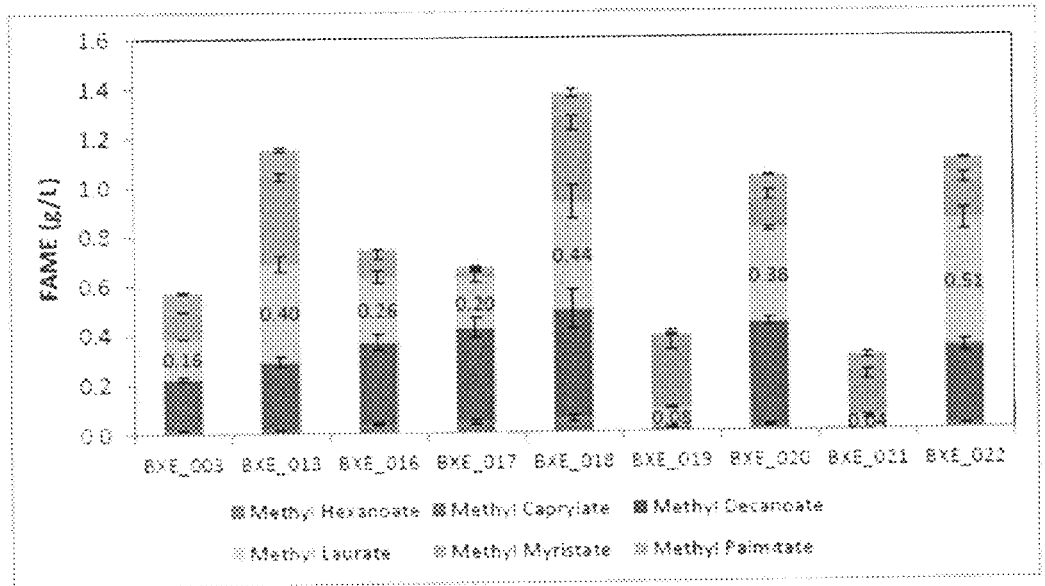
FIG. 7 is a graph showing FAME production at 24 hours for nine thiolase-based strains expressing different wax ester synthase candidates evaluated with the 2 mL small-scale protocol.

Small-scale evaluations were completed for each strain cultured at $OD_{600}$=2.0 in a 20 mL capped glass test tube with a working volume of 2 mL. Samples were taken at 24 hours by removing 1 mL of the culture for growth and glucose measurement and extracting the remaining broth with MTBE prior to analyzing for FAME production by GC-MS. As shown in FIG. 7, methyl laurate titers ranging from 0.04-0.5 g/L were observed, indicating modest in vivo WES activity.

Specificity of product formation observed in vivo was significantly different than what would be predicted based upon the in vitro assays. This discrepancy may have been due to the production profile of the thiolase FFA strains, which produced nearly equivalent titers from C6 to C16 FFA. Due to the limitations of screening the wax ester synthase candidates in the thiolase strain, subsequent in vivo characterization was performed in synthase-based strains, which produced C12 FFA and FAME products at higher specificity, rate and titer.

WES High-Throughput Screening

Figure 17:
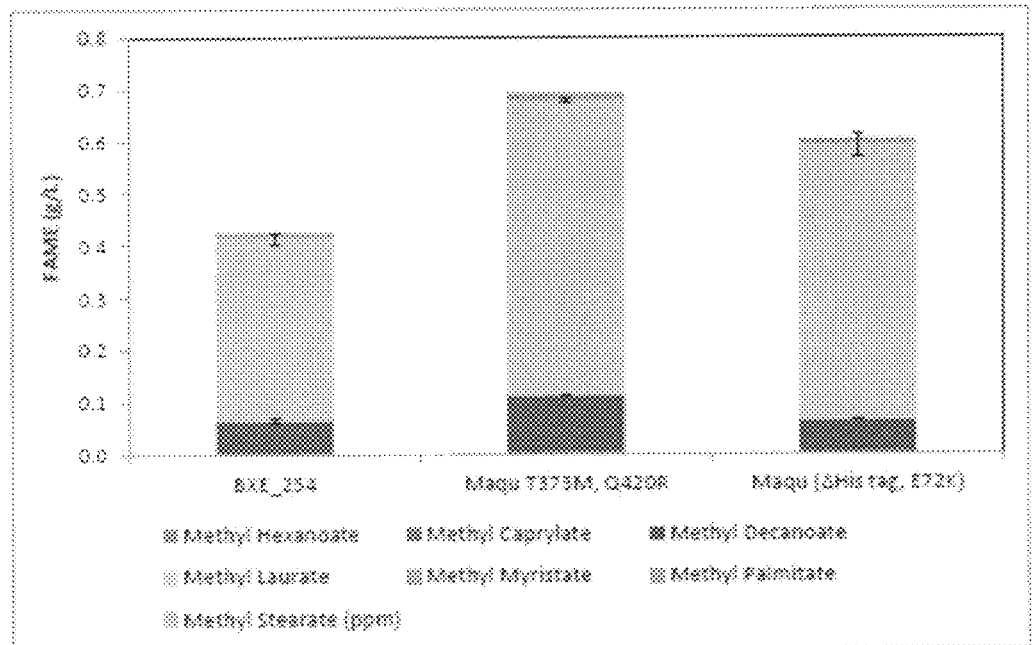
FIG. 17 is a graph showing FAME production in standard 1 mL method after 20 hours of production with Maqu mutants (SEQ ID NOs:7 and 8).

A 96-well plate, Nile red-based assay has been developed for high-throughput quantification of FAME production by fluorescence. Mutant libraries were constructed with Maqu WES. The top 20 mutants identified in the screen have been isolated, sequenced, cloned into production hosts and evaluated for FAME and FFA production in the 1 mL method. While comprehensive data analysis for the 1 mL confirmations is pending, initial results showed significantly improved FAME production with at least two WES constructs identified by this method. As demonstrated in FIG. 17, both mutations resulted in improved methyl laurate production when compared with the control strain, while maintaining a high degree of specificity.

Figure 16:
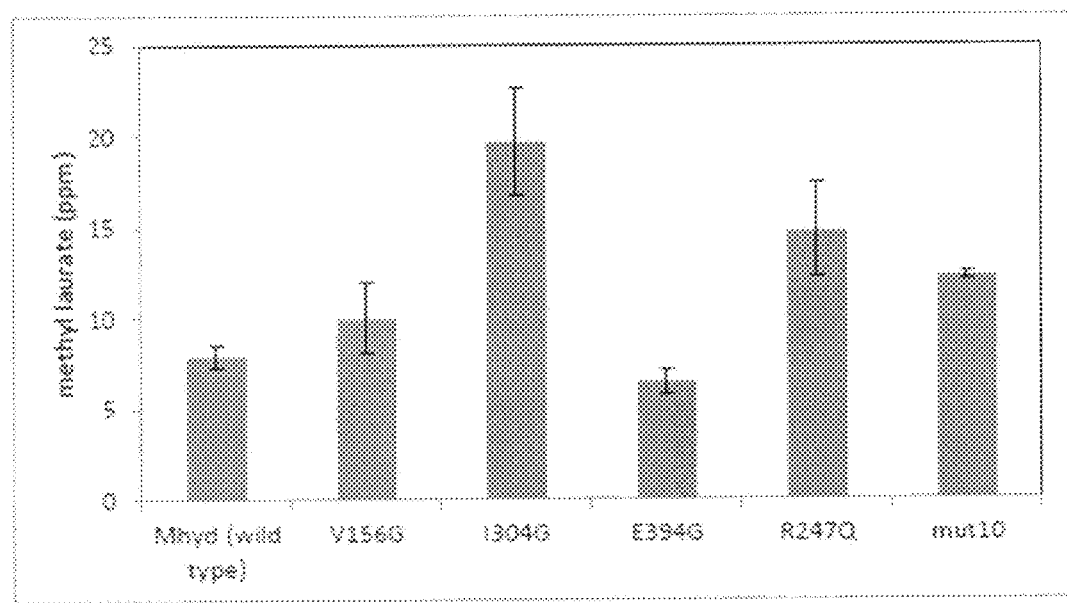
FIG. 16 is a graph showing in vitro product formation from methanol and C12-CoA after incubation for 5 minutes with purified Mhyd variants as measured by GC-MS.

Similarly, mutants of Mhyd were made and the methyl laurate production determined. The results are shown in FIG. 16.

Example 3

Construction and Evaluation of Methyl Laurate Producing Strains
Engineering of Strains for Methyl Laurate Production Numerous methyl laurate production strains have been constructed, incorporating key pathway modules developed in Examples 1 and 2 above and building upon the malonyl-CoA production technology as described in WO2014026162A1 (OPX Biotechnologies Inc., USA). Small-scale evaluations were completed for each strain cultured at $OD_{600}$=2.0 in a 20 mL capped glass test tube with a working volume of 1 mL. Samples were taken at 24 hours by extracting the entire culture with MTBE and analyzing for FAME production by GC-MS. This 1 mL protocol was instituted in an effort to reduce volatile loss of FAME products seen during shake flask evaluations.

TABLE 5 methyl laurate production strains used in Example 3

| Strain # | Base strain | Plasmid 1 | Plamid 2 |
|---|---|---|---|
| BXE_233 | BX_1018 | pET_PpstsIH-Aagr-PtpiA-accDA-PtpiA-accB-accC | pACYC-PpstsIH-nphT7 (SV)-ter-PpstsIH-fadB-PphoE-Mhyd |
| BXE_275 | BX_1018 | pET_PpstsIH-Aagr-PtpiA-accDA-PtpiA-accB-accC | pACYC-PpstsIH-nphT7 (SV)-ter-PpstsIH-fadB-PphoE-Aazu |
| BXE_276 | BX_1018 | pET_PpstsIH-Aagr-PtpiA-accDA-PtpiA-accB-accC | pACYC-PpstsIH-nphT7 (SV)-ter-PpstsIH-fadB-PphoE-Hche |
| BXE_279 | BX_1018 | pET_PpstsIH-Aagr-PtpiA-accDA-PtpiA-accB-accC | pACYC-PpstsIH-nphT7 (SV)-ter-PpstsIH-fadB-PphoE-Maqu |

Figure 8:
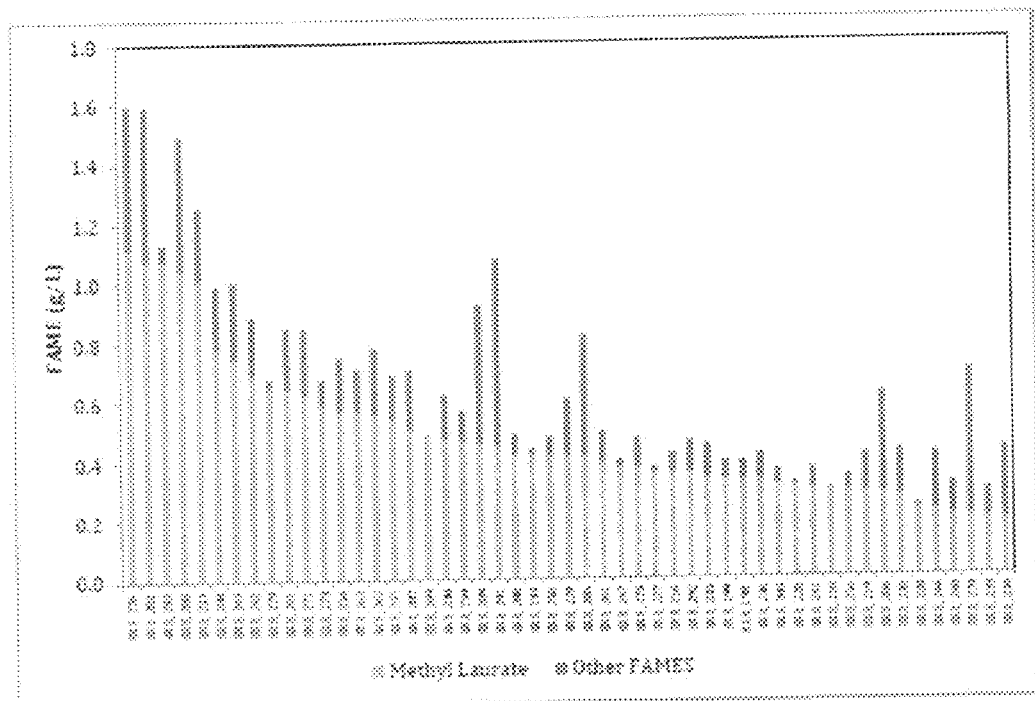
FIG. 8 is a graph showing the production of methyl laurate and other FAMEs (C6-C14) in 1 ml, 24 hour strain screening assay by 50 strains engineered with various versions of the synthase pathway for methyl laurate production.

In FIG. 8, 24 hour FAME production data is shown for 50 of the >100 methyl laurate producing strains screened in the 1 ml assay since the May SCM. In this strain set, titers >1 g/L have been obtained in 20 hours of production with biomass levels ~1 gDCW/L. Furthermore, specificities between 70-98% on a FAME basis have been observed.

Figure 15:
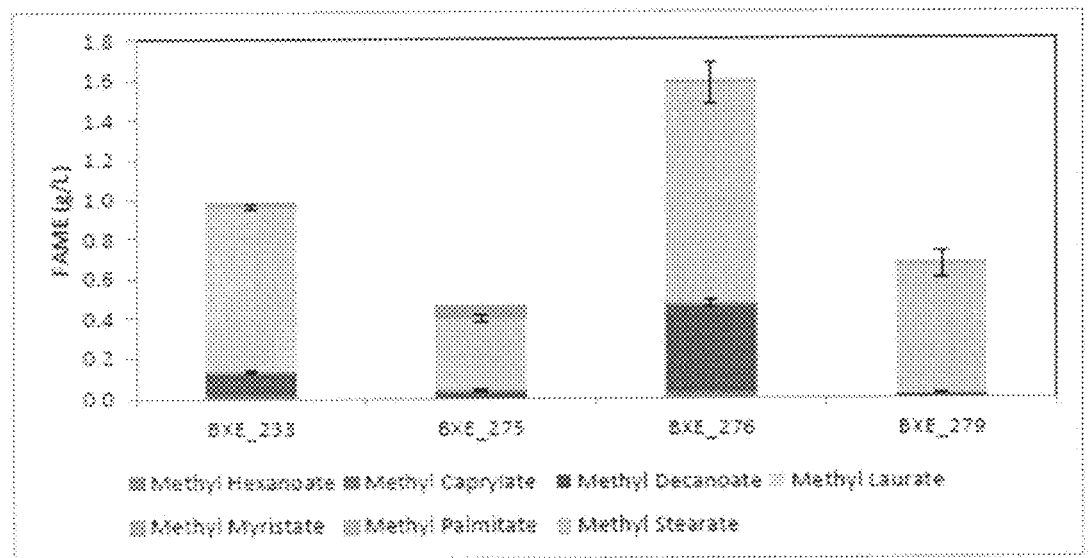
FIG. 15 is a graph showing FAME production in standard 1 mL method after 20 hours of production with alternative WES enzyme candidates.
Figure 18:
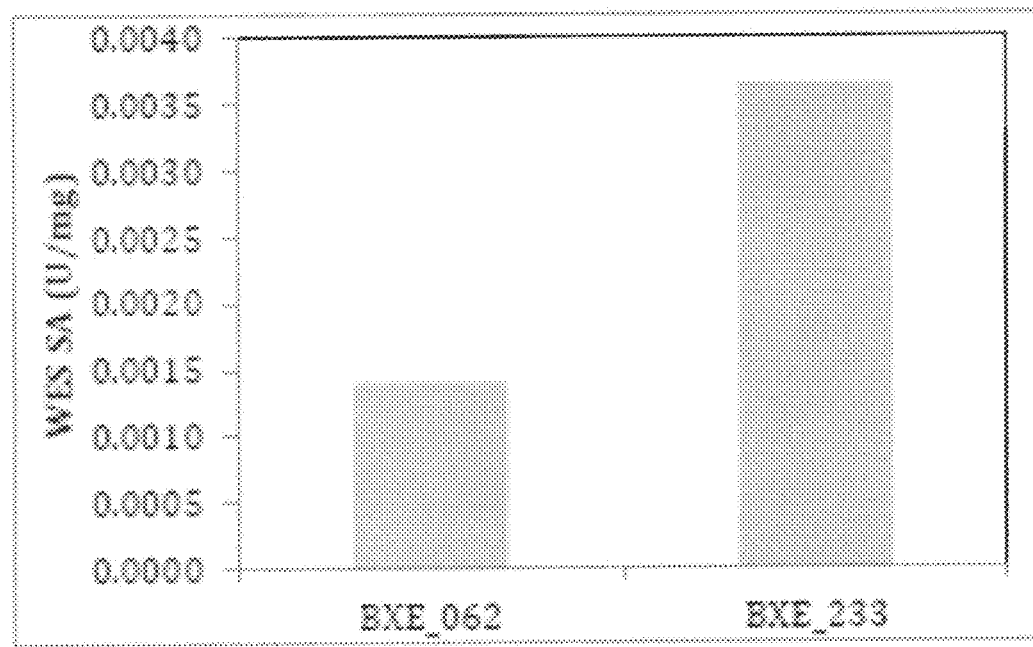
FIG. 18 is a graph showing WES enzyme activities for BXE_062 and BXE_233 cell lysates as measured by product formation over time by GC-MS. The target activity for WES in cell lysates is 0.02 U/mg.

FIG. 15 shows the 1 mL screening results for strains expressing four WES candidates shown in Table 5. These results show that varying the WES leads to significant changes in methyl laurate production. Furthermore, Hche showed high levels of production. FIG. 18 also shows that while the majority of the activities (FabH, FadB, Ter) were not significantly different between the two hosts, BXE_233 and BXE_062, the WES activity was nearly three-fold higher in BXE_233 when compared with BXE_062. The significant differences in methyl laurate production seen with differing WES candidates, and with different expression constructs for the same WES enzyme, support the hypotheses that WES activity remains limiting in current production strains.

Example 4

Fermentation Method Development and Optimization for Methyl Laurate Production
Initial Development of a 1 L Bioprocess for Methyl Laurate Production Development of a 1 L bioprocess for methyl laurate was carried out to support evaluation of production strains under pH-controlled conditions and at biomass concentrations more representative of commercial production.

Several process parameters (Table 6) were explored, including pH setpoint, methanol feeding, temperature profile and incorporation of a second phase for increased FAME recovery.

Figure 9:
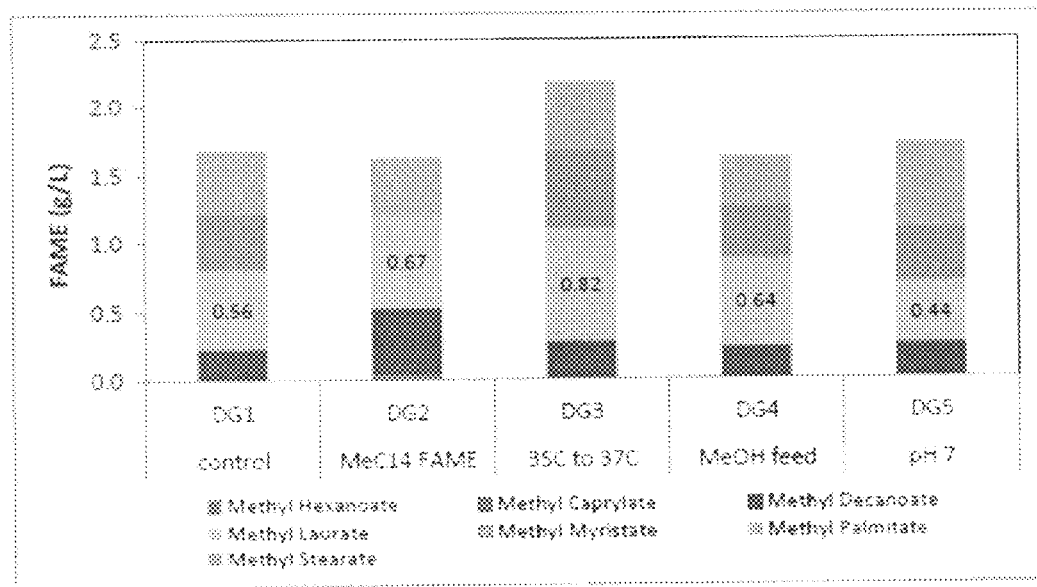
FIG. 9 is a graph showing FAME product distribution exhibited by strain BXE_022 after 40 hrs in 1 L fermentation under various test conditions.
Figure 10:
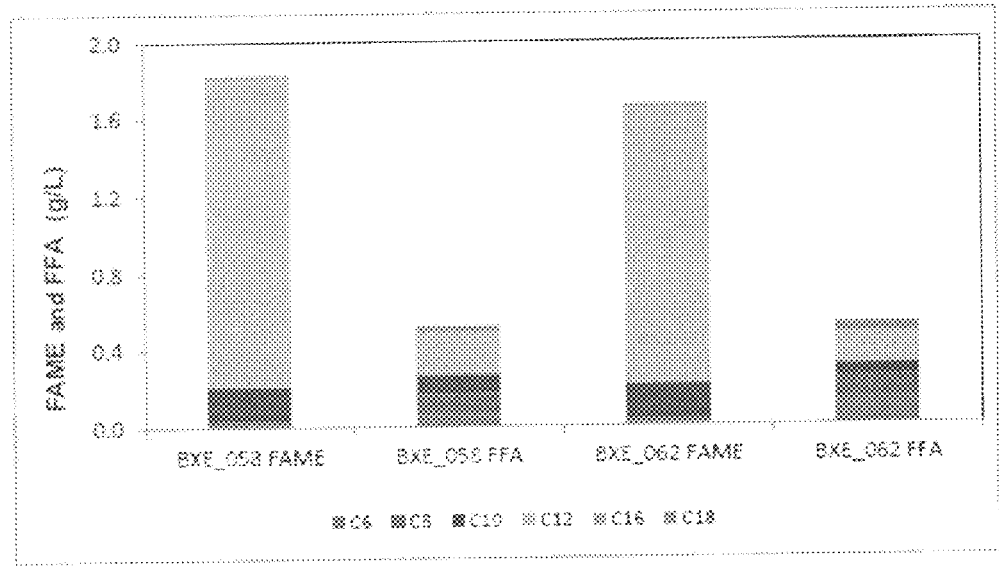
FIG. 10 is a graph showing FAME and FFA concentration distribution for strains BXE_058 and BXE_062 at approximately 45 hours of production; methyl myristate concentration was not include in the analysis as 50 g/L was added as a second phase.

A subset of the data generated is shown in FIG. 9. Overall, the methanol feeding and control strategy did not appear to have a significant impact on methyl laurate production or overall fermentation performance. The inclusion of a second phase appeared to be a slight, positive effect on FAME recovery. The incorporation of the 35° C. to 37° C. temperature shift profile showed a positive effect on production. Based on these results, the following baseline process as shown in Table 7 was established and utilized for the subsequent 1 L fermentations and evaluations of methyl laurate producing strains engineered in Example 3.

TABLE 6

Several process parameters used in Example 4

| Condition | Methanol Feed Profile | $2^{nD}$ Phase | Production Temperature Profile | Production pH | Medium |
|---|---|---|---|---|---|
| Control | 1% (v/v) MeOH added at TS; bolus additions every 8-12 hours to maintain 1% | N/A | 37° C. | 7.4 | FM12 + 9 mM phosphate |
| MeC14 FAME | 1% (v/v) MeOH added at TS; bolus additions every 8-12 hours to maintain 1% | 50 g/L C14 FAME | 37° C. | 7.4 | FM12 + 9 mM phosphate |
| 35 C. to 37 C. | 1% (v/v) MeOH added at TS; bolus additions every 8-12 hours to maintain 1% | N/A | 35° C. → 37° C. | 7.4 | FM12 + 9 mM phosphate |
| MeOH Feed | 0.5% (v/v) MeOH added at TS; continuous feed to maintain 0.5% (v/v) | N/A | 37° C. | 7.4 | FM12 + 9 mM phosphate |
| pH 7 | 1% (v/v) MeOH added at TS; bolus additions every 8-12 hours to maintain 1% | N/A | 37° C. | 7.4 | FM12 + 9 mM phosphate |

TABLE 7

Baseline process used in fermentation of methyl laurate producing strains engineered in Example 3

| Condition | Methanol Feed Profile | $2^{nD}$ Phase | Production Temperature Profile | Production pH | Medium |
|---|---|---|---|---|---|
| Baseline Process | 1% (v/v) MeOH added at TS; bolus additions every 8-12 hours to maintain 1% | 50 g/L C14 FAME | 35° C. → 37° C. | 7 | FM12 + 9 mM phosphate |

Figure 19:
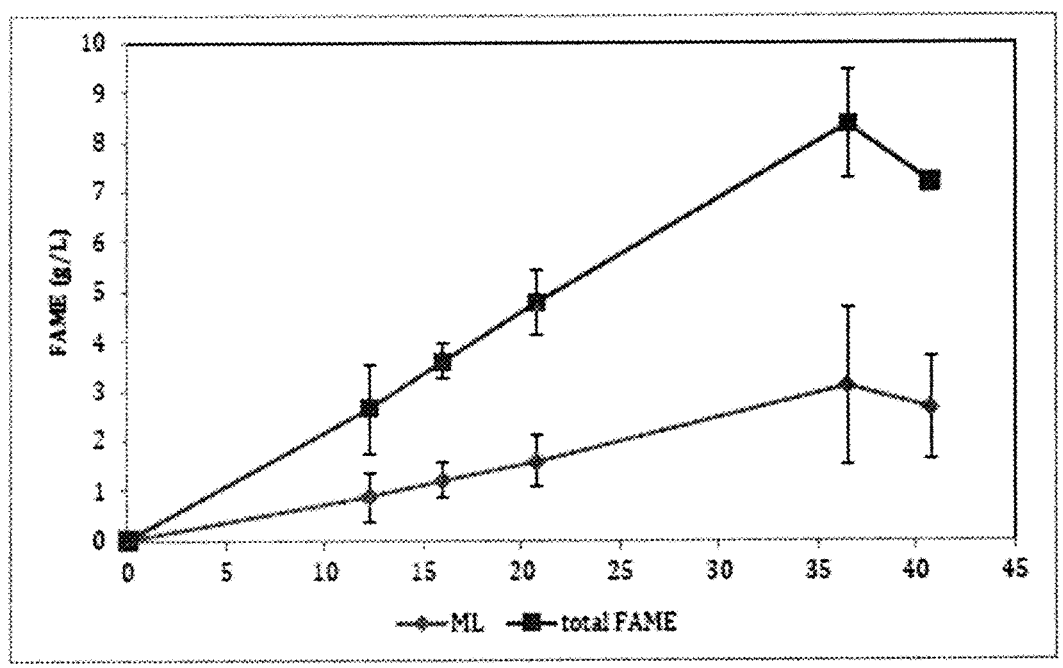
FIG. 19 is a graph showing average production profile for methyl laurate and total FAME for 1 L fermentations with BXE_276 in the FM14 process.

BXE_276 strain was tested as mentioned above. The average production time course for the triplicate BXE_276 was run. Fairly constant methyl laurate production rates were observed over 36.5 hours with an average titer of 3 g/L methyl laurate. Interestingly, this strain produced a significant amount of methyl decanoate (3-5 g/L), resulting in significantly higher total FAME production than observed with previous strains (FIG. 19). BXE_276 showed higher specificity for production of methyl decanoate than methyl laurate in 1 L, which is in contrast to the higher specificity demonstrated in 1 mL for methyl laurate production (69%).

REFERENCES

Heath et al., Prog. Lipid Res. 40(6):467-97 (2001)
McCue et al., *Nucleic Acids Res.*, 29(3):774-82 (2001)
Zhang et al., *J. Biol. Chem.* 277 (18):15558-65 (2002)
Chang et al., *J. Bacteriol.* 154(2):756-62 (1983)
Abdel-Ahmid et al., *Microbiol.* 147(6):2001
Mat-Jan et al., *J. Bacteriol.* 171(1):342-8
Bunch et al., *Microbiol.* 143(1):187-95 (1997)
Enoyl-Acyl Carrier Protein (fabI) Plays a Determinant Role in Completing Cycles of Fatty Acid Elongation in *Escherichia coli*," Richard J. Heath and Charles O. Rock, J. Biol. Chem. 270:44, pp. 26538-26543 (1995),
Beguin, P and Aubert, J-P (1994) FEMS Microbial. Rev. 13: 25-58
Ohima, K. et al. (1997) Biotechnol. Genet. Eng. Rev. 14: 365414.
Antonenkov, V., D. et al. Van Veldhoven, P., P., Waelkens, E., and Mannaerts, G. P. *J. Biol. Chem.* 1997, 272:26023-26031.
Reed, 1981
Arthur Lesk (2008), Introduction to bioinformatics, $3^{rd}$ edition,
Thompson et al., Nucleic Acids Research 22, 4637-4680, 1994,
Katoh et al., Genome Information, 16(1), 22-33, 2005.
U.S. provisional patent application No. 62/044,621 filed Sep. 2, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A microbial cell for producing at least one fatty acid ester, wherein the cell is genetically modified to comprise:
   (i) a first genetic mutation that enables the cell to produce at least one fatty acid and/or acyl coenzyme A (CoA) thereof by increased enzymatic activity in the cell relative to a malonyl-CoA dependent and malonyl-ACP independent fatty acyl-CoA metabolic pathway of a wild type cell, wherein the fatty acid comprises at least 5 carbon atoms; and
   (ii) a second genetic mutation that increases the activity of at least one wax ester synthase in the cell relative to the wild type cell and the wax ester synthase has sequence identity of at least 80% to a polypeptide set forth in SEQ ID NO: 1, 85% to a polypeptide as set forth in SEQ ID NO: 3, 85% to a polypeptide as set forth in SEQ ID NO: 4, 90% to a polypeptide as set forth in SEQ ID NO: 5, 95% to a polypeptide as set forth in SEQ ID NO: 7, or 98% to a polypeptide as set forth in SEQ ID NO: 8, and combinations thereof or to a functional fragment of any of the polypeptides for catalyzing the conversion of fatty acid and/or acyl coenzyme A thereof to the fatty acid ester.

2. The cell according to claim 1, wherein the first genetic mutation results in an increase in the expression of at least one enzyme selected from the group consisting of acetoacetyl-CoA synthase, ketoacyl-CoA synthase (or elongase), ketoacyl-CoA thiolase, enoyl-CoA reductase, ketoacyl-CoA reductase and 3-hydroxyacyl-CoA dehydratase.

3. The cell according to claim 1, further comprising a genetic mutation that results in a decrease in the expression of acetoacetyl-CoA thiolase relative to the wild type cell.

4. The cell according to claim 1, wherein the cell comprises a third genetic mutation that reduces the fatty acid degradation capacity of the cell relative to the wild type cell.

5. The cell according to claim 4, wherein the third genetic mutation results in a decrease in the expression of at least one enzyme selected from the group consisting of acyl-CoA dehydrogenase, 2,4-dienoyl-CoA reductase, enoyl-CoA hydratase and 3-ketoacyl-CoA thiolase, each relative to the wild type cell.

6. The cell according to claim 1, wherein the fatty acid is lauric acid, the acyl coenzyme A thereof is lauroyl coenzyme A and the fatty acid ester is selected from the group consisting of methyl laurate, ethyl laurate, propyl laurate, butyl laurate and pentyl laurate.

7. The cell according to claim 6, wherein the cell comprises a first mutation that results in at least an increase in the expression of β-ketoacyl-ACP synthase III (fabH).

8. The cell according to claim 7, wherein the β-ketoacyl-ACP synthase III (fabH) has sequence identity of
  at least 85% to a polypeptide selected from the group consisting of SEQ ID NOs: 24-27 and combinations thereof.

9. The cell according to claim 6, wherein the cell is further genetically modified to increase the expression of 3-hydroxyacyl coenzyme A dehydratase (3HCDh) and/or keto acyl-CoA reductase (KCR) relative to the wild type cell.

10. The cell according to claim 9, wherein the 3HCDh is crotonase/enoyl-CoA hydratase (Crt) and the KCR is hydroxybutyric dehydrogenase (Hbd).

11. The cell according to claim 10, wherein the Crt has sequence identity of at least 85% to a polypeptide as set forth in SEQ ID NO:28 and/or the Hbd has sequence identity of at least 85% to a polypeptide of SEQ ID NO:29.

12. The cell according to claim 1, wherein the fatty acid ester is produced in the presence of at least one exogenous alcohol selected from the group consisting of methanol, ethanol, propanol, butanol and pentanol.

13. A method for producing methyl laurate, the method comprising:
  contacting lauric acid and/or lauroyl coenzyme A with an isolated wax ester synthase that has sequence identity of at least 80% to a polypeptide set forth in SEQ ID NO: 1, 85% to a polypeptide as set forth in SEQ ID NO: 3, 85% to polypeptide as set forth in SEQ ID NO: 4, 90% to a polypeptide as set forth in SEQ ID No: 5, 95% to a polypeptide as set forth in SEQ ID NO: 7, or 98% to a polypeptide as set forth in SEQ In NO: 8.

14. A method for producing at least one fatty acid ester, the method comprising culturing a microbial cell which is genetically modified to comprise:
  (i) a first genetic mutation that enables the cell to produce at least one fatty acid and/or acyl coenzyme A (CoA) thereof by increased enzymatic activity in the cell relative to a malonyl-CoA dependent and malonyl-ACP independent fatty acyl-CoA metabolic pathway of a wild type cell, wherein the fatty acid comprises at least 5 carbon atoms; and
  (ii) a second genetic mutation that increases the activity of at least one wax ester synthase in the cell relative to the wild type cell and the wax ester synthase has sequence identity of at least 80% to a polypeptide set forth in SEQ ID NO: 1, 85% to a polypeptide as set forth in SEQ ID NO: 3, 85% to a polypeptide as set forth in SEQ ID NO: 4, 90% to a polypeptide as set forth in SEQ ID NO: 5, 95% to a polypeptide as set forth in SEQ ID NO: 7, or 98% to a polypeptide as set forth SEQ ID NO: 8, and combinations thereof or to a functional fragment of any of the polypeptides for catalyzing the conversion of fatty acid and/or acyl coenzyme A thereof to the fatty acid ester.

* * * * *